United States Patent
Bae et al.

(10) Patent No.: US 9,923,143 B2
(45) Date of Patent: Mar. 20, 2018

(54) FULLERENE DERIVATIVE, ORGANIC SOLAR CELL USING SAME, AND MANUFACTURING METHOD THEREOF

(71) Applicant: LG CHEM, LTD., Seoul (KR)

(72) Inventors: Jaesoon Bae, Daejeon (KR); Jaechol Lee, Daejeon (KR); Jiyoung Lee, Daejeon (KR); Hangken Lee, Daejeon (KR); Songrim Jang, Daejeon (KR); Jeong Min Choi, Daejeon (KR); Jinseck Kim, Daejeon (KR); Keun Cho, Daejeon (KR); Doo Whan Choi, Daejeon (KR)

(73) Assignee: LG CHEM, LTD., Seoul (KR)

(*) Notice: Subject to any disclaimer, the term of this patent is extended or adjusted under 35 U.S.C. 154(b) by 293 days.

(21) Appl. No.: 14/778,797

(22) PCT Filed: Apr. 17, 2014

(86) PCT No.: PCT/KR2014/003339
§ 371 (c)(1),
(2) Date: Sep. 21, 2015

(87) PCT Pub. No.: WO2014/171755
PCT Pub. Date: Oct. 23, 2014

(65) Prior Publication Data
US 2016/0056383 A1 Feb. 25, 2016

(30) Foreign Application Priority Data
Apr. 17, 2013 (KR) .................. 10-2013-0042114

(51) Int. Cl.
| | | |
|---|---|---|
| *H01L 51/00* | (2006.01) | |
| *C01B 32/152* | (2017.01) | |
| *C07C 69/616* | (2006.01) | |
| *C07C 69/75* | (2006.01) | |
| *C07C 69/753* | (2006.01) | |
| *C07C 219/32* | (2006.01) | |
| *C07C 255/55* | (2006.01) | |
| *C07C 327/22* | (2006.01) | |
| *C07D 235/18* | (2006.01) | |
| *C07D 277/36* | (2006.01) | |
| *C07D 333/16* | (2006.01) | |
| *C07D 417/14* | (2006.01) | |
| *H01L 51/42* | (2006.01) | |

(52) U.S. Cl.
CPC ........ H01L 51/0047 (2013.01); C01B 32/152 (2017.08); C07C 69/616 (2013.01); C07C 69/75 (2013.01); C07C 69/753 (2013.01); C07C 219/32 (2013.01); C07C 255/55 (2013.01); C07C 327/22 (2013.01); C07D 235/18 (2013.01); C07D 277/36 (2013.01); C07D 333/16 (2013.01); C07D 417/14 (2013.01); *C07C 2601/14* (2017.05); *C07C 2602/08* (2017.05); *C07C 2602/10* (2017.05); *H01L 51/0037* (2013.01); *H01L 51/4253* (2013.01); *Y02E 10/549* (2013.01); *Y02P 70/521* (2015.11)

(58) Field of Classification Search
CPC .................. H01L 51/0047; C01B 32/152
See application file for complete search history.

(56) References Cited

U.S. PATENT DOCUMENTS

| | | |
|---|---|---|
| 2010/0308372 A1 | 12/2010 | Mitsui et al. |
| 2011/0001093 A1 | 1/2011 | Itoh et al. |
| 2012/0004476 A1 | 1/2012 | Yoon et al. |
| 2012/0043507 A1 | 2/2012 | Kronholm et al. |

FOREIGN PATENT DOCUMENTS

| | | |
|---|---|---|
| KR | 10-2010-0065323 A | 6/2010 |
| KR | 10-2010-0088050 A | 8/2010 |
| KR | 10-2010-0131390 A | 12/2010 |
| KR | 10-1046183 B1 | 6/2011 |
| KR | 10-2013-0027284 A | 3/2013 |

OTHER PUBLICATIONS

Li et al. "Why is the Rearrangement of [6,5] Open Fulleroids to [6,6] Closed Fullerenes Zero Order?" Journal of the American Chemical Society, 1997, vol. 119, pp. 1149-1150.*
Hall et al. "Observation of Both Thermal First-Order and Photochemical Zero-Order Kinetics in the Rearrangement of [6,5] Open Fulleroids to [6,6] Closed Fullerenes" Journal of the American Chemical Society, 2001, vol. 123, pp. 1349-1354.*
Lobez et al. "Improving the Performance of P3HT-Fullerene Solar Cells with Side-Chain-Functionalized Poly(thiophene) Additives: A New Paradigm for Polymer Design" ACS Nano, 2012, vol. 6, pp. 3044-3056.*
Roncali, J., "Linear pi-conjugated systems derivatized with C60-fullerene as molecular heterojunctions for organic photovoltaics," Chemical Society Reviews, vol. 34, Jan. 2005, pp. 483-495.
M. Angeles Herranz et al.: "Electroreductive retro-cyclopropanation reactions of nitrophenyl-methanofullerene derivatives", J. Mater Chem., vol. 12, 2002, pp. 2048-2053.
Zhou, Z., et al., First synthesis of ring-B C60-substituted derivatives of N,N-(tetrachlorophthaloyl) dehydroabietylamine, Tetrahedron, 2013, 69(1), pp. 43-49.

(Continued)

Primary Examiner — Joseph R Kosack
(74) Attorney, Agent, or Firm — Dentons US LLP

(57) ABSTRACT

The present specification relates to a fullerene derivative, an organic solar cell including the same, and a fabricating method thereof.

19 Claims, 9 Drawing Sheets

(56) References Cited

OTHER PUBLICATIONS

Hall, M.H., et al., "Observation of Both Thermal First-Order and Photochemical Zero-Order Kinetics in the Rearrangement of [6,5] Open Fulleroids to [6,6] Closed Fullerenes," Journal of the American Chemical Society, 2001, 123(7). pp. 1349-1354.

Li, Zizhong, et al., "Convenient Syntheses of 6,5 Open and 6,6 Closed Cycloalkylidenefullerenes," Tetrahedron Letters, 1996. 37(27). pp. 4651-4654.

* cited by examiner

【Fig. 1】
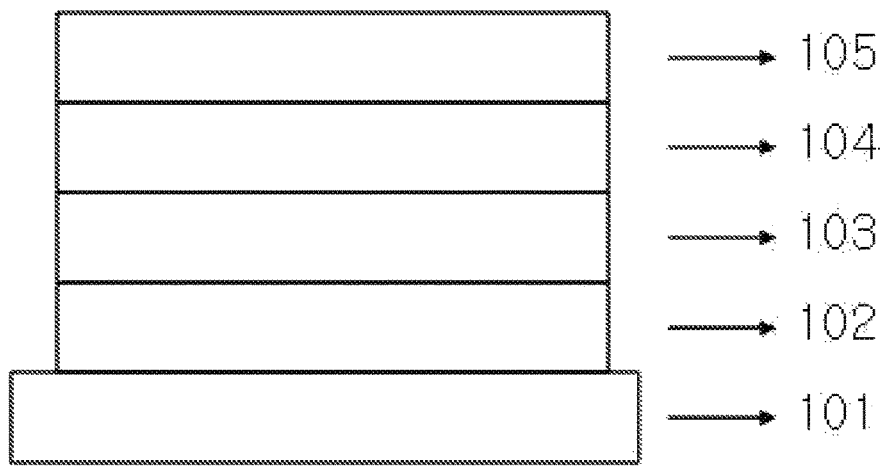
【Fig. 2】
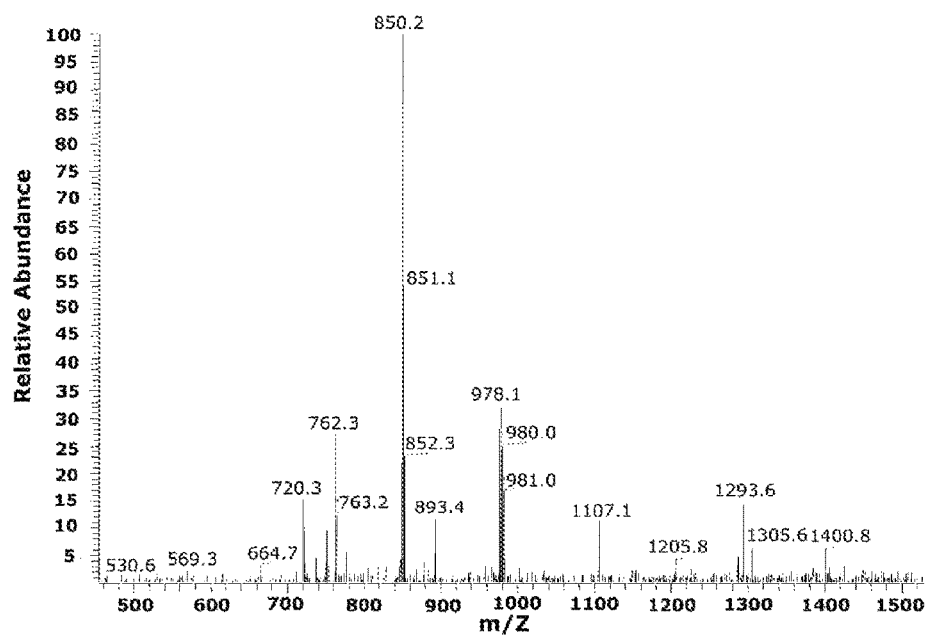

【Fig. 3】
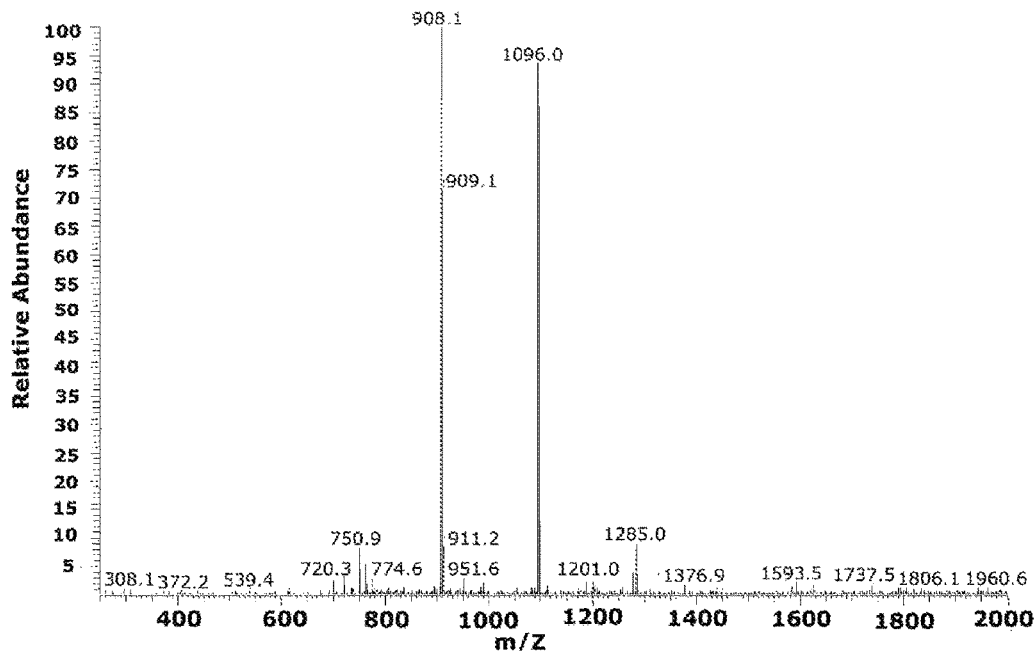
【Fig. 4】
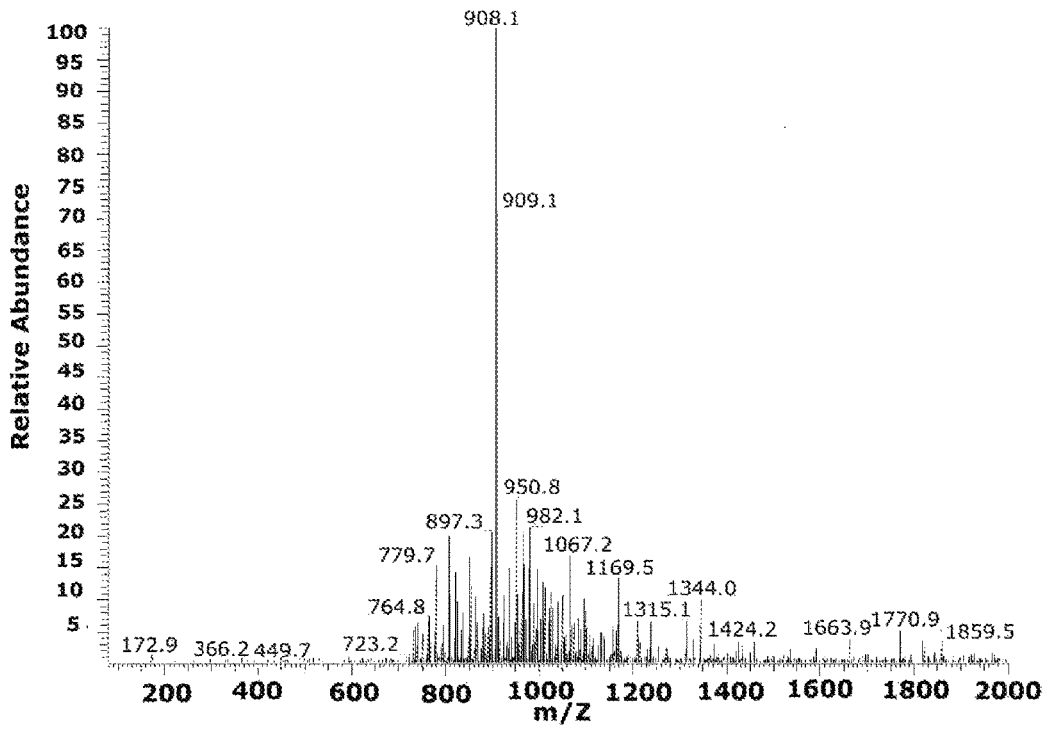

[Fig. 5]
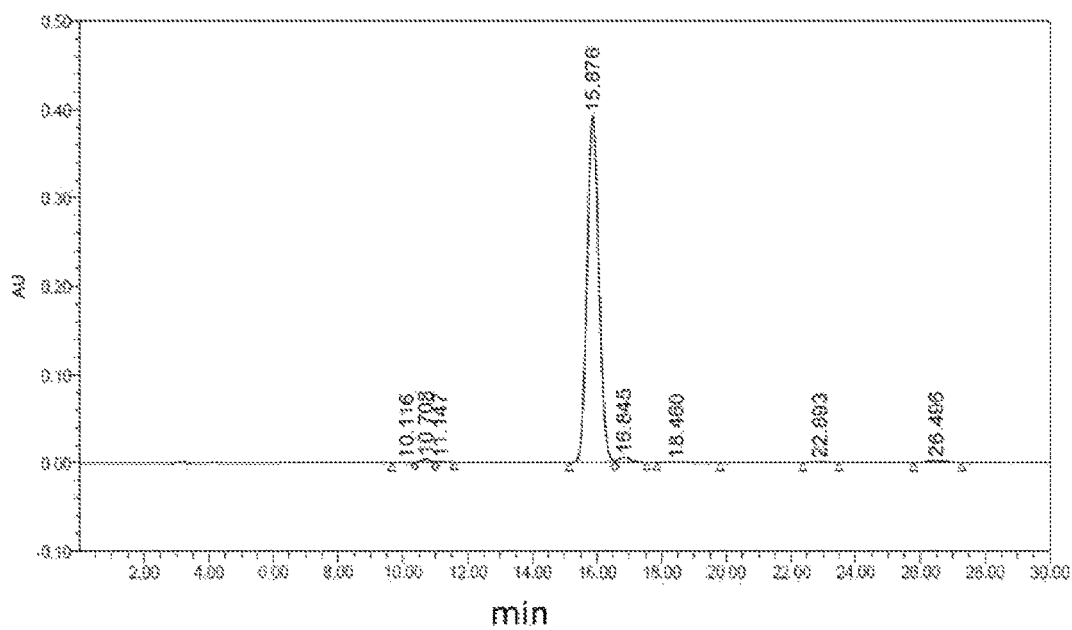

[Fig. 6]
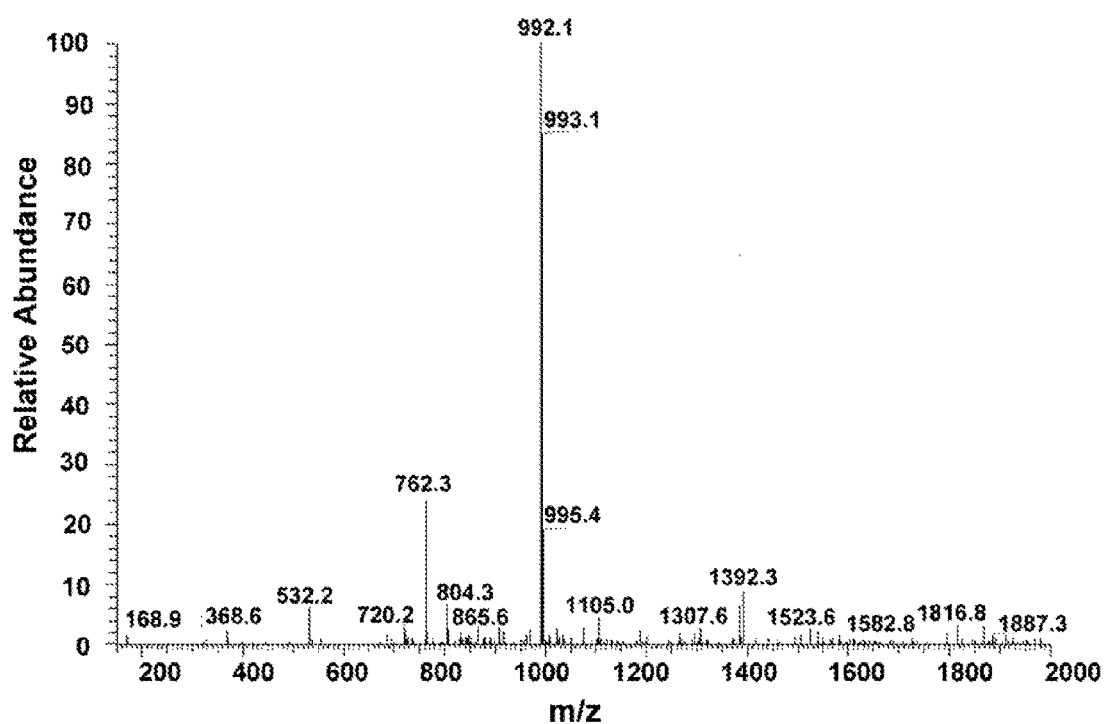

[Fig. 7]
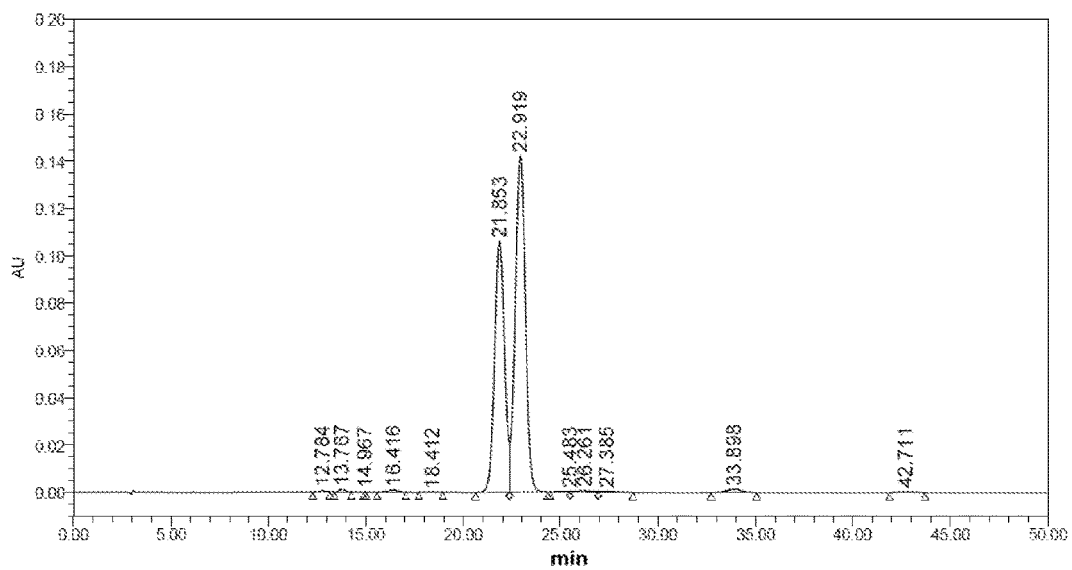

[Fig. 8]
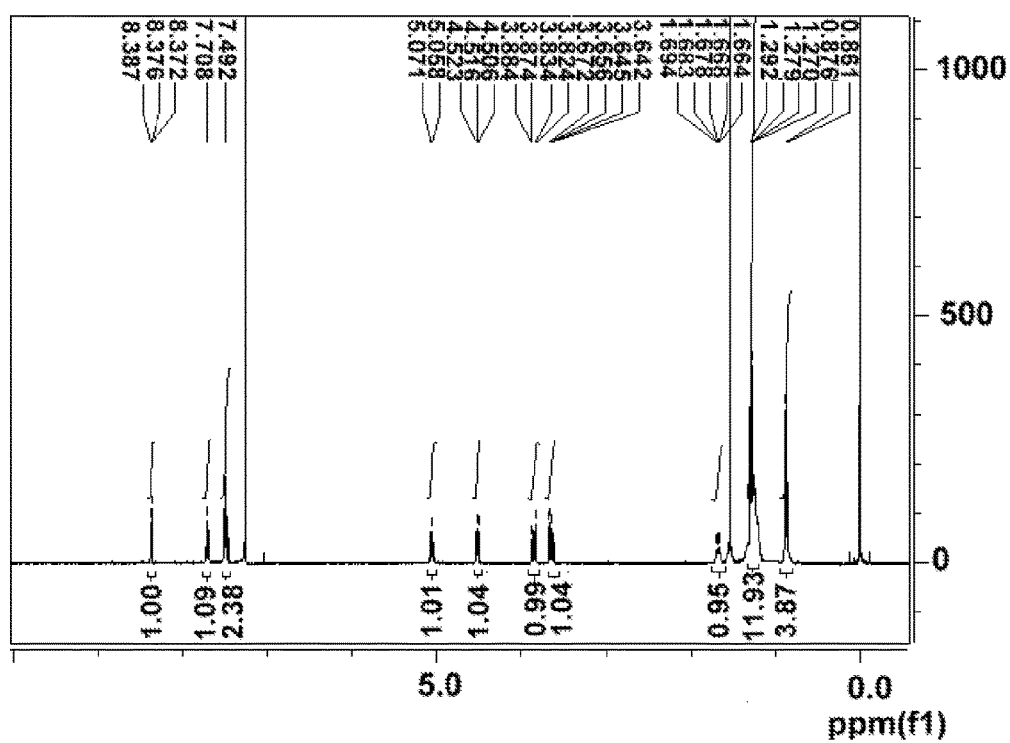

[Fig. 9]
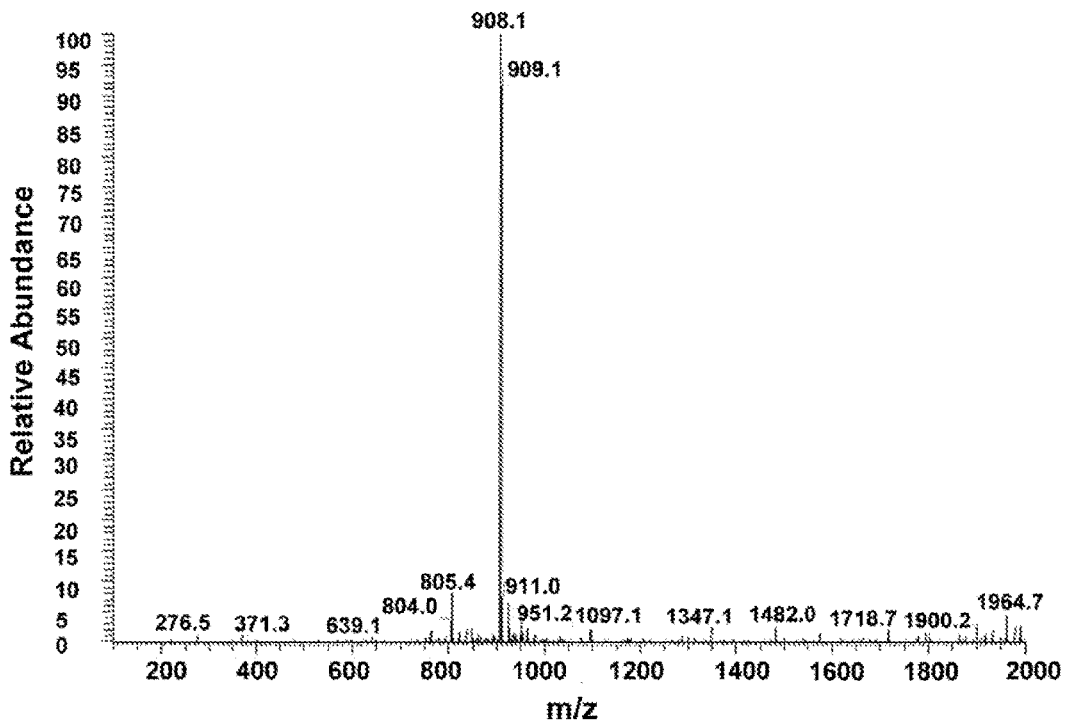
[Fig. 10]
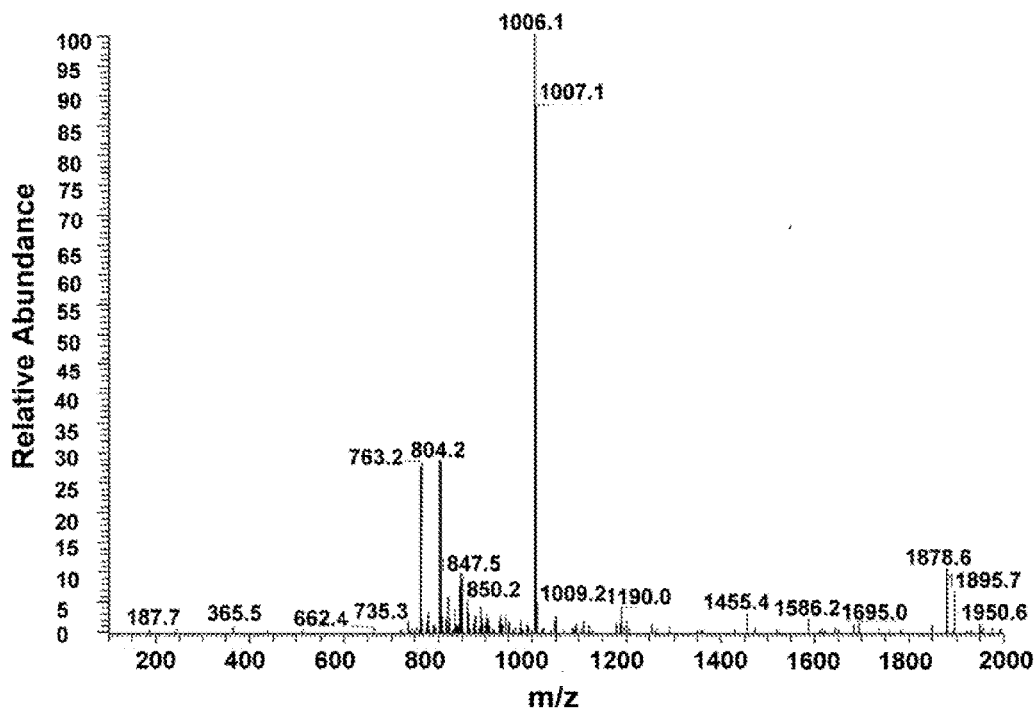

【Fig. 11】
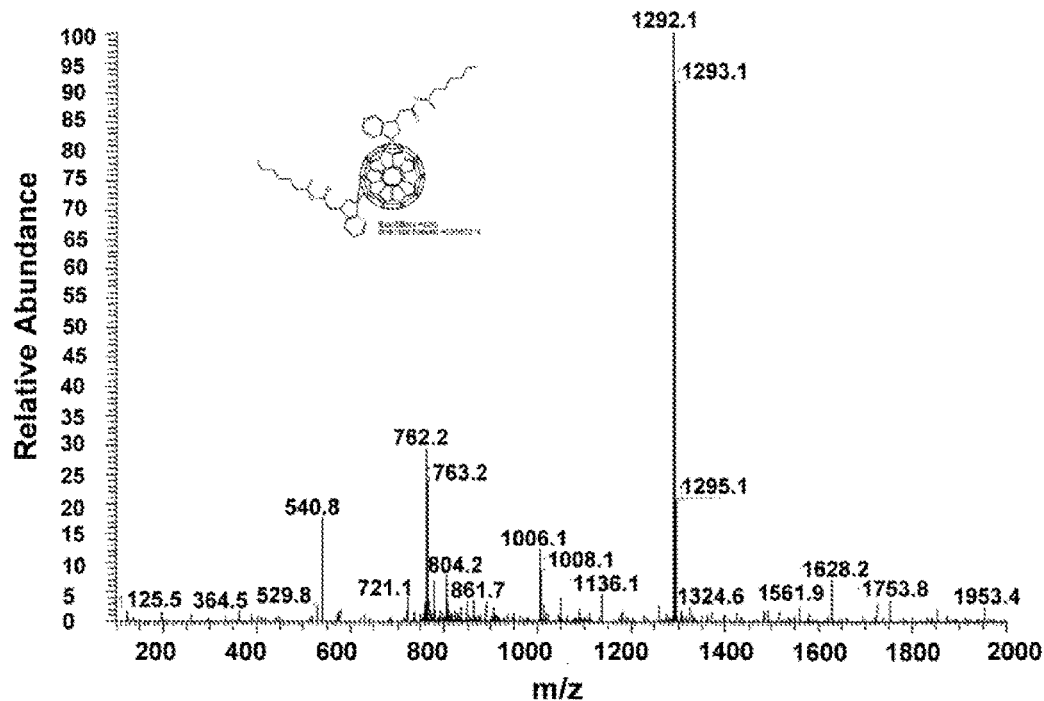
【Fig. 12】
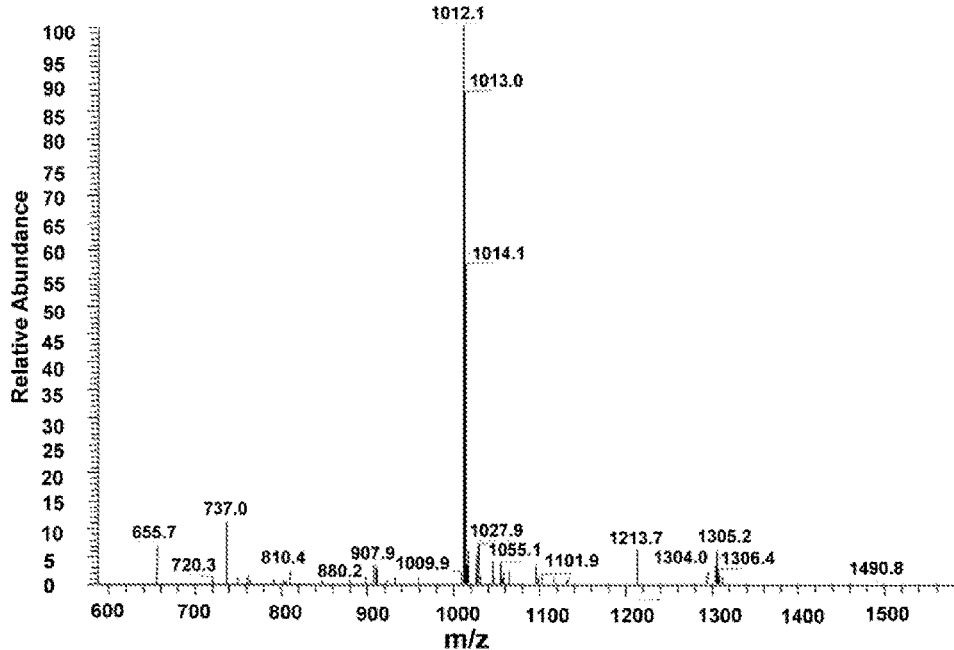

【Fig. 13】
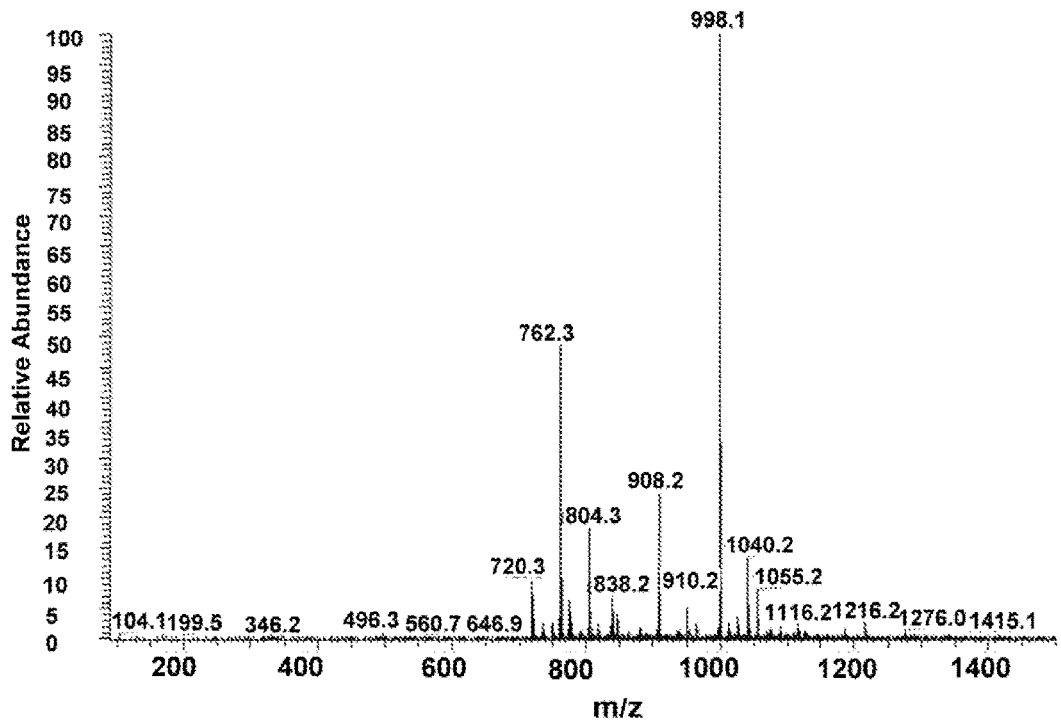
【Fig. 14】
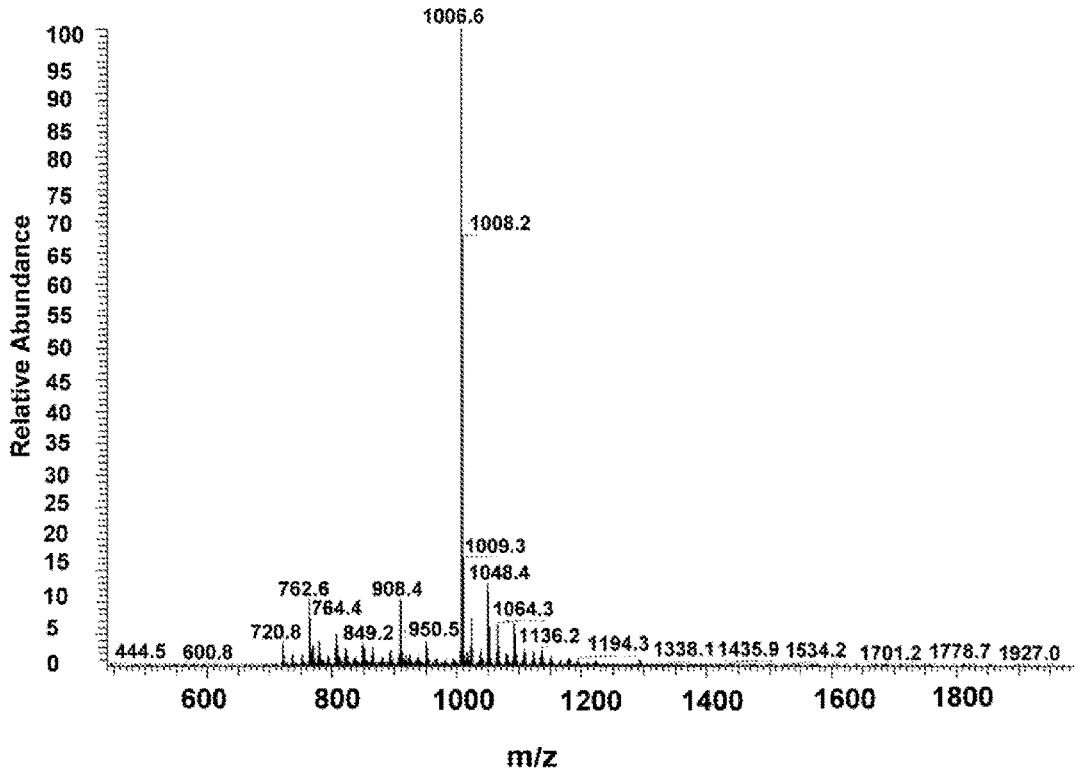

FULLERENE DERIVATIVE, ORGANIC SOLAR CELL USING SAME, AND MANUFACTURING METHOD THEREOF

This application is a National Stage Entry of International Application No. PCT/KR2014/003339, filed Apr. 17, 2014, and which claims the benefit of priority of Korean Application No. 10-2013-0042114, filed Apr. 17, 2013, both of which are incorporated by reference in their entirety for all purposes as if fully set forth herein.

TECHNICAL FIELD

The present specification relates to a fullerene derivative, an organic solar cell using the same, and a fabricating method thereof.

This application claims priority to and the benefits of Korean Patent Application No. 10-2013-0042114, filed with the Korean Intellectual Property Office on Apr. 17, 2013, the entire contents of which are incorporated herein by reference.

BACKGROUND ART

Solar cells using organic materials have received attention with advantages such as simple processability, diversity, inexpensive manufacturing costs and high flexibility, and have rapidly grown with the development of new materials.

Based on inexpensive costs and availability in a manufacturing process, which are the biggest advantages of organic materials, organic semiconductors are expected to appear as a core material in the manufacture of low-priced solar cells such as thin film-type devices, large area devices, flexible devices for which a roll-to-roll method may be used.

The possibility of an organic solar cell was first presented in 1970s, but the organic solar cell had no practical use since the efficiency was too low.

However, since C. W. Tang of Eastman Kodak showed the possibility of commercialization as various solar cells with a double layer structure using copper phthalocyanine (CuPc) and a perylene tetracarboxylic acid derivative in 1986, interests in organic solar cells and related researches have rapidly increased brining in a lot of progresses.

Since then, organic solar cells have made innovative progresses in terms of efficiency as the concept of a bulk heterojunction (BHJ) was introduced by Yu et al. in 1995, and fullerene derivatives of which solubility is improved such as PCBM have been developed as an n-type semiconductor material.

However, fullerene, a starting material, does not have favorable solubility thereby has low reactivity, and as a result, has a problem in that the costs of the fullerene derivatives increase due to the low yield when synthesized.

Meanwhile, the development of electron donor materials having a low bandgap and electron acceptor materials having favorable charge mobility has been continuously attempted in order to replace existing materials.

DISCLOSURE

Technical Problem

An objective of the present specification is to provide a fullerene derivative having high solubility and high electron mobility, an organic solar cell including the same, and a fabricating method thereof.

Technical Solution

One embodiment of the present specification provides a fullerene derivative represented by the following Chemical Formula 1.

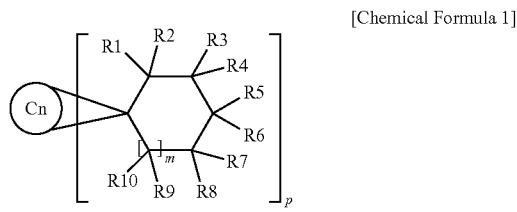

[Chemical Formula 1]

Wherein, m is an integer of 0 or 1, p is an integer of 1 to 3, when p is 2 or greater, the structures within the parenthesis are the same as or different from each other, Cn is fullerene of $C_{60}$ to $C_{84}$, R1 to R10 are the same as or different from each other, and each independently hydrogen; deuterium; a halogen group; a nitrile group; a nitro group; an imide group; an amide group; a hydroxyl group; an ester group; a carbonyl group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heteroring group that includes one or more of N, O and S atoms, or adjacent substituents are bonded to each other to form a substituted or unsubstituted hydrocarbon ring; a substituted or unsubstituted heteroring that includes one or more of N, O and S atoms, or substituents within the same carbon form a spiro bond; a carbonyl group; a substituted or unsubstituted imine group; or a substituted or unsubstituted alkenyl group, when m is 0, at least one of the substituents of the ring formed by the adjacent substituents of R1 to R8; and R1 to R8 is -(L)a-(M)b;

when m is 1, at least one of the substituents of the ring formed by the adjacent substituents of R1 to R10; and R1 to R10; is -(L)a-(M)b;

a is an integer of 0 or 1, b is an integer of 1 or 2,

L is a substituted or unsubstituted alkylene group having 1 to 20 carbon atoms; a substituted or unsubstituted divalent ether group having 1 to 20 carbon atoms; a substituted or unsubstituted divalent aromatic hydrocarbon ring having 5 to 30 carbon atoms; or a divalent aromatic heteroring that includes one or more of N, O and S atoms, M is

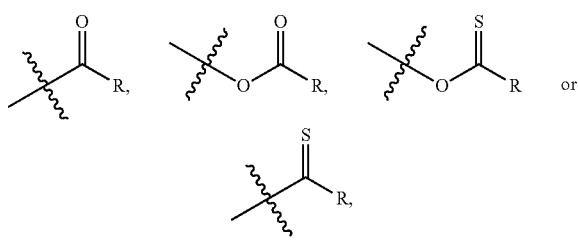

and

R is hydrogen; deuterium; a halogen group; a nitrile group; a nitro group; an imide group; an amide group; a hydroxyl group; an ester group; a carbonyl group; a substituted or unsubstituted alkyl group; a substituted or unsubstituted cycloalkyl group; a substituted or unsubstituted alkoxy group; a substituted or unsubstituted cycloalkoxy group; a substituted or unsubstituted arylalkyl group; a substituted or unsubstituted arylalkyloxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted silyloxy group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; a substituted or unsubstituted heteroaryl group that includes one or more of N, O and S atoms; or a substituted or unsubstituted heteroaryloxy group that includes one or more of N, O and S atoms.

One embodiment of the present specification provides an organic solar cell including a first electrode, a second electrode provided opposite to the first electrode, and one or more organic material layers provided between the first electrode and the second electrode, wherein one or more layers of the organic material layers include the fullerene derivative.

In addition, one embodiment of the present specification provides a method for fabricating an organic solar cell, which includes the steps of preparing a substrate; forming a first electrode on top of the substrate; forming one or more organic material layers including a photoactive layer on top of the first electrode; and forming a second electrode on top of the organic material layers, wherein one or more layers of the organic material layers include the fullerene derivative represented by Chemical Formula 1.

Advantageous Effects

An organic solar cell including a fullerene derivative according to one embodiment of the present specification shows efficiency enhancement and/or safety enhancement.

A fullerene derivative according to one embodiment of the present specification can be used either alone or as a mixture with impurities in an organic solar cell, and a vacuum deposition method, a solution coating method or the like may be applied.

A fullerene derivative according to one embodiment of the present specification can improve photoefficiency.

DESCRIPTION OF DRAWINGS

FIG. 1 shows an organic solar cell according to one embodiment by a diagram.

FIG. 2 is a diagram showing an MS spectrum of a fullerene derivative represented by Chemical Formula 1-2-2.

FIG. 3 is a diagram showing an MS spectrum of a fullerene derivative represented by Chemical Formula 1-1-1.

FIG. 4 is a diagram showing an MS spectrum after purifying p=1 in a fullerene derivative represented by Chemical Formula 1-1-1.

FIG. 5 is a diagram showing liquid chromatography (HPLC) after purifying p=1 in a fullerene derivative represented by Chemical Formula 1-1-1.

FIG. 6 is a diagram showing an MS spectrum of a fullerene derivative represented by Chemical Formula 1-1-36.

FIG. 7 is a diagram showing liquid chromatography (HPLC) of a fullerene derivative represented by Chemical Formula 1-1-36.

FIG. 8 is a diagram showing an NMR graph of a fullerene derivative represented by Chemical Formula 1-1-36.

FIG. 9 is a diagram showing an MS spectrum of a fullerene derivative represented by Chemical Formula 1-1-2.

FIG. 10 is a diagram showing an MS spectrum after purifying p=1 in a fullerene derivative represented by Chemical Formula 1-1-12.

FIG. 11 is a diagram showing an MS spectrum after purifying p=2 in the fullerene derivative represented by Chemical Formula 1-1-12.

FIG. 12 is a diagram showing an MS spectrum of a fullerene derivative represented by Chemical Formula 1-1-15.

FIG. 13 is a diagram showing an MS spectrum of a fullerene derivative represented by Chemical Formula 1-1-44.

FIG. 14 is a diagram showing an MS spectrum of a fullerene derivative represented by Chemical Formula 1-1-21.

REFERENCE NUMBER

101: Substrate
102: First Electrode
103: Hole Transfer Layer
104: Photoactive Layer
105: Second Electrode

MODE FOR INVENTION

Hereinafter, the present specification will be described in detail.

One embodiment of the present specification provides the fullerene derivative represented by Chemical Formula 1.

In the fullerene derivative according to one embodiment of the present specification, when m is 0, at least one of the substituents of the ring formed by the adjacent substituents of R1 to R8; and R1 to R8 is -(L)a-(M)b; and when m is 1, at least one of the substituents of the ring formed by the adjacent substituents of R1 to R10; and R1 to R10; is -(L)a-(M)b.

L is a substituted or unsubstituted alkylene group having 1 to 20 carbon atoms; a substituted or unsubstituted divalent ether group having 1 to 20 carbon atoms; a substituted or unsubstituted divalent aromatic hydrocarbon ring having 5 to 30 carbon atoms; or a divalent aromatic heteroring that includes one or more of N, O and S atoms, M is

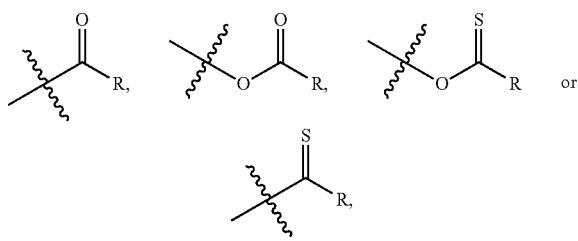

and R is the same as defined above.

The fullerene derivative including substituents represented by -(L)a-(M)b has an advantage in that the fullerene derivative is readily used in a solution process due to its increased solubility. In addition, the fullerene derivative is effective in enhancing the efficiency of a device by forming excellent morphology thereby improving electron mobility.

In one embodiment of the present specification, R is a substituted or unsubstituted alkyl group having 1 to 20 carbon atoms; a substituted or unsubstituted alkoxy group having 1 to 20 carbon atoms; a substituted or unsubstituted cycloalkyl group having 3 to 60 carbon atoms; a substituted or unsubstituted cycloalkoxy group having 3 to 60 carbon atoms; a substituted or unsubstituted arylalkoxy group having 7 to 50 carbon atoms; a substituted or unsubstituted aryl group having 6 to 60 carbon atoms; a substituted or unsubstituted aryloxy group having 6 to 60 carbon atoms; a substituted or unsubstituted heteroaryl group having 2 to 60 carbon atoms, which includes one or more of N, O and S atoms; or a substituted or unsubstituted heteroaryloxy group having 2 to 60 carbon atoms, which includes one or more of N, O and S atoms.

In one embodiment of the present specification, R is a linear, branched or cyclic substituted or unsubstituted alkyl group having 1 to 25 carbon atoms.

In one embodiment of the present specification, Rs are the same as or different from each other, and each independently a linear, branched or cyclic substituted or unsubstituted alkoxy group having 1 to 25 carbon atoms.

In one embodiment of the present specification, Rs are the same as or different from each other, and each independently a linear, branched or cyclic fluorine (F)-substituted alkyl group having 1 to 25 carbon atoms.

In one embodiment of the present specification, Rs are the same as or different from each other, and each independently a linear, branched or cyclic fluorine (F)-substituted alkoxy group having 1 to 25 carbon atoms.

In one embodiment of the present specification, Rs are the same as or different from each other, and each independently an alkoxy group substituted with a cycloether group.

In one embodiment of the present specification, Rs are the same as or different from each other, and each independently a linear, branched or cyclic substituted or unsubstituted alkylamine group having 1 to 25 carbon atoms.

In one embodiment of the present specification, Rs are the same as or different from each other, and each independently a substituted or unsubstituted arylamine group having 5 to 30 carbon atoms.

In one embodiment of the present specification, Rs are the same as or different from each other, and each independently a substituted or unsubstituted aryl group having 5 to 30 carbon atoms.

In one embodiment of the present specification, Rs are the same as or different from each other, and each independently a substituted or unsubstituted aryloxy group having 5 to 30 carbon atoms.

In one embodiment of the present specification, Rs are the same as or different from each other, and each independently a heteroaryl group that includes one or more of N, O and S atoms.

In one embodiment of the present specification, Rs are the same as or different from each other, and each independently a heteroaryloxy group that includes one or more of N, O and S atoms.

In one embodiment of the present specification, Rs are the same as or different from each other, and each independently a hydroxyl group.

The fullerene derivative in which R is a linear, branched or cyclic substituted or unsubstituted alkyl group having 1 to 25 carbon atoms is effective in that the fullerene derivative has high solubility.

The fullerene derivative in which R is a linear, branched or cyclic substituted or unsubstituted alkoxy group having 1 to 25 carbon atoms is effective in that the fullerene derivative has high solubility.

The fullerene derivative in which R is a linear, branched or cyclic fluorine (F)-substituted alkyl group having 1 to 25 carbon atoms is effective in that the fullerene derivative has high solubility.

The fullerene derivative in which R is a linear, branched or cyclic fluorine (F)-substituted alkoxy group having 1 to 25 carbon atoms is effective in that the fullerene derivative has high solubility.

In one embodiment of the present specification, at least two adjacent substituents of R1 to R10 are bonded to each other to form a substituted or unsubstituted hydrocarbon ring; or a substituted or unsubstituted heteroring that includes one or more of N, O and S atoms.

When the adjacent substituents are bonded to each other to form an aromatic ring or aromatic heterring, it is effective in increasing the mobility of charges due to the π-π interactions between the aromatic rings or aromatic heterorings within the electron donor material and the molecule.

In one embodiment of the present specification, R1 or R2 and R3 or R4 form a 5-membered or 6-membered aromatic ring.

In one embodiment of the present specification, R1 or R2 and R3 or R4 form a 5-membered or 6-membered aromatic heteroring.

In one embodiment of the present specification, R3 or R4 and R5 or R6 form a 5-membered or 6-membered aromatic ring.

In one embodiment of the present specification, R3 or R4 and R5 or R6 form a 5-membered or 6-membered aromatic heteroring.

In one embodiment of the present specification, the fullerene derivative represented by Chemical Formula 1 is a fullerene derivative represented by any one of the following Chemical Formula 2 to the following Chemical Formula 5.

[Chemical Formula 2]

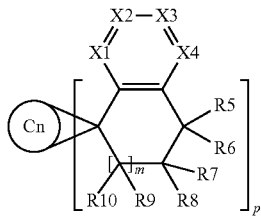

[Chemical Formula 3]

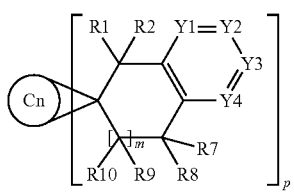

[Chemical Formula 4]

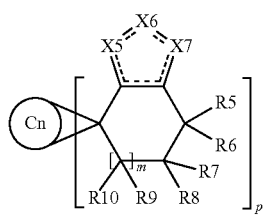

[Chemical Formula 5]

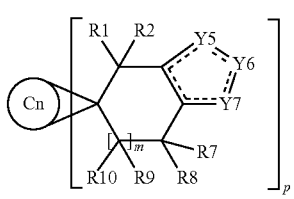

wherein, Cn, m, p, and R1 to R10 are the same as those defined in Chemical Formula 1, X1 to X4 are the same as or different from each other, and each independently CRx; or N, Y1 to Y4 are the same as or different from each other, and each independently CRy; or N, X5 to X7 are the same as or different from each other, and each independently CRx'; S; or NRx', Y5 to Y7 are the same as or different from each other, and each independently Cry'; S; or NRy', and Rx, Ry, Rx' and Ry' are the same as or different from each other, and each independently hydrogen; deuterium; a halogen group; a nitrile group; a nitro group; an imide group; an amide group; a hydroxyl group; an ester group; a carbonyl group; a substituted or unsubstituted alkyl group; a substituted or unsubstituted cycloalkyl group; a substituted or unsubstituted alkoxy group; a substituted or unsubstituted cycloalkoxy group; a substituted or unsubstituted arylalkyl group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heteroring group that includes one or more of N, O and S atoms, or adjacent substituents are bonded to each other to form a substituted or unsubstituted hydrocarbon ring; or a heteroring that includes one or more of N, O and S atoms, or a spiro bond.

In the present specification,

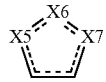

of Chemical Formula 5 and

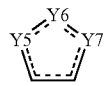

of Chemical Formula 6 mean a state in which a conjugation is formed.

In the present specification,

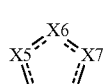

of Chemical Formula 5 may be specifically

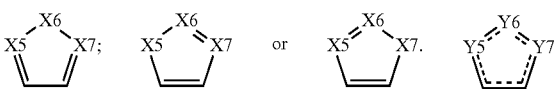

of Chemical Formula 6 may be specifically

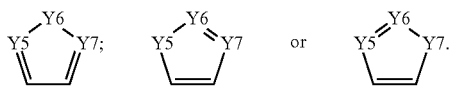

Examples of the substituents are described below, however, the substituents are not limited thereto.

In the present specification, the term "substituted or unsubstituted" means being substituted with one or more substituents selected from the group consisting of deuterium; a halogen group; an alkyl group; an alkenyl group; an alkoxy group; an ester group; a carbonyl group; a carboxyl group; a hydroxyl group; a cycloalkyl group; a silyl group; an arylalkenyl group; an aryloxy group; an alkylthioxy group; an alkylsulfoxy group; an arylsulfoxy group; a boron group; an alkylamine group; an aralkylamine group; an arylamine group; a heteroaryl group; a carbazole group; an arylamine group; an aryl group; a fluorenyl group; a nitrile group; a nitro group; a hydroxyl group; and a heteroring group that includes one or more of N, O and S atoms, or having no substituents.

In the present invention, the halogen group may include fluorine, chlorine, bromine or iodine.

In the present specification, the imide group may be represented by

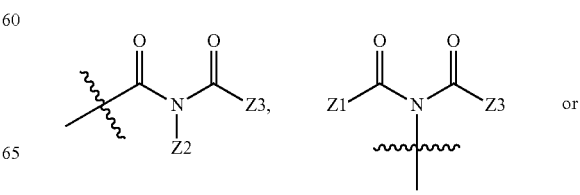

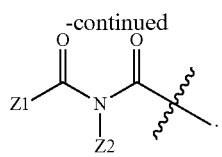

Z1 to Z3 are the same as or different from each other, and are hydrogen; a linear, branched or cyclic substituted or unsubstituted alkyl group having 1 to 25 carbon atoms; or a substituted or unsubstituted aryl group having 6 to 25 carbon atoms. Specifically, Z1 to Z3 are the same as or different from each other, and are a linear, branched or cyclic substituted or unsubstituted alkyl group having 6 to 25 carbon atoms; or a substituted or unsubstituted aryl group having 6 to 25 carbon atoms.

In the present specification, the amide group may be represented by

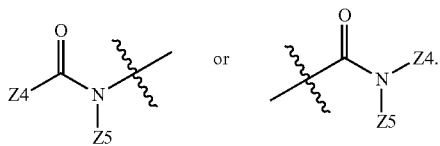

Z4 and Z5 are the same as or different from each other, and each independently hydrogen; a substituted or unsubstituted alkyl group having 1 to 20 carbon atoms; a substituted or unsubstituted cycloalkyl group having 3 to 60 carbon atoms; a substituted or unsubstituted arylalkyl group having 7 to 50 carbon atoms; a substituted or unsubstituted aryl group having 6 to 60 carbon atoms; or a substituted or unsubstituted heteroring group having 2 to 60 carbon atoms, which includes one or more of N, O and S atoms.

In the present specification, a general formula of the ester group may be represented by

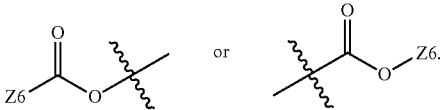

Z6 is hydrogen; a substituted or unsubstituted alkyl group having 1 to 20 carbon atoms; a substituted or unsubstituted cycloalkyl group having 3 to 60 carbon atoms; a substituted or unsubstituted arylalkyl group having 7 to 50 carbon atoms; a substituted or unsubstituted aryl group having 6 to 60 carbon atoms; or a substituted or unsubstituted heteroring group having 2 to 60 carbon atoms, which includes one or more of N, O and S atoms.

In the present specification, the ether group may be represented by

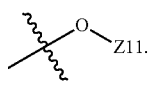

Z11 is a linear, branched or cyclic substituted or unsubstituted alkyl group having 1 to 25 carbon atoms; or a substituted or unsubstituted aryl group having 6 to 25 carbon atoms. Specifically, Z11 is the same as or different from each other, and is a linear, branched or cyclic substituted or unsubstituted alkyl group having 6 to 25 carbon atoms; or a substituted or unsubstituted aryl group having 6 to 25 carbon atoms.

In one embodiment of the present specification, the ether group is an alkylether group.

In the present specification, the alkyl group may be linear or branched, and the number of carbon atoms, although not particularly limited, is preferably 1 to 20. Specific examples thereof include a methyl group, an ethyl group, a propyl group, an isopropyl group, a butyl group, a t-butyl group, a pentyl group, a hexyl group, a heptyl group and the like, but are not limited thereto.

In the present specification, the cycloalkyl group is not particularly limited, but preferably has 3 to 60 atoms, and specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the cyclo in the cycloalkoxy group may be selected from among the examples of the cycloalkyl group described above.

In the present specification, the alkoxy group may be linear, branched or cyclic. The number of carbon atoms in the alkoxy group is not particularly limited, but is preferably 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto In the present specification, the number of carbon atoms in the arylalkyl group is not particularly limited, however, in one embodiment of the present specification, the number of carbon atoms in the arylalkyl group is 7 to 50. Specifically, the aryl part has 6 to 49 carbon atoms, and the alkyl part has 1 to 44 carbon atoms. Specific examples thereof include a benzyl group, a p-methylbenzyl group, a m-methylbenzyl group, a p-ethylbenzyl group, a m-ethylbenzyl group, a 3,5-dimethylbenzyl group, an α-methylbenzyl group, an α,α-dimethylbenzyl group, an α,α-methylphenylbenzyl group, a 1-naphthylbenzyl group, an 2-naphthylbenzyl group, a p-fluorobenzyl group, a 3,5-difluorobenzyl group, an α,α-ditrifluoromethylbenzyl group, a p-methoxybenzyl group, a m-methoxybenzyl group, an α-phenoxybenzyl group, an α-benzyloxybenzyl group, a naphthylmethyl group, a naphthylethyl group, a naphthylisopropyl group, a pyrrolylmethyl group, a pyrrolylethyl group, an aminobenzyl group, a nitrobenzyl group, a cyanobenzyl group, a 1-hydroxy-2-phenylisopropyl group, a 1-chloro-2-phenylisopropyl group and the like, but are not limited thereto.

In the present specification, the arylalkyl in the arylalkyloxy group may be selected from among the examples of the arylalkyl group described above.

In the present specification, the alkenyl group may be linear or branched, and although not particularly limited, the number of carbon atoms is preferably 2 to 40. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the aryl group may be monocyclic, and, although not particularly limited, the number of carbon atoms is preferably 6 to 60. Specific examples of the aryl group include monocyclic aromatic such as a phenyl group, a biphenyl group, a triphenyl group, a terphenyl group and a stilbenyl group, and multicyclic aromatic such as a naphthyl group, an anthracenyl group, a phenanthryl group, a pyrenyl group, a perylenyl group, a tetracenyl group, a crycenyl group, a fluorenyl group, an acenaphthacenyl group, a triphenylene group and a fluoranthene group, but the examples are not limited thereto.

In the present specification, the aromatic ring group may be selected from among the examples of the aryl group, but is not limited thereto.

In the present specification, the aryl in the aryloxy group may be selected from among the examples of the aryl group described above.

In the present specification, the heteroring group or the heteroaryl group is a heteroring group that includes O, N or S as a heteroatom, and, although not particularly limited, the number of carbon atoms is preferably 2 to 60. Examples of the heteroring group include a thiophene group, a furan group, a pyrrole group, an imidazole group, a thiazole group, an oxazole group, an oxadiazole group, a triazole group, a pyridyl group, a bipyridyl group, a triazine group, an acridyl group, a pyridazine group, a qinolinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a dibenzofuranyl group and the like, but are not limited thereto.

In the present specification, the heteroaryl in the heteroaryloxy group may be selected from among the examples of the heteroaryl group described above. In the present specification, the aryl group in the aryloxy group, the arylthioxy group, the arylsulfoxy group and the aralkylamine group is the same as the examples of the aryl group described above. Specific examples of the aryloxy group include phenoxy, p-tolyloxy, m-tolyloxy, 3,5-dimethylphenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy and the like, and examples of the arylthioxy group include a phenylthioxy group, a 2-methylphenylthioxy group, a 4-tert-butylphenylthioxy group and the like, and examples of the arylsulfoxy group include a benzenesulfoxy group, a p-toluenesulfoxy group and the like, but the examples are not limited thereto.

In the present specification, the alkyl group in the alkylthioxy group, the alkylsulfoxy group, the alkylamine group and the aralkylamine group is the same as the examples of the alkyl group described above. Specific examples of the alkylthioxy group include a methylthioxy group, an ethylthioxy group, a tert-butylthioxy group, a hexylthioxy group, an octylthioxy group and the like, and examples of the alkylsulfoxy group include a methylsulfoxy group, an ethylsulfoxy group, a propylsulfoxy group, a butylsulfoxy group and the like, but the examples are not limited thereto.

The fluorenyl group in the present specification includes the structure of an open fluorenyl group, and herein, the open fluorenyl group has a structure in which the linkage of one cyclic compound is broken in the structure of two cyclic organic compounds linked through one atom.

When the fluorenyl group is substituted, examples thereof may include

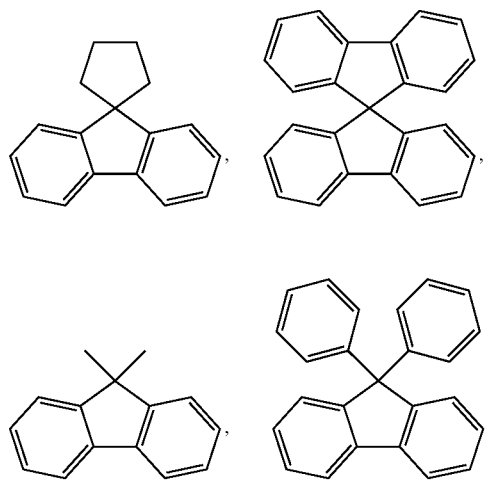

and the like. However, the examples are not limited thereto.

In the present specification, the number of carbon atoms in the amine group is not particularly limited, but is preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group and the like, but are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include a monocyclic aryl group, a multicyclic aryl group, or a monocyclic aryl group and a multicyclic aryl group at the same time.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, a carbozoland a triphenylamine group and the like, but are not limited thereto.

In the present specification, the heteroaryl group in the heteroarylamine group may be selected from among the examples of the heteroring group described above.

In the present specification, the alkylene group means having two binding sites in the alkyl group, that is, a divalent group. Descriptions for the alkyl group shown above may be applied except that the alkenyl group is a divalent group.

In the present specification,

means a site that binds to other substituents or binding sites.

Adjacent substituents in the present specification mean substituents that substitute neighboring carbons such as R1 or R2 and R3 or R4; R3 or R4 and R5 or R6; R5 or R6 and R7 or R8; and R7 or R8 and R9 or R10.

Adjacent groups forming a hydrocarbon ring or heteroring in the present specification mean adjacent substituents forming a bond in order to form a 5-membered to 7-membered hydrocarbon ring or heteroring, and the heteroring may include one or more of N, O, and S.

The hydrocarbon ring in the present specification includes all of a cycloalkyl group; a cycloalkenyl group; an aromatic ring group; or an aliphatic ring group, may be monocyclic or multicyclic, and includes a fused ring in which one, two or more of these are bonded.

The formed heteroring in the present specification means that at least one carbon atom in the hydrocarbon ring is substituted with an N, O, or S atom, and the formed heteroring may be an aliphatic ring or an aromatic ring, and may be monocyclic or multicyclic.

In one embodiment of the present specification, at least 2 adjacent substituents of R1 to R10 are bonded to each other to form a substituted or unsubstituted aromatic hydrocarbon ring; or a substituted or unsubstituted aromatic heteroring that includes one or more of N, O and S atoms.

The cycloalkyl, the cycloalkenyl, the aromatic ring, the aliphatic heteroring, and the aromatic heteroring may be monocyclic or multicyclic.

In the present specification, the substituents of the same carbon mean substituents sharing one carbon, such as R1 and R2; R3 and R4; R5 and R6; R7 and R8; or R9 and R10.

In one embodiment of the present specification, the substituents of the same carbon form a double bond. Examples thereof include a carbonyl group; a substituted or unsubstituted imine group, but are not limited thereto.

In the present specification, the substituents of the same carbon form a spiro bond. The spiro bond means a structure in which two cyclic organic compounds are linked to one atom, and may include a structure in which the linkage of one cyclic compound is broken in the structure of two cyclic organic compounds linked through one atom.

For example, the spiro bond means forming a 5-membered to 7-membered aliphatic hydrocarbon ring, a 5-membered to 7-membered aromatic hydrocarbon ring, a 5-membered to 7-membered aliphatic heteroring that includes one or more of O, N and S as a heteroatom, a 5-membered to 7-membered aromatic heteroring that includes one or more of O, N and S as a heteroatom by the substituents of R1 and R2; R3 and R4; R5 and R6; R7 and R8; or R9 and R10, which share one carbon, forming a bond.

In one embodiment of the present specification, m is 0.
In one embodiment of the present specification, m is 1.
In one embodiment of the present specification, Cn is $C_{60}$.
The size of Cn may be selected depending on the needs of those skilled in the art.

In one embodiment of the present specification, at least one of the substituents of the hydrocarbon ring formed by the adjacent substituents of R1 to R10; and R5 to R8 is -(L)a-(M)b, and L, a, M and b are the same as described above.

In one embodiment of the present specification, p is 1.
In one embodiment of the present specification, p is 2.
In one embodiment of the present specification, when p is 2 or greater, the structures in the parenthesis are the same as or different from each other.

In one embodiment of the present specification, R1 is hydrogen.
In one embodiment of the present specification, R2 is hydrogen.
In one embodiment of the present specification, R3 is hydrogen.
In one embodiment of the present specification, R4 is hydrogen.
In one embodiment of the present specification, R5 is hydrogen.
In one embodiment of the present specification, R5 is -(L)a-(M)b.
In one embodiment of the present specification, R5 is -(L)a-(M)b, a is 0, b is 1, and M is

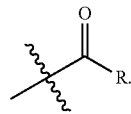

In one embodiment of the present specification, R5 is -(L)a-(M)b, a is 1, b is 1, and M is

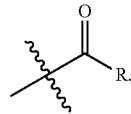

In one embodiment of the present specification, R5 is -(L)a-(M)b, a is 1, b is 1, and M is

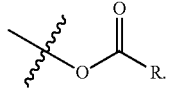

In one embodiment of the present specification, R5 is -(L)a-(M)b, a is 1, b is 1, and M is

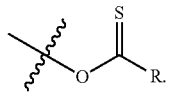

In another embodiment, R5 is -(L)a-(M)b, a is 0, b is 1, and M is

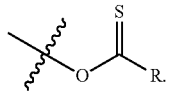

In one embodiment of the present specification, R5 is -(L)a-(M)b, a is 0, b is 1, and M is

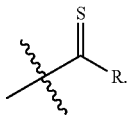

In one embodiment of the present specification, R5 is -(L)a-(M)b, a is 1, b is 1, and M is

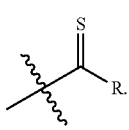

In one embodiment of the present specification, R6 is -(L)a-(M)b.

In one embodiment of the present specification, R6 is -(L)a-(M)b, a is 0, b is 1, and M is

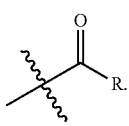

In one embodiment of the present specification, R6 is -(L)a-(M)b, a is 1, b is 1, and M is

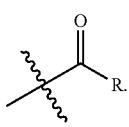

In one embodiment of the present specification, R6 is -(L)a-(M)b, a is 1, b is 1, and M is

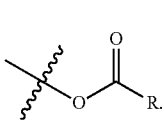

In one embodiment of the present specification, R6 is -(L)a-(M)b, a is 1, b is 1, and M is

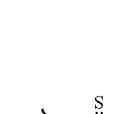

In another embodiment, R6 is -(L)a-(M)b, a is 0, b is 1, and M is

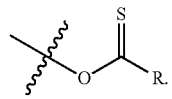

In one embodiment of the present specification, R6 is -(L)a-(M)b, a is 0, b is 1, and M is

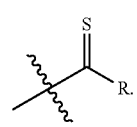

In one embodiment of the present specification, R6 is -(L)a-(M)b, a is 1, b is 1, and M is

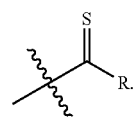

In one embodiment of the present specification, R6 is hydrogen.

In one embodiment of the present specification, R7 is hydrogen.

In one embodiment of the present specification, R7 is -(L)a-(M)b.

In one embodiment of the present specification, R7 is -(L)a-(M)b, a is 0, b is 1, and M is

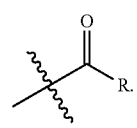

In one embodiment of the present specification, R7 is -(L)a-(M)b, a is 1, b is 1, and M is

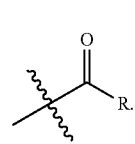

In one embodiment of the present specification, R7 is -(L)a-(M)b, a is 1, b is 1, and M is

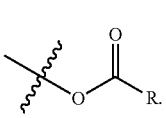

In one embodiment of the present specification, R7 is -(L)a-(M)b, a is 1, b is 1, and M is

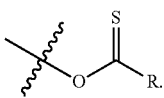

In another embodiment, R7 is -(L)a-(M)b, a is 0, b is 1, and M is

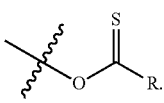

In one embodiment of the present specification, R7 is -(L)a-(M)b, a is 0, b is 1, and M is

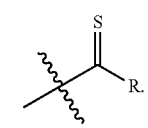

In one embodiment of the present specification, R7 is -(L)a-(M)b, a is 1, b is 1, and M is

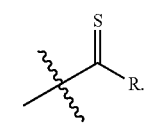

In one embodiment of the present specification, R8 is hydrogen.
In one embodiment of the present specification, R8 is -(L)a-(M)b.
In one embodiment of the present specification, R8 is -(L)a-(M)b, a is 0, b is 1, and M is

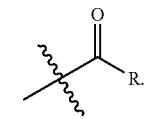

In one embodiment of the present specification, R8 is -(L)a-(M)b, a is 1, b is 1, and M is

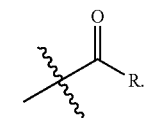

In one embodiment of the present specification, R8 is -(L)a-(M)b, a is 1, b is 1, and M is

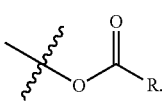

In one embodiment of the present specification, R8 is -(L)a-(M)b, a is 1, b is 1, and M is

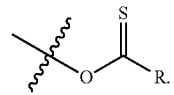

In another embodiment, R8 is -(L)a-(M)b, a is 0, b is 1, and M is

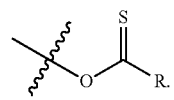

In one embodiment of the present specification, R8 is -(L)a-(M)b, a is 0, b is 1, and M is

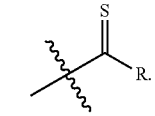

In one embodiment of the present specification, R8 is -(L)a-(M)b, a is 1, b is 1, and M is

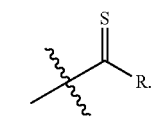

In one embodiment of the present specification, R1 or R2 and R3 or R4 form a 5-membered or 6-membered aromatic ring.
In one embodiment of the present specification, R1 or R2 and R3 or R4 form a 5-membered or 6-membered aromatic ring, and the substituent of the formed aromatic ring is hydrogen.
In one embodiment of the present specification, R1 or R2 and R3 or R4 form a 5-membered or 6-membered aromatic ring, and the substituent of the formed aromatic is -(L)a-(M)b.
In one embodiment of the present specification, L is a substituted or unsubstituted alkylene group having 1 to 20 carbon atoms; or a substituted or unsubstituted divalent aromatic hydrocarbon ring having 5 to 30 carbon atoms.
In one embodiment of the present specification, L is a substituted or unsubstituted alkylene group.
In one embodiment of the present specification, L is a methylene group.
In one embodiment, L is an ethylene group.
In another embodiment, L is a substituted or unsubstituted propylene group.
In one embodiment of the present specification, L is a propylene group substituted with methyl acetate.
In one embodiment of the present specification, L is a substituted or unsubstituted divalent aromatic hydrocarbon ring having 5 to 30 carbon atoms.
In one embodiment of the present specification, L is a phenylene group.

In one embodiment of the present specification, a is an integer of 0 or 1, L is a substituted or unsubstituted alkylene group having 1 to 4 carbon atoms; or a substituted or unsubstituted phenylene group.

In another embodiment, R is a substituted or unsubstituted alkyl group having 1 to 20 carbon atoms; a substituted or unsubstituted alkoxy group having 1 to 20 carbon atoms; a substituted or unsubstituted cycloalkyl group having 3 to 60 carbon atoms; a substituted or unsubstituted cycloalkoxy group having 3 to 60 carbon atoms; a substituted or unsubstituted arylalkoxy group having 7 to 50 carbon atoms; a substituted or unsubstituted aryl group having 6 to 60 carbon atoms; a substituted or unsubstituted aryloxy group having 6 to 60 carbon atoms; a substituted or unsubstituted heteroaryl group having 2 to 60 carbon atoms, which includes one or more of N, O and S atoms; or a substituted or unsubstituted heteroaryloxy group having 2 to 60 carbon atoms, which includes one or more of N, O and S atoms.

In another embodiment, R is a substituted or unsubstituted alkyl group having 1 to 20 carbon atoms; a substituted or unsubstituted alkoxy group having 1 to 20 carbon atoms; a substituted or unsubstituted arylalkoxy group having 7 to 50 carbon atoms; a substituted or unsubstituted aryl group having 6 to 60 carbon atoms; or a substituted or unsubstituted heteroaryloxy group having 2 to 60 carbon atoms, which includes one or more of N, O and S atoms.

In one embodiment of the present specification, R is a substituted or unsubstituted alkoxy group having 1 to 20 carbon atoms; a substituted or unsubstituted arylalkoxy group having 7 to 50 carbon atoms; or a substituted or unsubstituted heteroaryloxy group having 2 to 60 carbon atoms, which includes one or more of N, O and S atoms.

In another embodiment, the alkoxy group, the arylalkoxy group and the heteroaryloxy group are unsubstituted or substituted with a halogen group; a cyano group; a substituted or unsubstituted aryl group having 6 to 30 carbon atoms; a substituted or unsubstituted arylamine group; or a substituted or unsubstituted heteroring group having 2 to 30 carbon atoms, which includes one or more of N, O and S atoms.

In one embodiment of the present specification, m is an integer of 0 or 1, at least one of the substituents of the hydrocarbon ring formed by the adjacent substituents of R1 to R10; and R5 to R8 is -(L)a-(M)b;

a is 0 or 1,

L is a substituted or unsubstituted alkylene group having 1 to 20 carbon atoms; or a substituted or unsubstituted divalent aromatic hydrocarbon ring having 5 to 30 carbon atoms, b is an integer of 1 or 2, M is

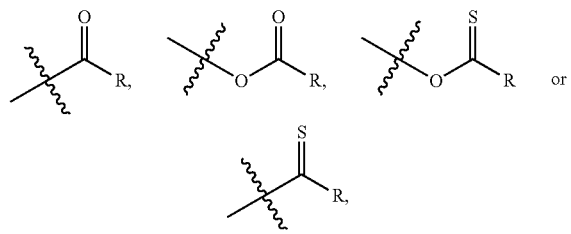

and

R is a substituted or unsubstituted alkyl group having 1 to 20 carbon atoms; a substituted or unsubstituted alkoxy group having 1 to 20 carbon atoms; a substituted or unsubstituted cycloalkyl group having 3 to 60 carbon atoms; a substituted or unsubstituted cycloalkoxy group having 3 to 60 carbon atoms; a substituted or unsubstituted arylalkoxy group having 7 to 50 carbon atoms; a substituted or unsubstituted aryl group having 6 to 60 carbon atoms; a substituted or unsubstituted aryloxy group having 6 to 60 carbon atoms; a substituted or unsubstituted heteroaryl group having 2 to 60 carbon atoms, which includes one or more of N, O and S atoms; or a substituted or unsubstituted heteroaryloxy group having 2 to 60 carbon atoms, which includes one or more of N, O and S atoms.

In one embodiment of the present specification, R is a substituted or unsubstituted alkoxy group.

In one embodiment of the present specification, R is an ethyloxy group.

In one embodiment of the present specification, R is a methyloxy group.

In another embodiment, R is an octoxy group.

In one embodiment of the present specification, R is a branched substituted or unsubstituted alkoxy group.

In one embodiment of the present specification, R is a 1-methylhexyloxy group.

In another embodiment, R is a 1-ethylpentyloxy group.

In another embodiment, R is a 2-ethylhexyloxy group.

In another embodiment, R is a 1-methylheptyloxy group.

In another embodiment, R is a 1-ethylhexyloxy group.

In one embodiment, R is a 2-ethylheptyloxy group.

In another embodiment, R is a 1-butyldodecanyloxy group.

In another embodiment, R is a 1-ethyldodecanyloxy group.

In another embodiment, R is a 2-butylheptyloxy group.

In another embodiment, R is a 1-pentylhexyloxy group.

In one embodiment of the present specification, R is a 2-ethylheptyloxy group.

In one embodiment of the present specification, R is an alkoxy group substituted with a halogen group.

In one embodiment of the present specification, R is an alkoxy group substituted with a fluorine group.

In one embodiment of the present specification, R is a heptafluoropropoxy group.

In one embodiment of the present specification, R is an alkoxy group substituted with a substituted or unsubstituted aryl group.

In one embodiment of the present specification, R is an alkoxy group substituted with a substituted or unsubstituted phenyl group.

In one embodiment of the present specification, R is an alkoxy group substituted with a phenyl group.

In one embodiment of the present specification, R is a methyloxy group substituted with a phenyl group.

In another embodiment, R is a propyloxy group substituted with a phenyl group.

In another embodiment, R is a 3-phenylpropyloxy group.

In one embodiment, R is a 3,3-diphenylpropyloxy group.

In another embodiment, R is an alkoxy group substituted with a phenyl group substituted with a halogen group.

In one embodiment, R is an alkoxy group substituted with a phenyl group substituted with bromine.

In another embodiment, R is an ethyloxy group substituted with a phenyl group substituted with bromine.

In one embodiment of the present specification, R is an alkoxy group substituted with a phenyl group substituted with an arylamine group.

In another embodiment, R is an ethyloxy group substituted with a phenyl group substituted with an amine group substituted with a phenyl group.

In one embodiment, R is an alkoxy group substituted with a phenyl group substituted with an arylamine group substituted with an alkyl group.

In another embodiment, R is an ethyloxy group substituted with a phenyl group substituted with an amine group substituted with a phenyl group substituted with a hexyl group.

In another embodiment, R is an alkoxy group substituted with a phenyl group substituted with a substituted or unsubstituted heteroring group.

In another embodiment, R is an alkoxy group substituted with a phenyl group substituted with a substituted or unsubstituted benzimidazole group.

In one embodiment of the present specification, R is an ethyloxy group substituted with a phenyl group substituted with a benzimidazole group unsubstituted or substituted with a phenyl group.

In another embodiment, R is an alkoxy group substituted with a phenyl group substituted with a substituted or unsubstituted thiophene group.

In another embodiment, R is an alkoxy group substituted with a phenyl group substituted with a substituted or unsubstituted bithiophene group.

In another embodiment, R is an alkoxy group substituted with a phenyl group substituted with a bithiophene group substituted with a rhodanine group.

In another embodiment, R is an ethyloxy group substituted with a phenyl group substituted with a bithiophene group substituted with a rhodanine group.

In one embodiment of the present specification, R is an alkoxy group substituted with a substituted or unsubstituted biphenyl group.

In one embodiment, R is an alkoxy group substituted with a biphenyl group.

In another embodiment, R is an ethyloxy group substituted with a biphenyl group.

In one embodiment, R is an alkoxy group substituted with a biphenyl group substituted with a cyano group.

In one embodiment, R is an ethyloxy group substituted with a biphenyl group substituted with a cyano group.

In one embodiment, R is an alkoxy group substituted with a biphenyl group substituted with an alkyl group.

In another embodiment, R is an alkoxy group substituted with a biphenyl group substituted with a hexyl group.

In another embodiment, R is an ethyloxy group substituted with a biphenyl group substituted with a hexyl group.

In another embodiment, R is an alkoxy group substituted with a biphenyl group substituted with a substituted or unsubstituted heteroring group.

In another embodiment, R is an alkoxy group substituted with a biphenyl group substituted with a substituted or unsubstituted benzimidazole group.

In one embodiment of the present specification, R is an ethyloxy group substituted with a biphenyl group substituted with a benzimidazole group unsubstituted or substituted with a phenyl group.

In one embodiment, R is an alkoxy group substituted with a substituted or unsubstituted naphthyl group.

In another embodiment, R is an alkoxy group substituted with a naphthyl group.

In one embodiment, R is an ethyloxy group substituted with a naphthyl group.

In one embodiment of the present specification, R is an alkoxy group substituted with a substituted or unsubstituted pyrene group.

In another embodiment, R is an alkoxy group substituted with a pyrene group.

In another embodiment, R is an ethyloxy group substituted with a pyrene group.

In one embodiment of the present specification, R is an alkoxy group substituted with a substituted or unsubstituted fluorenyl group.

In one embodiment, R is an alkoxy group substituted with a fluorenyl group substituted with an alkyl group.

In one embodiment, R is an ethyloxy group substituted with a fluorenyl group substituted with a hexyl group.

In one embodiment of the present specification, R is an alkoxy group substituted with a substituted or unsubstituted heteroring group that includes one or more of N, O, and S atoms.

In one embodiment of the present specification, R is an alkoxy group substituted with a substituted or unsubstituted heteroring group that includes an S atom.

In another embodiment, R is an alkoxy group substituted with a substituted or unsubstituted thiophene group.

In one embodiment of the present specification, R is an alkoxy group substituted with a thiophene group substituted with an aryl group.

In one embodiment, R is an alkoxy group substituted with a thiophene group substituted with a phenyl group.

In another embodiment, R is an ethyloxy group substituted with a thiophene group substituted with a phenyl group.

In one embodiment, R is an alkoxy group substituted with a thiophene group substituted with a heteroring group.

In another embodiment, R is an alkoxy group substituted with a thiophene group substituted with a benzothiadiazole group.

In one embodiment, R is an alkoxy group substituted with a thiophene group substituted with a benzothiadiazole group substituted with a 2-hexylthiophene group.

In one embodiment, R is an ethyloxy group substituted with a thiophene group substituted with a benzothiadiazole group substituted with a 2-hexylthiophene group.

In another embodiment, R is an alkoxy group substituted with a substituted or unsubstituted bithiophene group.

In another embodiment, R is an alkoxy group substituted with a bithiophene group substituted with a rhodanine group.

In another embodiment, R is an ethyloxy group substituted with a bithiophene group substituted with a rhodanine group.

In another embodiment, R is an alkoxy group substituted with a substituted or unsubstituted bithiophene group.

In another embodiment, R is an alkoxy group substituted with a bithiophene group substituted with an alkyl group.

In one embodiment, R is an alkoxy group substituted with a bithiophene group substituted with a hexyl group.

In another embodiment, R is an ethyloxy group substituted with a bithiophene group substituted with a hexyl group.

In one embodiment of the present specification, R5 or R6 and R7 or R8 are bonded to each other to form a 5-membered or 6-membered aliphatic ring. The substituent of the formed ring is substituted with -(L)a-(M)b.

In one embodiment of the present specification, R is a substituted or unsubstituted arylalkyloxy group.

In one embodiment of the present specification, R is a benzyloxy group.

In one embodiment of the present specification, R is a substituted or unsubstituted alkyl group.

In one embodiment, R is an alkyl group unsubstituted or substituted with an aryl group.

In another embodiment, R is an alkyl group unsubstituted or substituted with a phenyl group.

In another embodiment, R is an ethyl group substituted with an aryl group.

In another embodiment, R is an ethyl group substituted with a phenyl group.

In another embodiment, R is a propyl group substituted with an aryl group.

In another embodiment, R is a propyl group substituted with a phenyl group.

In one embodiment of the present specification, R is an alkyl group.

In another embodiment, R is a linear or branched alkyl group.

In another embodiment, R is a hexyl group.

In another embodiment, R is a 2-ethylhexyl group.

In one embodiment of the present specification, R is a substituted or unsubstituted aryl group.

In another embodiment, R is an aryl group.

In one embodiment, R is a phenyl group.

In one embodiment of the present specification, the fullerene derivative represented by Chemical Formula 1 is any one of the following Chemical Formulae 1-1-1 to 1-1-54.

[Formula 1-1-1]

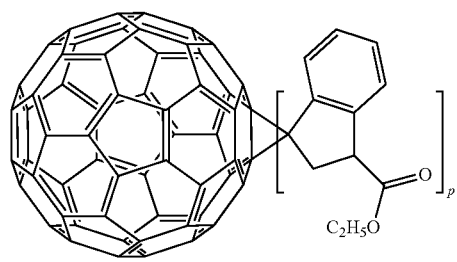

[Formula 1-1-2]

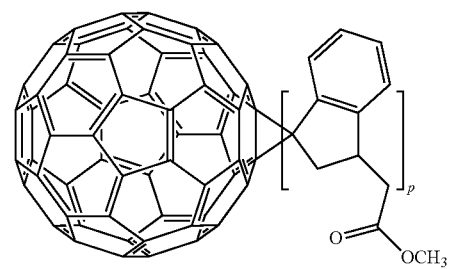

[Formula 1-1-3]

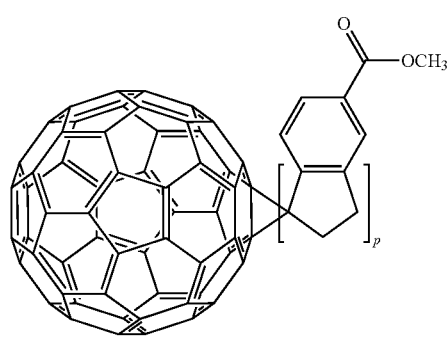

[Formula 1-1-4]

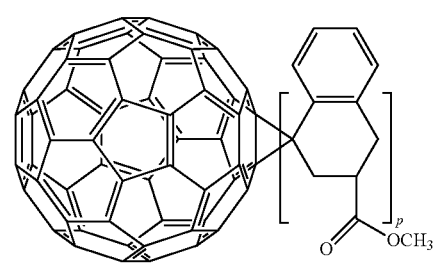

[Formula 1-1-5]

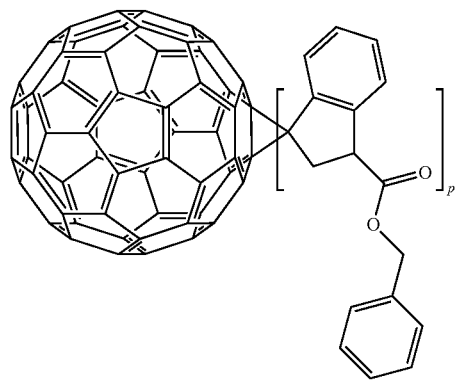

[Formula 1-1-6]

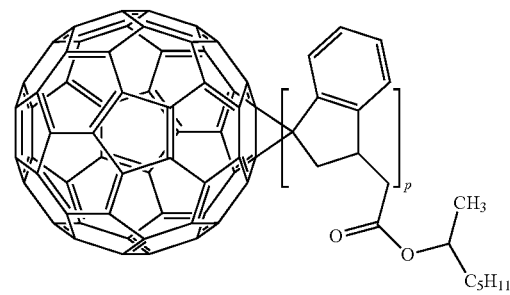

-continued
[Formula 1-1-7]
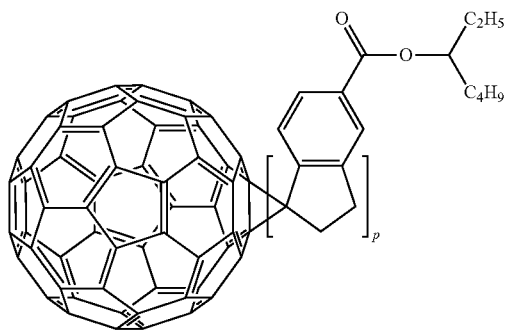
[Formula 1-1-8]
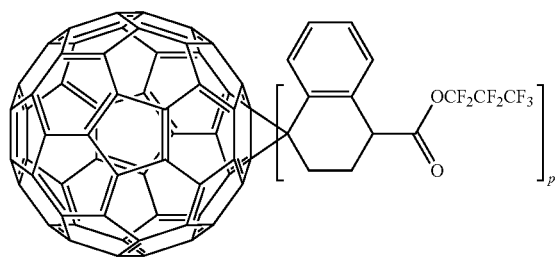
[Formula 1-1-9]
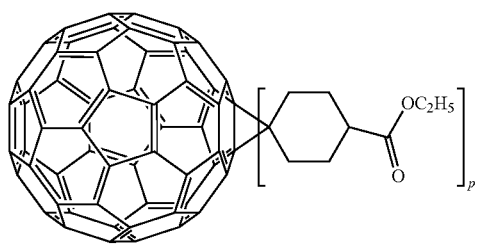
[Formula 1-1-10]
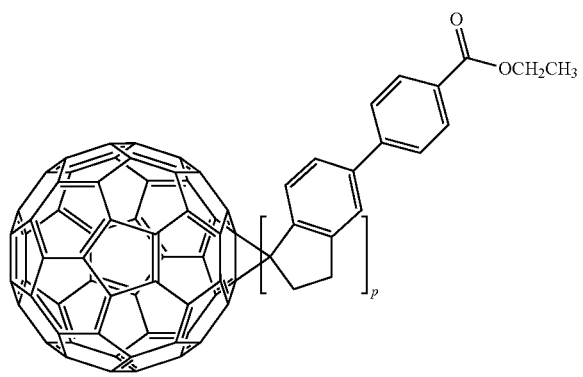
[Formula 1-1-11]
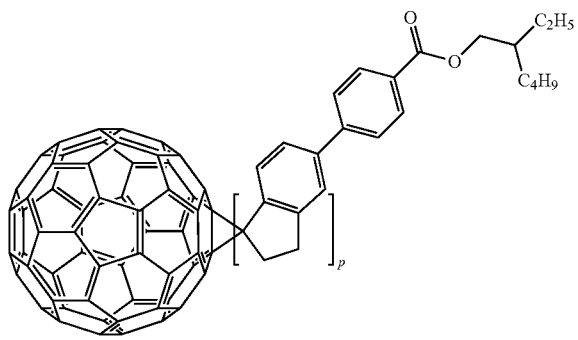
[Formula 1-1-12]
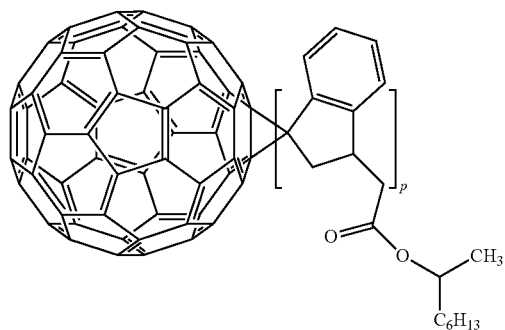
[Formula 1-1-13]
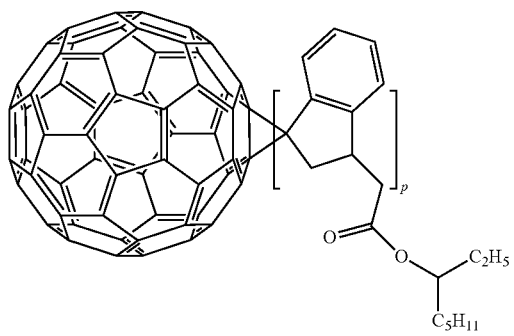
[Formula 1-1-14]
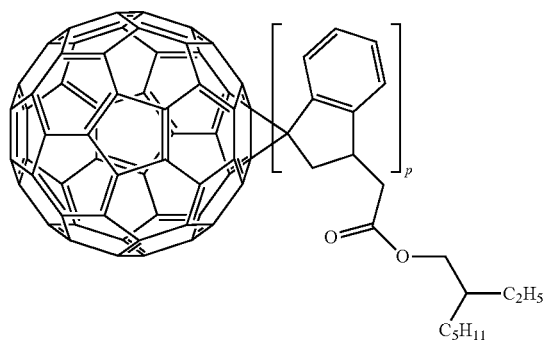

[Formula 1-1-15]
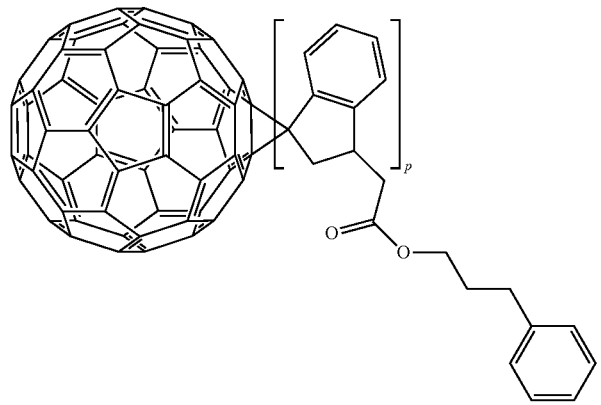
[Formula 1-1-16]
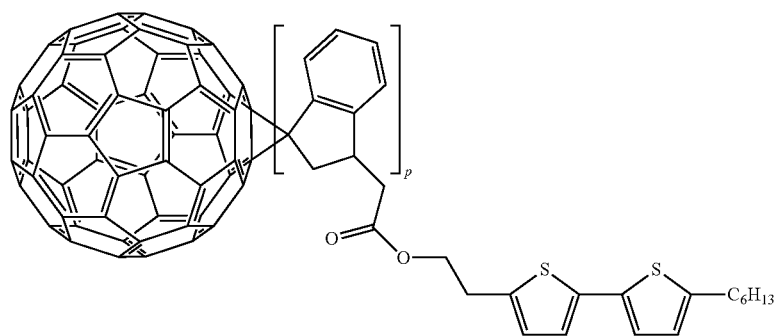
[Formula 1-1-17] [Formula 1-1-18]
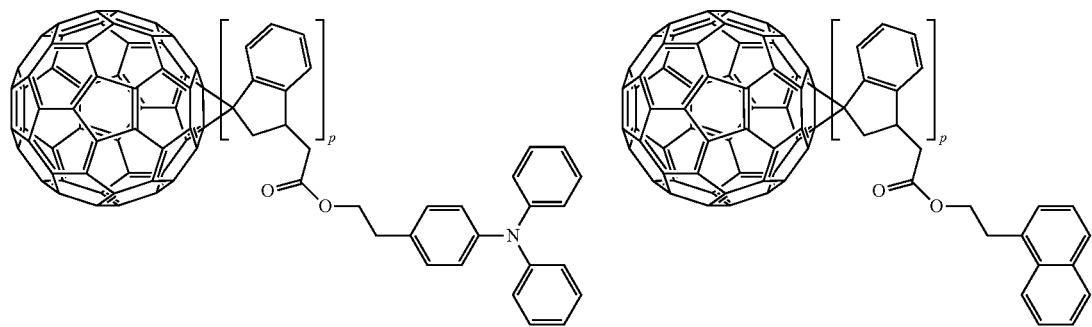
[Formula 1-1-19]
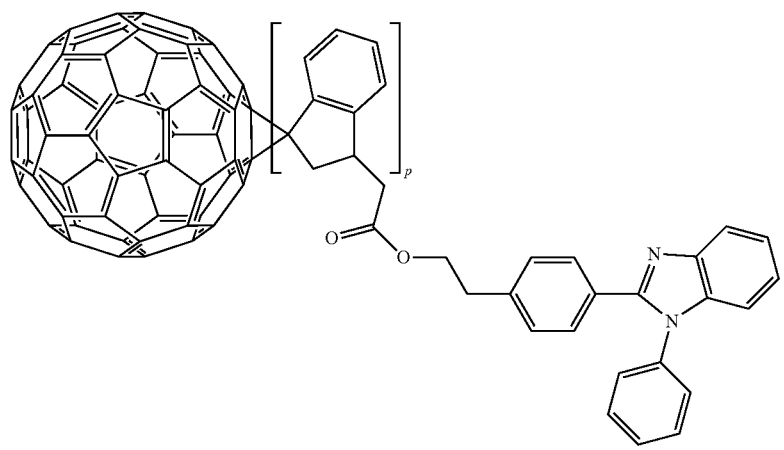

[Formula 1-1-20]
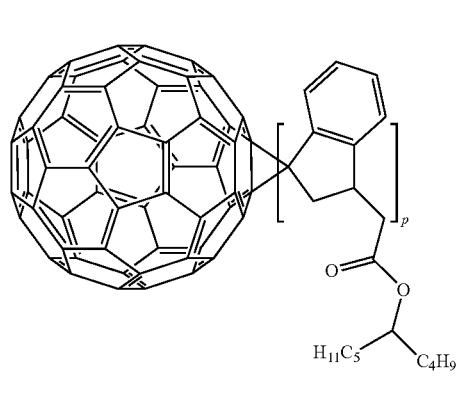
[Formula 1-1-21]
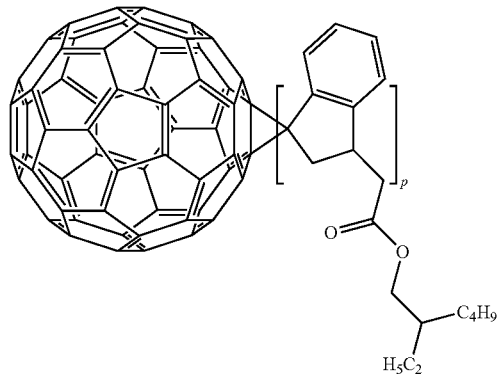
[Formula 1-1-22]
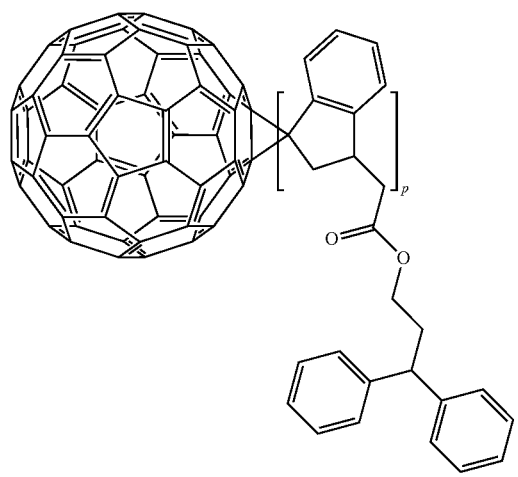
[Formula 1-1-23]
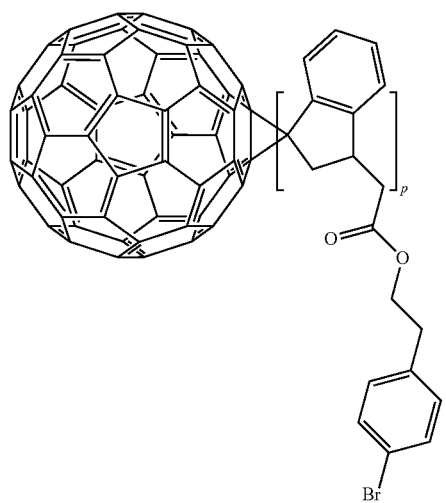
[Formula 1-1-24]
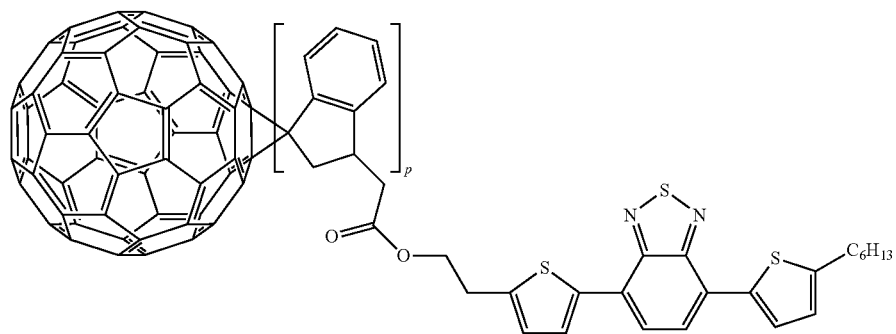

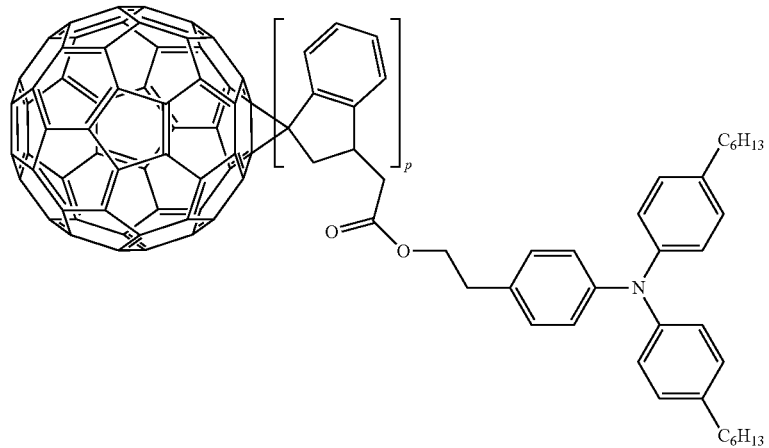
[Formula 1-1-25]
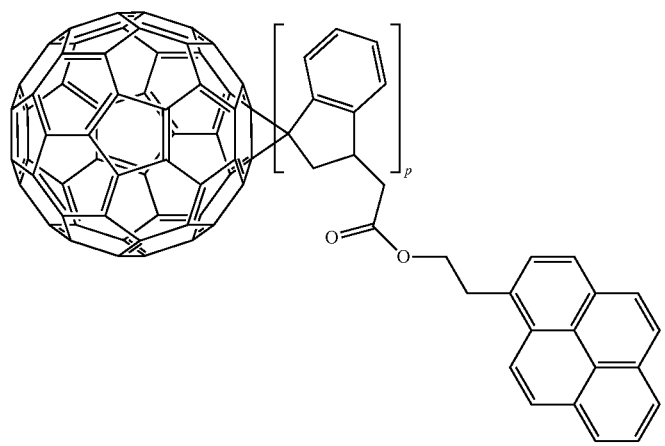
[Formula 1-1-26]
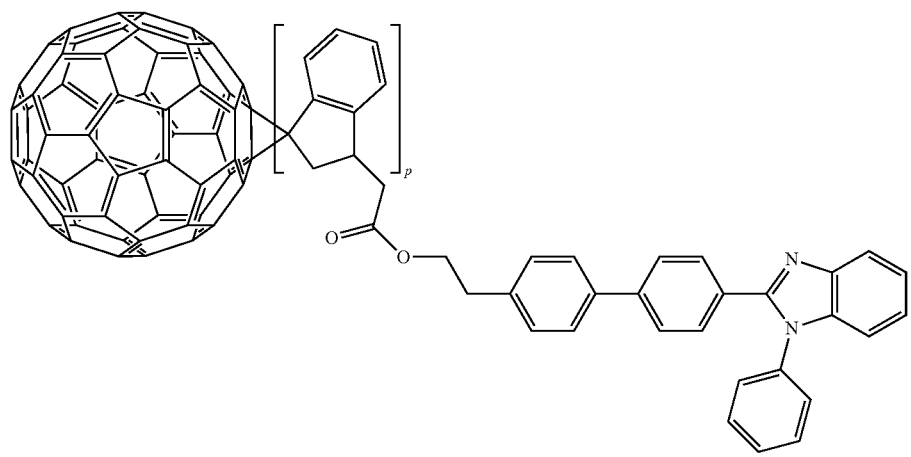
[Formula 1-1-27]

[Formula 1-1-28]
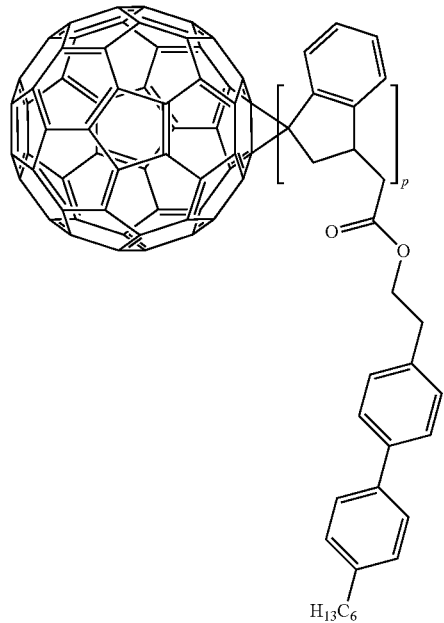
[Formula 1-1-29]
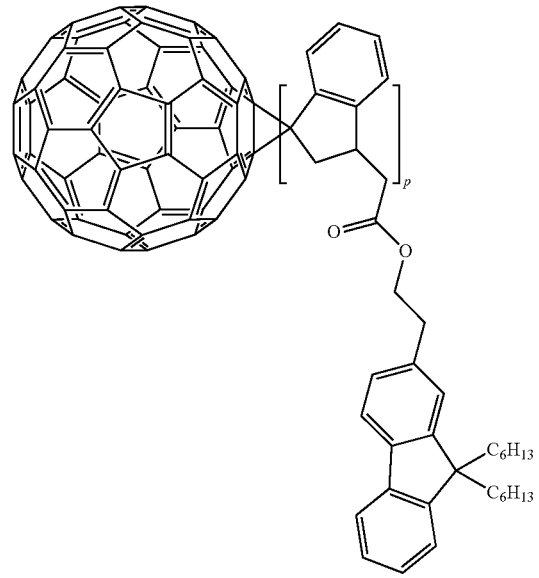
[Formula 1-1-30]
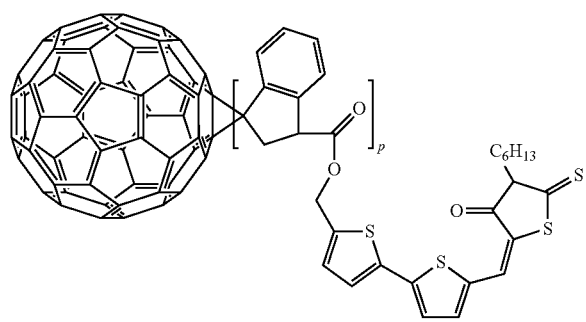
[Formula 1-1-31]
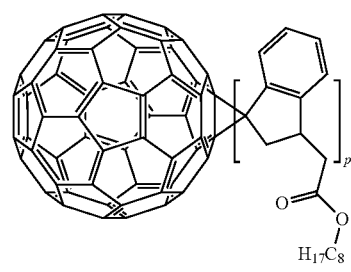
[Formula 1-1-32]
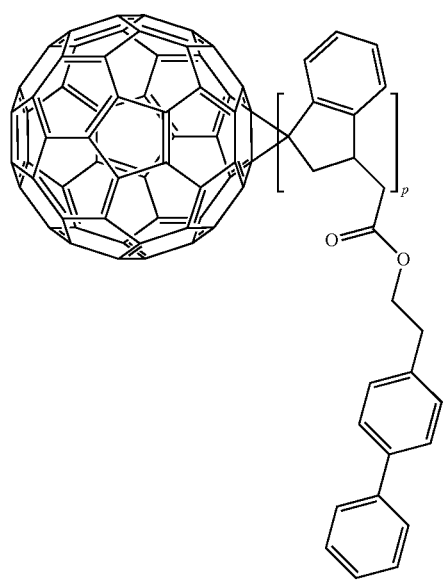
[Formula 1-1-33]
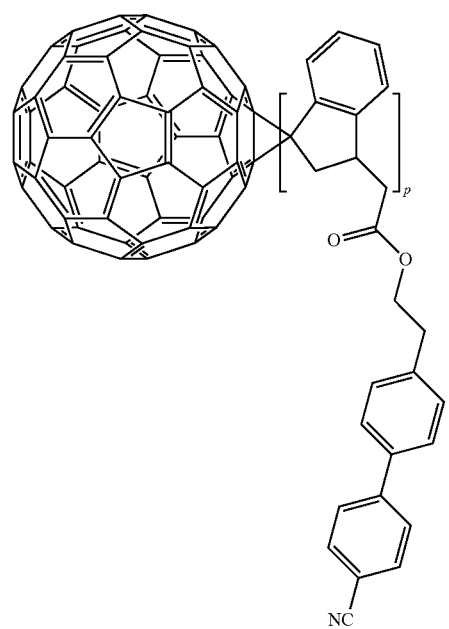

[Formula 1-1-34]
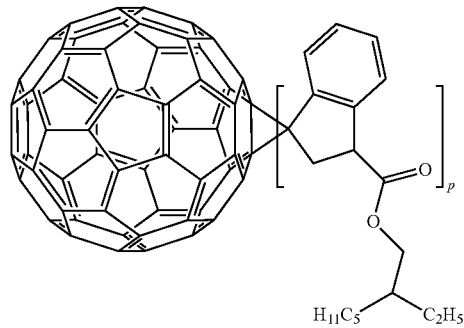
[Formula 1-1-35]
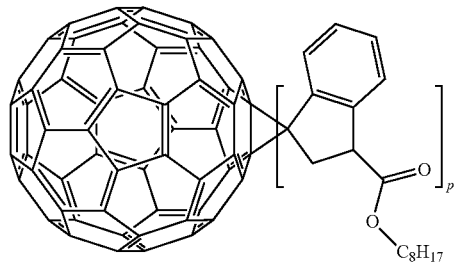
[Formula 1-1-36]
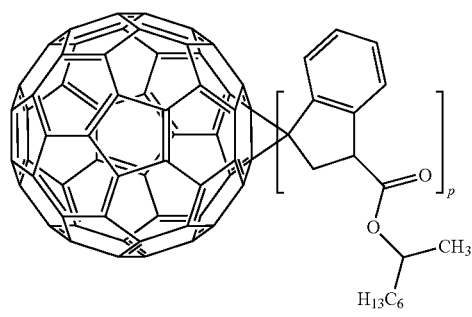
[Formula 1-1-37]
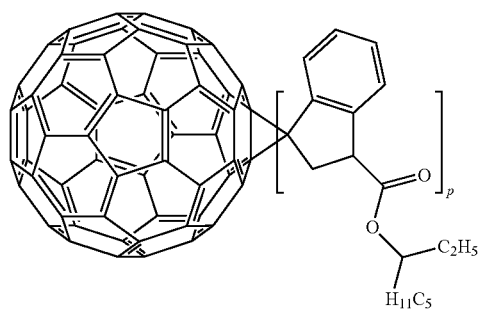
[Formula 1-1-38]
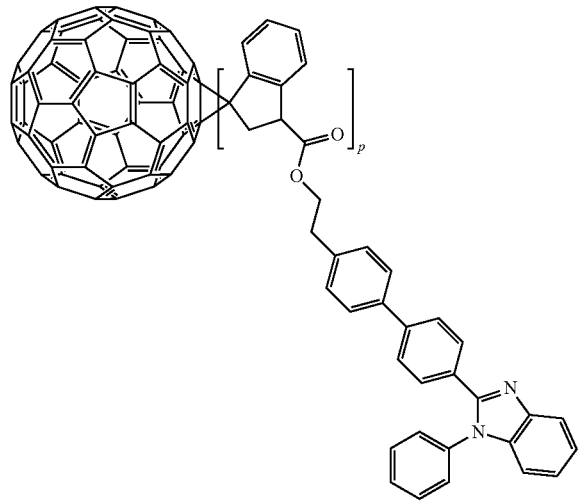
[Formula 1-1-39]
[Formula 1-1-40]
[Formula 1-1-41]
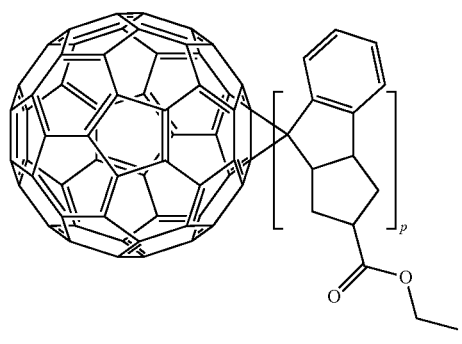

[Formula 1-1-42]
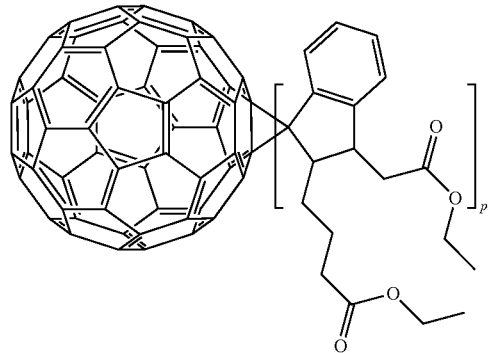
[Formula 1-1-43]
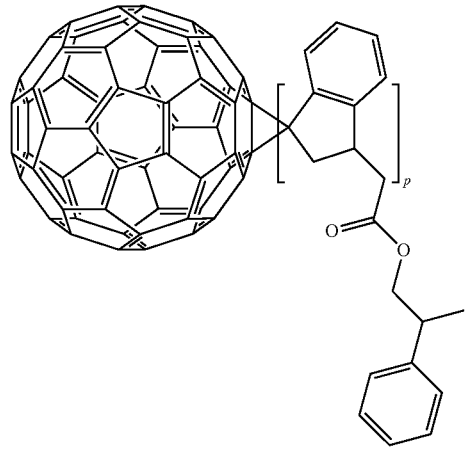
[Formula 1-1-44]
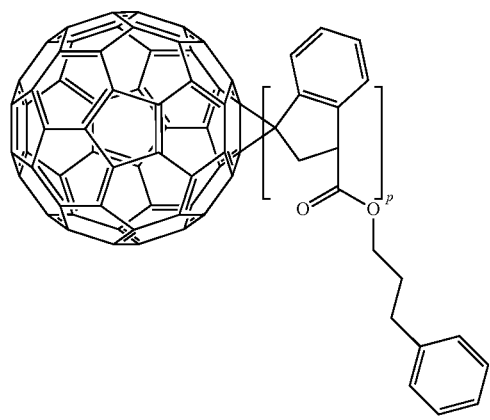
[Formula 1-1-45]
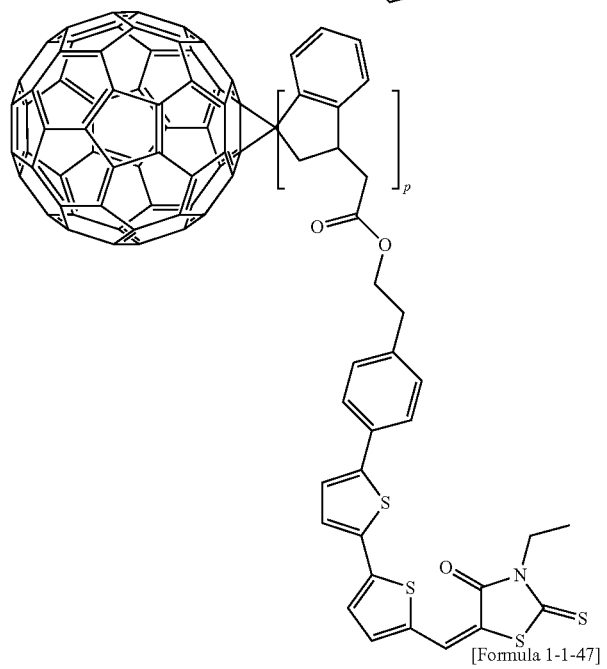
[Formula 1-1-46]
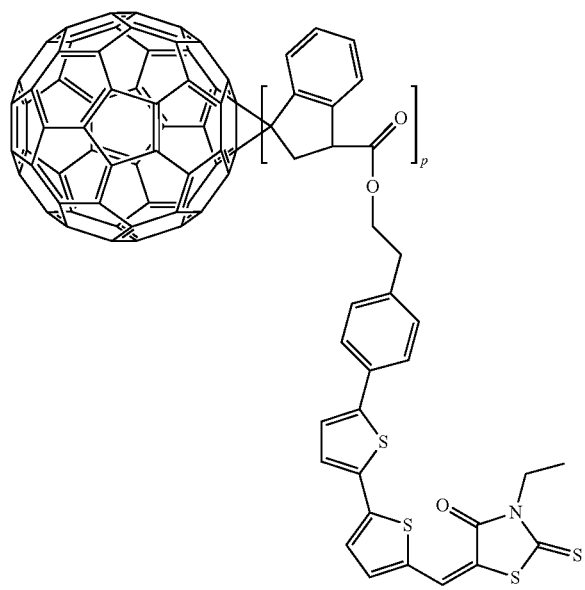
[Formula 1-1-47]
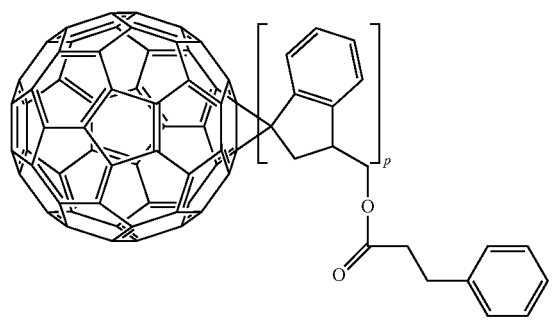

[Formula 1-1-48]
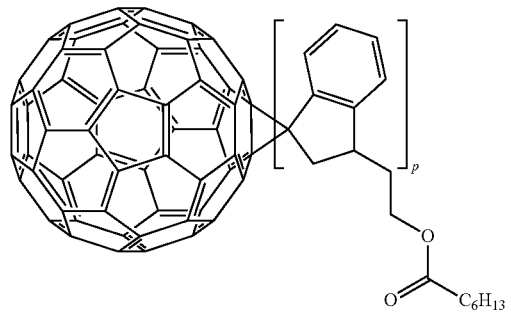
[Formula 1-1-49]
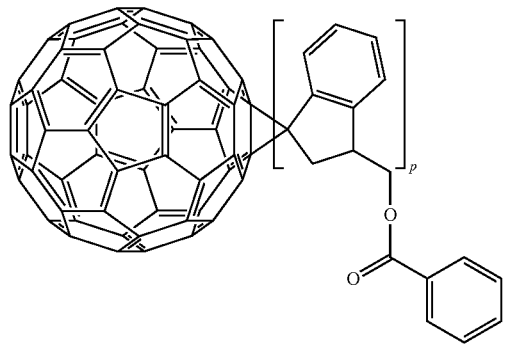
[Formula 1-1-50]
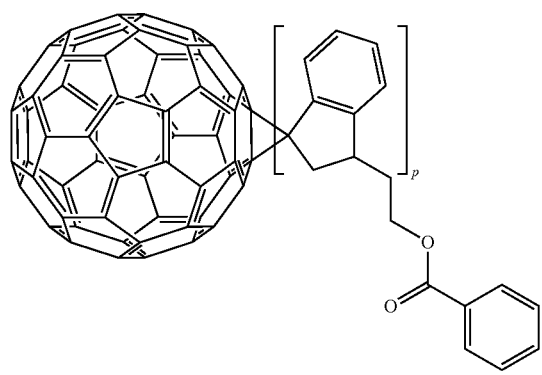
[Formula 1-1-51]
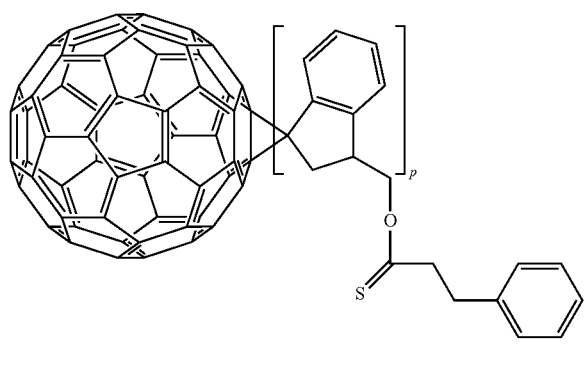
[Formula 1-1-52]
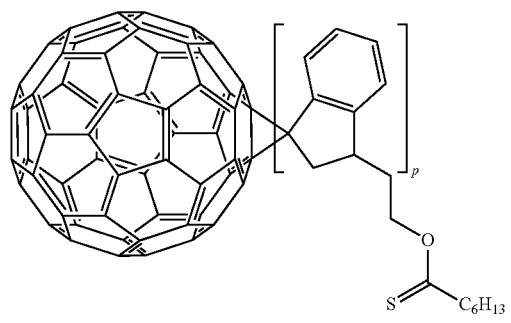
[Formula 1-1-53]
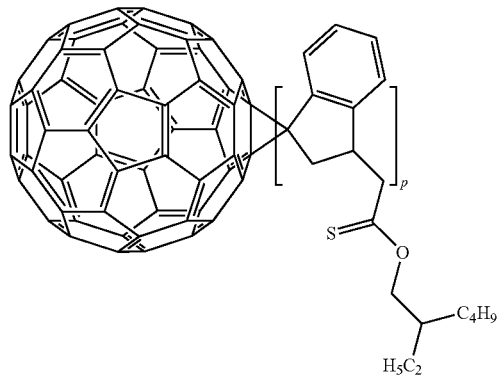
[Formula 1-1-54]
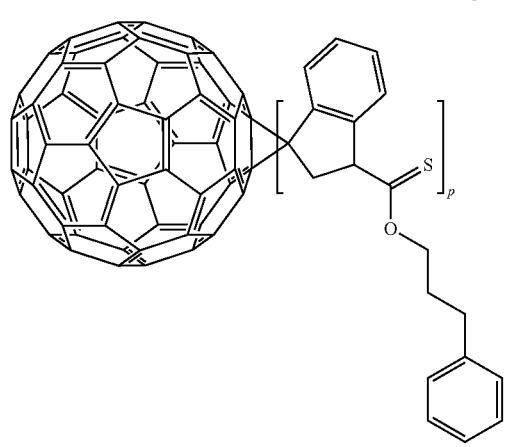

In one embodiment of the present specification, the fullerene derivative has an LUMO energy level ranging from −3.4 eV to −5 eV.

When an electric field is applied to a fullerene derivative having an LUMO energy level of the above range, it is effective in improving the injection of charges and/or the mobility of currents since it is a molecular orbital in which the injection of holes and electrons readily occurs, that is, an HOMO and LUMO energy level.

In addition, the fullerene derivative according to one embodiment of the present specification may have a sufficient frontier orbital overlap enabling effective charge transfer between neighboring molecules. Therefore, an organic solar cell that uses the fullerene derivative can have high efficiency.

The fullerene derivative according to one embodiment of the present specification has excellent solubility, and a low-temperature solution process is possible when an organic solar cell is manufactured, therefore, it is economical in terms of costs since a thin film may be readily formed even on a plastic substrate.

In addition, the fullerene derivative according to one embodiment of the present specification may have a film form with a thin film shape such as a single crystal.

The fullerene derivative according to one embodiment of the present specification has increased solubility, therefore, effective charge transfer may occur when an organic thin film layer is formed since the effect of morphology improvement is excellent.

The fullerene derivative of Chemical Formula 1 and Chemical Formula 2 may be obtained by, as in the following reaction condition A, forming an imine group with a C=N double bond by reacting an aryl hydrazide to a carbonyl group (ketone C=O) in an organic solvent such as tetrahydrofuran (THF) or an alkyl alcohol such as ethanol or methanol, and then, as in reaction condition B, forming a carbon-carbon bond with a carbon bundle compound of Cn.

Chemical Formula 2-A substituted with

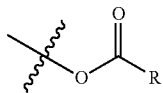

according to one embodiment of the present specification may be obtained based on the method described in a literature, Kinetic resolution of 3-hydroxymethylbenzocycloalkanols by selective asymmetric hydrogen-transfer oxidation, Yolanda Caro, María Torrado, Christian F. Masaguer* and Enrique Ravina, Tetrahedron: Asymmetry 14 (2003) 3689-3696, and Chemical Formula 2-A substituted with

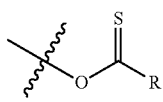

may be obtained using a Lawesson reagent described in Photochemistry of diethynyl sulfides: a cycloaromatization for the formation of five-membered rings Lewis, Kevin D.; Matzger, Adam J.; Wenzler, David L. Organic Letters, 2003, vol. 5, #13 p. 2195-2197 and Microwave-Accelerated Solvent-Free Synthesis of Thioketones, Thiolactones, Thioamides, Thionoesters, and Thioflavonoids. Org. Lett., 1999, 1(5), pp 697-700.

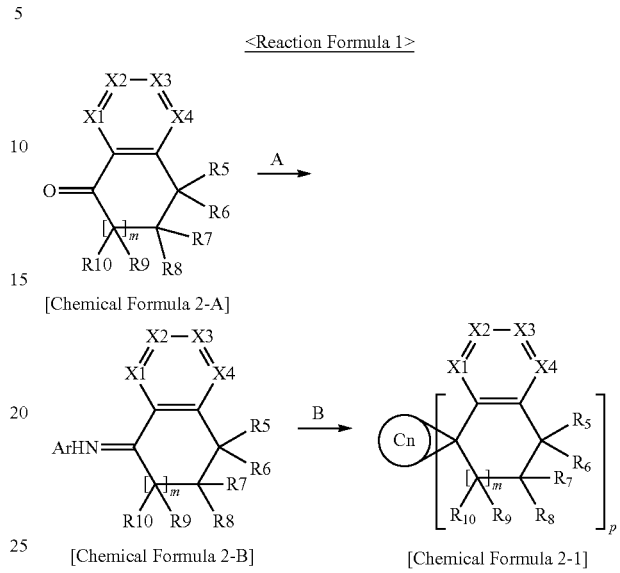

Reaction Condition A

1) Aromatic hydrazine (ArNHNH$_2$), small amount of sulfuric acid or hydrochloric acid (H$_2$SO$_4$ or HCl), alkyl alcohol or tetrahydrofuran (THF), reflux 2) Filtration of the produced solid compound or purification after separating the organic mixed solution layer The reaction described above is a general synthesis method preparing an ester, and after an alkyl ester is prepared from a carboxylic acid linked to a pentagonal or hexagonal cyclic compound, the alkyl ester may be transformed to an alkyl alcohol through the reduction of the alkyl ester. Applying this, those skilled in the art may readily prepare a fullerene derivative in which with various alkyl esters or aryl esters are substituted.

Furthermore, a fullerene derivative substituted with a carboxylamide group may be prepared by transforming a carboxylic acid to thionyl chloride (SOCl$_3$), oxalyl chloride (C$_2$O$_2$Cl$_2$) or carbonyl chloride, and then transforming to an alkylamine or arylamine compound.

A cyclic ketone-based Chemical Formula 2-A that is not fused or fused with a substituted or unsubstituted aromatic ring or a substituted or unsubstituted aromatic heteroring, and a substituted or unsubstituted aromatic hydrazine are stirred for 3 to 24 hours in methanol or ethanol while heating. The formed solid is dried after filtering, or the formed liquid is purified using column chromatography to give a product.

Reaction Condition B

1) C$_{60}$, 1,2-dichlorobenzene or chlorobenzene, pyridine

2) Adding sodium methoxide

3) Stirring at 120° C. to 170° C.

Chemical Formula 2-B prepared in the reaction condition A, C$_{60}$, o-dichlorobenzene, pyridine and sodium methoxide are placed, and stirred at 120° C. to 170° C. while heating, and a fullerene derivative represented by Chemical Formula 2-1 is prepared.

A fullerene derivative including a carbonyl ester group among the fullerene derivatives obtained in the reaction condition B may be readily transformed to a fullerene derivative including a thioester group using a Lawesson reagent and the like.

A fullerene derivative including an ester group among the fullerene derivatives obtained in the reaction condition B may be readily transformed to a fullerene derivative including a carboxylic acid group through a hydrolysis reaction and the like, and to a fullerene derivative including an aldehyde group through a reduction reaction.

Chemical Formulae 3 to 5 may be prepared according to the same reaction conditions and orders described above.

R5 to R10, m, p and Cn are the same as those defined above.

One embodiment of the present specification provides an organic solar cell including a first electrode, a second electrode provided opposite to the first electrode, and one or more organic material layers provided between the first electrode and the second electrode, wherein one or more layers of the organic material layers include the fullerene derivative.

FIG. 1 is a diagram illustrating an organic solar cell according to one embodiment of the present specification. In FIG. 1, a substrate (101), a first electrode (102), a hole transfer layer (103), a photoactive layer (104) and a second electrode (105) are included.

In an organic solar cell, a p-type semiconductor forms excitons paired with holes and electrons by light excitation, and the excitons are separated into electrons and holes in a p-n junction. The separated electrons and holes are transferred to an n-type semiconductor thin film and a p-type semiconductor thin film, respectively, and are collected in a first electrode and a second electrode, respectively, and as a result, the organic solar cell may be used as an electric energy externally.

In one embodiment of the present specification, the organic material layer includes a photoactive layer, and an organic material layer provided between the photoactive layer and the first electrode or the second electrode, wherein the organic material layer provided between the photoactive layer and the first electrode or the second electrode includes the fullerene derivative.

In one embodiment of the present specification, the organic material layer includes a hole transfer layer, a hole injection layer or a layer that transfers and injects holes at the same time, and the hole transfer layer, the hole injection layer or the layer that transfers and injects holes at the same time includes the fullerene derivative.

In another embodiment, the organic material layer includes an electron injection layer, an electron transfer layer or a layer that injects and transfers electrons at the same time, and the electron injection layer, the electron transfer layer or the layer that injects and transfers electrons includes the fullerene derivative.

In one embodiment of the present specification, the organic material layer includes a photoactive layer, and the photoactive layer includes the fullerene derivative.

In one embodiment of the present specification, the organic material layer includes a photoactive layer, the photoactive layer has a bilayer structure including an n-type organic material layer and a p-type organic material layer, and the n-type organic material layer includes the fullerene derivative.

In one embodiment of the present specification, the organic material layer includes a photoactive layer, the photoactive layer includes an electron donor material and an electron acceptor material, and the electron acceptor material includes the fullerene derivative.

In one embodiment of the present specification, the electron donor material and the electron acceptor material in the organic solar cell form a bulk heterojunction (BHJ).

A Bulk heterojunction means an electron donor material and an electron acceptor material being mixed together in a photoactive layer.

The fullerene derivative according to one embodiment of the present specification may efficiently prepare an electron acceptor material having excellent solubility for organic solvents through a simple preparation method. In addition, an electron acceptor material having high solubility may be prepared since materials having photoreactivity, photostability and conductivity may be used as a starting material in a reaction.

In one embodiment of the present specification, the n-type organic material layer and/or the electron donor material is preferably compatible with a light absorption wavelength range or a spectrum within sunlight, preferably has a strong light absorbency, and has excellent electric properties such as charge mobility, and unimolecular or polymer compounds capable of being used in a solution process may be used.

Typical electron donor materials include the following structures including poly(phenylene vinylene) (PPV)-based polymers or poly(3-hexylthiophene) (P3HT)-based polymers.

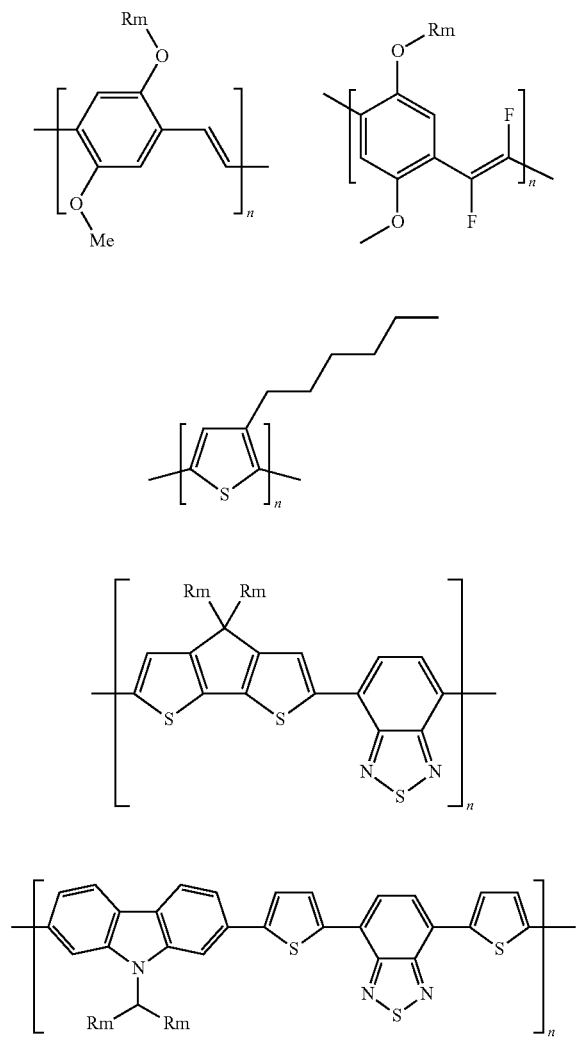

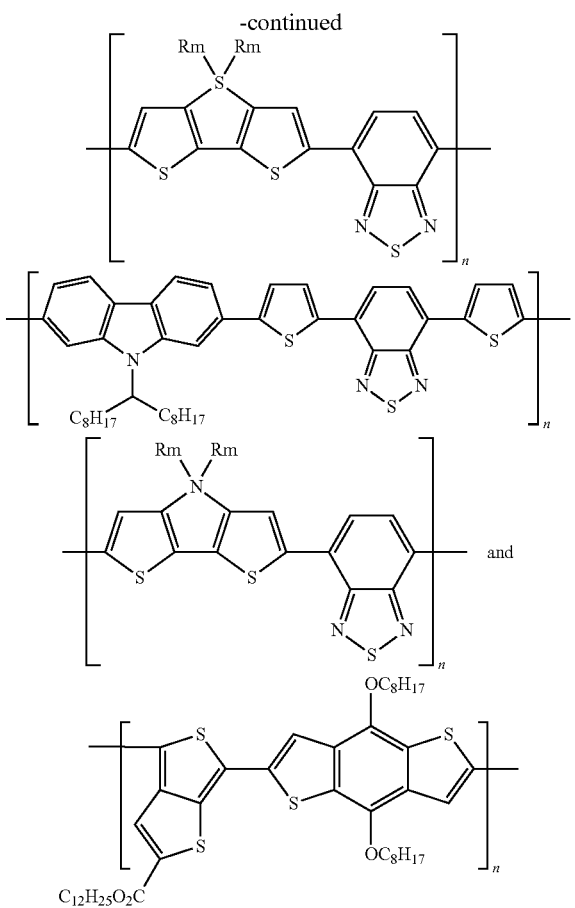

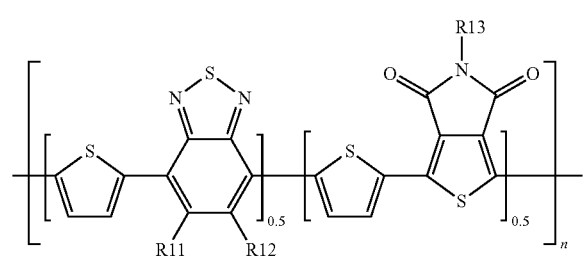

n is an integer of 1 to 1,000,

Rm is hydrogen, a substituted or unsubstituted alkyl group; a substituted or unsubstituted cycloalkyl group; a substituted or unsubstituted alkoxy group; a substituted or unsubstituted alkenyl group; a substituted or unsubstituted aromatic or aliphatic heteroring group that includes one or more of N, O and S atoms, or a substituted or unsubstituted aryl group.

In one embodiment of the present specification, the electron donor material is P3HT or a compound represented by the following Chemical Formula 2-1.

[Chemical Formula 2-1]

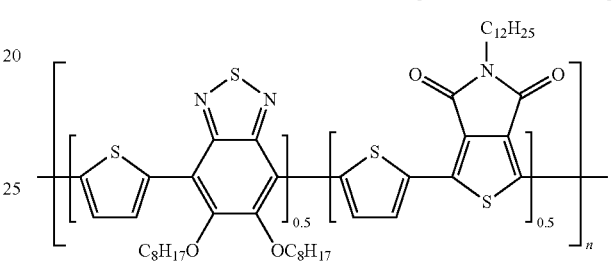

In Chemical Formula 2-1,

R11 to R13 are the same as or different from each other, and each independently a substituted or unsubstituted alkyl group; or a substituted or unsubstituted alkoxy group.

In one embodiment of the present specification, R11 is a substituted or unsubstituted alkoxy group.

In one embodiment, R11 is a substituted or unsubstituted octoxy group.

In another embodiment, R11 is an octoxy group.

In one embodiment of the present specification, R12 is a substituted or unsubstituted alkoxy group.

In one embodiment, R12 is a substituted or unsubstituted octoxy group.

In another embodiment, R12 is an octoxy group.

In one embodiment of the present specification, R13 is a substituted or unsubstituted alkyl group.

In another embodiment, R13 is a dodecanyl group.

In one embodiment, the electron donor material represented by Chemical Formula 2-1 is represented by the following Chemical Formula 2-1-1.

[Chemical Formula 2-1-1]

The electron donor materials are preferably materials having a small band gap so as to absorb all visible ray regions within sunlight, and are generally polymer compounds, but are not limited thereto.

The electron donor material and the electron acceptor material are mixed in a ratio of 1:10 to 10:1 (w/w). After the electron donor material and the electron acceptor material are mixed, the result may be annealed for 1 second to 24 hours at 30 to 300° C. in order to maximize the properties.

In one embodiment of the present specification, the thickness of the photoactive layer ranges from 10 nm to 1,000 nm.

In one embodiment of the present specification, the first electrode may be an anode electrode or a cathode electrode. In addition, the second electrode may be a cathode electrode or an anode electrode.

In one embodiment of the present specification, the organic solar cell may be arranged in order of an anode electrode, a photoactive layer and a cathode electrode.

In another embodiment, the organic solar cell may also be arranged in order of a cathode electrode, a photoactive layer and an anode electrode, but the arrangement is not limited thereto.

In another embodiment, the organic solar cell may be arranged in order of an anode electrode, a hole transfer layer, a photoactive layer, an electron transfer layer and a cathode electrode, or arranged in order of a cathode electrode, an electron transfer layer, a photoactive layer, a hole transfer layer and an anode electrode, but the arrangement is not limited thereto.

In another embodiment, the organic solar cell may also be arranged in order of an anode electrode, a buffer layer, a photoactive layer and a cathode electrode.

The organic solar cell of the present specification may be prepared using materials and methods known in the art except that the fullerene derivative represented by Chemical Formula 1 is included in one or more layers of the organic material layers of the organic solar cell.

In one embodiment of the present specification, a method for fabricating an organic solar cell, which includes the steps of preparing a substrate; forming a first electrode on top of the substrate; forming one or more organic material layers including a photoactive layer on top of the first electrode; and forming a second electrode on top of the organic material layers, wherein one or more layers of the organic material layers include the fullerene derivative.

Specifically, in one embodiment of the present specification, the method may include the steps of preparing a substrate, forming an anode on top of the substrate, forming a hole transfer layer on top of the anode, forming a photoactive layer on top of the hole transfer layer, forming an electron transfer layer on top of the photoactive layer, and forming a cathode on top of the electron transfer layer.

In another embodiment, the method may include the steps of preparing a substrate, forming a cathode on top of the substrate, forming an electron transfer layer on top of the cathode, forming a photoactive layer on top of the electron transfer layer, forming a hole transfer layer on top of the photoactive layer, and forming an anode on top of the hole transfer layer.

The organic solar cell of the present specification may be prepared by laminating, for example, an anode, a photoactive layer and a cathode on a substrate in consecutive order.

The fullerene derivative may be included in the hole transfer layer; the photoactive layer; and/or the electron transfer layer.

For example, the organic solar cell according to the present invention may be manufactured by forming an anode by depositing a metal, a metal oxide having conductivity, or alloys thereof on a substrate using a physical vapor deposition (PVD) method such as sputtering or e-beam evaporation, forming an organic material layer thereon using a vacuum deposition or solution coating method, and then depositing a material that can be used as a cathode thereon.

Each organic material layer may be prepared using a solvent process instead of a deposition method using various unimolecular or polymer materials, and examples of the solvent process include a roll to roll method, spin coating, dip coating, casting, roll court, flow coating, doctor blading, screen printing, ink jet printing, gravure printing, offset printing, spray coating, a thermal printing method or the like.

Each organic material layer may be prepared using a method including dry film-forming methods such as vacuum deposition, sputtering, plasma and ion plating.

In one embodiment of the present specification, the method may include the steps of depositing an anode, laminating a photoactive layer, arraying the photoactive layer, heat treating the photoactive layer and depositing a cathode.

In the step of laminating the photoactive layer, the photoactive layer may be disposed in a composite thin film structure in which a solution mixed with an electron donor material and an electron acceptor material is sprayed and deposited on the upper side of both electrodes, that is, in a bulk heterojunction.

As the electron acceptor material, a mixed solution in which a composite polymer material is dissolved in an organic solvent may be used, and the electron acceptor material may include the fullerene derivative.

In one embodiment of the present specification, P3HT dissolved in an organic solvent is used with the fullerene derivative.

The substrate in the present specification may include a glass substrate or a transparent plastic substrate, which has excellent transparency, surface smoothness, handling easiness and water resistance, but is not limited thereto, and substrates typically used for organic solar cells may be used without limit. Specific examples thereof include glass, polyethylene terphthalate (PET), polyethylene naphthalate (PEN), polypropylene (PP), polyimide (PI), triacetyl cellulose (TAC) and the like, but are not limited thereto.

The anode electrode may include a material that is transparent and has excellent conductivity, but is not limited thereto. Examples of the anode material include metals such as vanadium, chromium, copper, zinc or gold, or alloys thereof; metal oxides such as zinc oxides, indium oxides, indium tin oxides (ITO), or indium zinc oxides (IZO); and a combination of metals and oxides such as ZnO:Al or $SnO_2$:Sb; conductive polymers such as poly(3-methylthiophene), poly[3,4-(ethylene-1,2-dioxy)thiophene] (PEDOT), polypyrrole and polyaniline, and the like, but are not limited thereto.

The method of forming the anode electrode is not particularly limited, however, the anode electrode may be formed by being applied to one surface of the substrate or coated in the form of a film using a method such as sputtering, E-bean, thermal deposition, spin coating, screen printing, inkjet printing, doctor blade or gravure printing.

When the anode electrode is formed on a substrate, the result may go through a process of cleaning, dehydrating and modifying to be hydrophilic.

For example, after the patterned ITO substrate is cleaned with a cleaning agent, acetone and isopropyl alcohol (IPA) in consecutive order, the ITO substrate is dried for 1 to 30 minutes at 100 to 150° C. and preferably for 10 minutes at 120° C. on a heating plate in order to remove moisture, and when the substrate is completely cleaned, the surface of the substrate is modified to be hydrophilic.

Through the surface modification described above, the junctional surface potential may be maintained at a level suitable for the surface potential of the photoactive layer. In addition, when the surface is modified, a polymer thin film may be readily formed on the anode electrode, and the quality of the thin film may be improved.

Preprocessing technologies for the anode electrode include a) a surface oxidation method using parallel plate discharge, b) a method of oxidizing the surface through the ozone generated using UV rays in a vacuum, and c) a method of oxidizing using the oxygen radicals generated by plasma.

One of the methods described above may be selected depending on the condition of the anode electrode or the substrate. However, it is commonly preferable to prevent the leave of the oxygen of the anode electrode or the surface of the substrate and to suppress the remaining of moisture and organic materials as much as possible, no matter which method is used. In this case, practical effects of the preprocessing can be maximized.

As a specific example, a method of oxidizing the surface through the ozone generated using UV rays may be used. Herein, the patterned ITO substrate may be fully dried by baking the patterned ITO substrate on a hot plate after ultrasonic cleaned, introduced into a chamber, and then the patterned ITO substrate may be cleaned by the ozone generated by reacting the oxygen gas with UV light using a UV lamp.

However, the method of surface modification of the patterned ITO substrate in the present specification is not particularly limited, and any method oxidizing a substrate may be used.

The cathode electrode may include a metal having small work function, but is not limited thereto. Specific examples thereof include metals such as magnesium, calcium, sodium, potassium, titanium, indium, yttrium, lithium, gadolinium, aluminum, silver, tin and lead, or alloys thereof; or multi-layer structure materials such as LiF/Al, LiO$_2$/Al, LiF/Fe, Al:Li, Al:BaF$_2$ and Al:BaF$_2$:Ba, but are not limited thereto.

The cathode electrode may be formed by being deposited inside a thermal depositor showing a vacuum degree of 5×10$^{-7}$ torr or less, but the formation is not limited to this method.

The hole transfer layer and/or the electron transfer layer material play the role of efficiently transferring the electrons and the holes separated in the photoactive layer to the electrode, and the material is not particularly limited.

The hole transfer layer material may include PEDOT:PSS (Poly(3,4-ethylenediocythiophene) doped with poly(styrenesulfonic acid)), molybdenum oxides (MoO$_x$); vanadium oxides (V$_2$O$_5$); nickel oxides (NiO); and tungsten oxides (WO$_x$) and the like, but is not limited thereto.

The electron transfer layer material may include electron-extracting metal oxides, and may specifically include a metal complex of 8-hydroxyquinoline; a complex including Alq$_3$; a metal complex including Liq; LiF; Ca; titanium oxides (TiO$_x$); zinc oxides (ZnO); cesium carbonate (Cs$_2$CO$_3$) and the like, but is not limited thereto.

The photoactive layer may be formed by dissolving a photoactive material such as an electron donor and/or an electron acceptor in an organic solvent, and then applying the solution using a method such as spin coating, dip coating, screen printing, spray coating, doctor blade and brush painting, but the method is not limited thereto.

Hereinafter, a method for preparing the fullerene derivative and a method for fabricating an organic solar cell using the fullerene derivative will be described in detail with reference to preparation examples and examples. However, the following examples are for illustrative purposes only, and the scope of the present specification is not limited thereto.

Preparation Example 1

Preparation of Chemical Formula 1-1-1

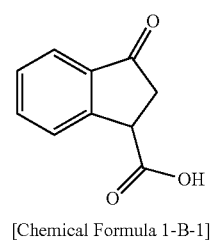

[Chemical Formula 1-B-1]

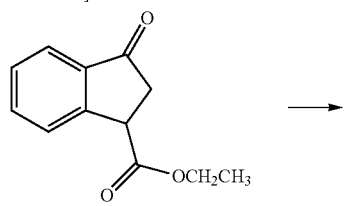

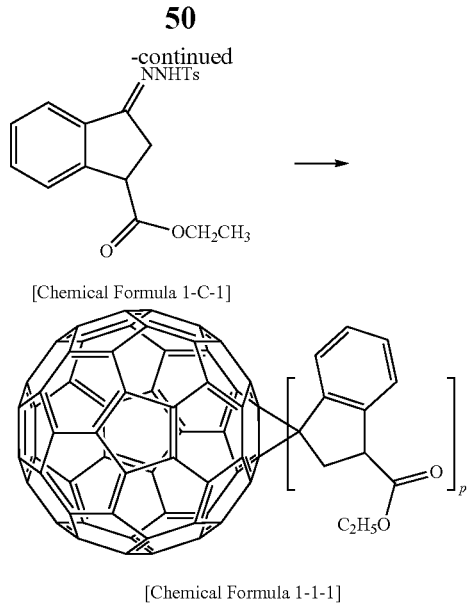

[Chemical Formula 1-1-1]

3-Oxo-1-indancarboxylic acid (10.0 g, 56.8 mmol), ethanol (180 mL), and sulfuric acid (H$_2$SO$_4$) (1 mL) were placed, and the mixture was stirred for 24 hours while heating. The reaction temperature was lowered to room temperature, the ethanol was vacuum distilled and the result was passed through a silica gel layer, and ethyl-3-oxo-2,3-dihydro-1H-indene-1-carboxylate, a compound of Chemical Formula 1-B-1 (11.4 g, 98%), was obtained in a liquid state.

The compound represented by Chemical Formula 1-B-1 in the preparation example above (11.4 g, 55.86 mmol) was completely dissolved in 220 mL of methanol while heating. After p-toluenesulfonyl hydrazide (10.41 g, 55.86 mmol) was added to the mixed solution, the mixture was stirred for 6 hours while heating. After the reaction temperature was lowered to room temperature and the methanol solvent was vacuum distilled, the formed liquid was purified using column chromatography (EA:HEX=1:4), and a liquid compound of Chemical Formula 1-C-1 (15.8 g, yield 76%) was prepared.

C$_{60}$ (5.0 g, 5 eq. 6.94 mmol), o-dichlorobenzene (ODCB, 100 mL), pyridine (20 mL) and sodium methoxide (NaOCH$_3$, 1.28 eq. 4.62 mmol, 0.24 g) were placed, and the mixture was stirred at 120° C. while heating. The compound of Chemical Formula 1-C-1 (1.43 g, 3.85 mmol) was added to this mixture, and the result was stirred for 2 hours after the temperature was raised to 170° C. After the reaction solution was cooled to room temperature, the insoluble solids were filtered through a filter paper, and the organic solvent was removed by vacuum distillation. After the obtained mixture was diluted with a small amount of o-dichlorobenzene, the result was loaded to a silica gel column, and o-dichlorobenzene and partially dissolved C$_{60}$ were removed while being developed with n-hexane. Subsequently, the result was purified while being developed with toluene. After the solvent was removed by vacuum distillation, solids were obtained by forming precipitates using methanol, and the solids were dried and mass-analyzed as a mixture. The mass analysis result of the compound is as follows.

MS: m/z n=1; 908, 909, n=2; 1096, n=3; 1285

The result was purified using column chromatography, and a compound of Chemical Formula 1-1-1 (420 mg, yield 12%) in which n=1 was prepared.

Preparation Example 2

Preparation of Chemical Formula 1-1-2

2-(3-Oxo-2,3-dihydro-1H-inden-1-yl)acetic acid was synthesized from 3-phenylalutaric acid with reference to a literature, Journal of the American Chemical Society, 1992, vol. 114, No. 6 p. 2181-2187.

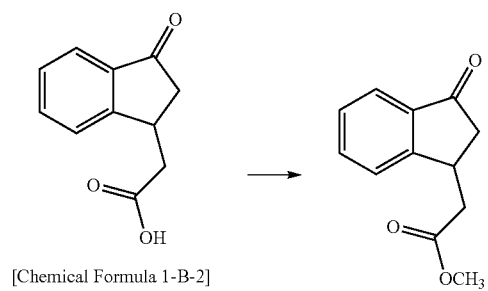

[Chemical Formula 1-B-2]

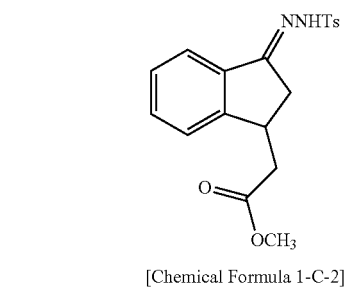

[Chemical Formula 1-C-2]

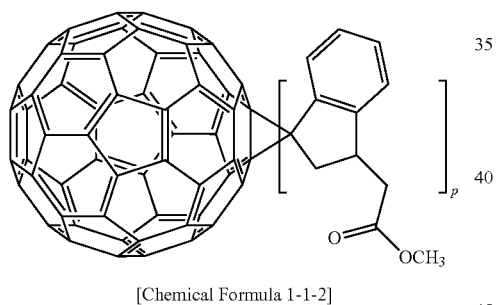

[Chemical Formula 1-1-2]

A compound of Chemical Formula 1-B-2 was prepared in the same manner as the compound of Chemical Formula 1-B-1 in Preparation Example 1-1-1, except that a 2-(3-oxo-2,3-dihydro-1H-inden-1-yl)acetic acid compound and methanol were used instead of 3-oxo-1-indancarboxylic acid and ethanol, respectively.

A compound of Chemical Formula 1-C-2 was synthesized in the same manner as the compound of Chemical Formula 1-C-1 in Preparation Example 1-1-1, except that the compound of Chemical Formula 1-B-2 was used instead of the compound of Chemical Formula 1-B-1.

A compound of Chemical Formula 1-1-2 was prepared in the same manner as the compound of Chemical Formula 1-1-1 in Preparation Example 1-1-1, except that the compound of Chemical Formula 1-C-2 was used instead of the compound of Chemical Formula 1-C-1.

The mass analysis result of this compound is as follows.

MS: m/z n=1; 908, 909

Preparation Example 3

Preparation of Chemical Formula 1-1-3

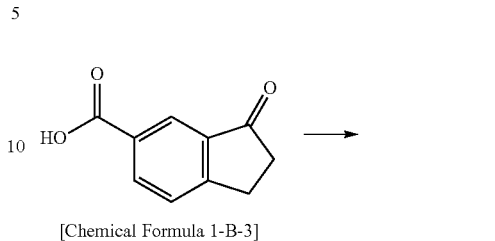

[Chemical Formula 1-B-3]

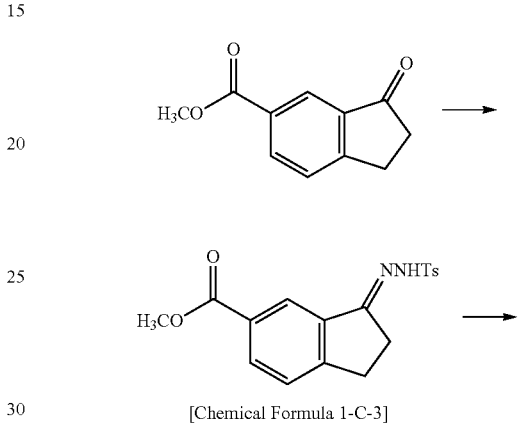

[Chemical Formula 1-C-3]

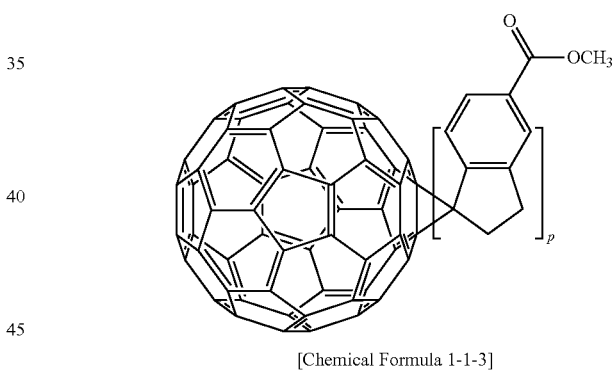

[Chemical Formula 1-1-3]

A compound of Chemical Formula 1-B-3 was prepared in the same manner as the compound of Chemical Formula 1-B-1 in Preparation Example 1-1-1, except that a 3-oxo-2,3-dihydro-1H-indene-5-carboxylic acid compound and methanol were used instead of 3-oxo-1-indancarboxylic acid and ethanol, respectively.

A compound of Chemical Formula 1-C-3 was synthesized in the same manner as the compound of Chemical Formula 1-C-1 in Preparation Example 1-1-1, except that the compound of Chemical Formula 1-B-3 was used instead of the compound of Chemical Formula 1-B-1.

A compound of Chemical Formula 1-1-3 was prepared in the same manner as the compound of Chemical Formula 1-1-1 in Preparation Example 1-1-1, except that the compound of Chemical Formula 1-C-3 was used instead of the compound of Chemical Formula 1-C-1.

The mass analysis result of this compound is as follows.

MS: m/z n=1; 894, 895

Preparation Example 4

Preparation of Chemical Formula 1-1-4

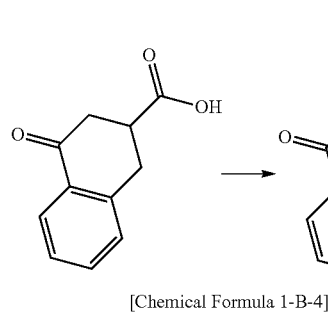

[Chemical Formula 1-B-4]

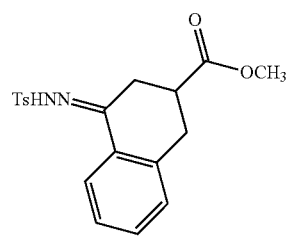

[Chemical Formula 1-C-4]

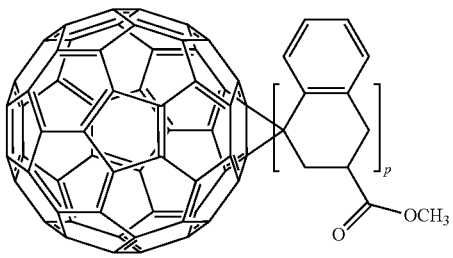

[Chemical Formula 1-1-4]

A compound of Chemical Formula 1-B-4 was prepared in the same manner as the compound of Chemical Formula 1-B-1 in Preparation Example 1-1-1, except that a 4-oxo-1,2,3,4-tetrahydronaphthalene-2-carboxylic acid compound and methanol were used instead of 3-oxo-1-indancarboxylic acid and ethanol, respectively.

A compound of Chemical Formula 1-C-4 was synthesized in the same manner as the compound of Chemical Formula 1-C-1 in Preparation Example 1-1-1, except that the compound of Chemical Formula 1-B-4 was used instead of the compound of Chemical Formula 1-B-1.

A compound of Chemical Formula 1-1-4 was prepared in the same manner as the compound of Chemical Formula 1-1-1 in Preparation Example 1-1-1, except that the compound of Chemical Formula 1-C-4 was used instead of the compound of Chemical Formula 1-C-1.

The mass analysis result of this compound is as follows.

MS: m/z n=1; 908, 909

Preparation Example 5

Preparation of Chemical Formula 1-1-5

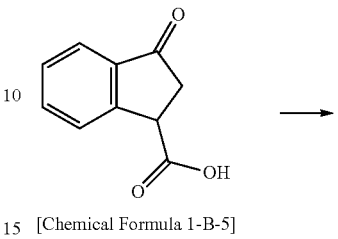

[Chemical Formula 1-B-5]

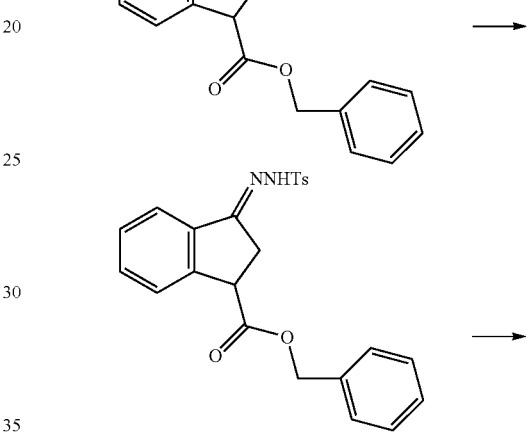

[Chemical Formula 1-C-5]

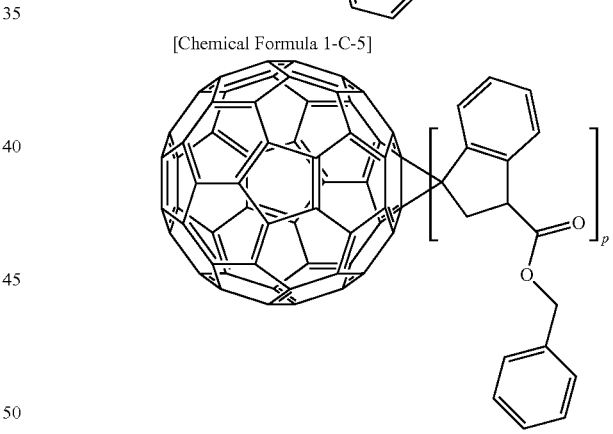

[Chemical Formula 1-1-5]

In a method for preparing the compound of Chemical Formula 1-B-1 in Preparation Example 1-1-1, a 3-oxo-1-indancarboxylic acid compound (10.0 g, 56.8 mmol), benzyl alcohol (30 mL), sulfuric acid ($H_2SO_4$) (1 mL) were placed, and the mixture was stirred for 24 hours while heating. The reaction temperature was lowered to room temperature, the solvent was vacuum distilled, passed through a silica gel layer, and benzyl-3-oxo-2,3-dihydro-1H-indene-1-carboxylate, a compound of Chemical Formula 1-B-5 (13.0 g, 86%), was obtained in a liquid state.

A compound of Chemical Formula 1-C-5 was synthesized in the same manner as the compound of Chemical Formula 1-C-1 in Preparation Example 1-1-1, except that the compound of Chemical Formula 1-B-5 was used instead of the compound of Chemical Formula 1-B-1.

A compound of Chemical Formula 1-1-5 was prepared in the same manner as the compound of Chemical Formula 1-1-1 in Preparation Example 1-1-1, except that the compound of Chemical Formula 1-C-5 was used instead of the compound of Chemical Formula 1-C-1.

The mass analysis result of this compound is as follows.
MS: m/z n=1; 970, 971

Preparation Example 6

Preparation of Chemical Formula 1-1-6

2-(3-oxo-2,3-dihydro-1H-indene-1-yl)acetic acid was synthesized from 3-phenylbutaric acid with reference to a literature, Journal of the American Chemical Society, 1992, vol. 114, No. 6 p. 2181-2187.

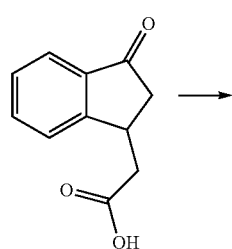

[Chemical Formula 1-B-6]

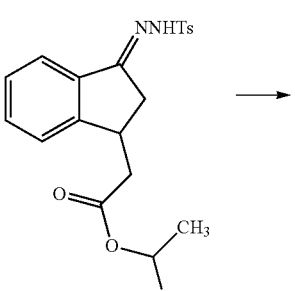

[Chemical Formula 1-C-6]

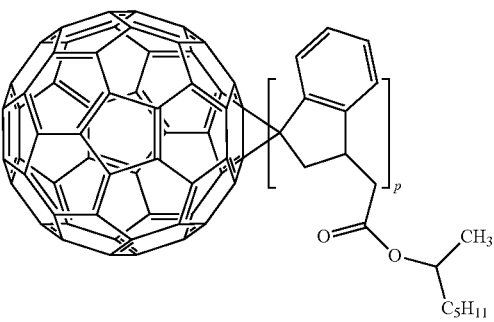

[Chemical Formula 1-1-6]

A compound of Chemical Formula 1-B-6 was prepared in the same manner as the compound of Chemical Formula 1-B-2 in Preparation Example 1-1-2, except that ethylhexyl alcohol instead of methanol was used with a 2-(3-oxo-2,3-dihydro-1H-inden-1-yl)acetic acid compound.

A compound of Chemical Formula 1-C-6 was synthesized in the same manner as the compound of Chemical Formula 1-C-1 in Preparation Example 1-1-1, except that the compound of Chemical Formula 1-B-6 was used instead of the compound of Chemical Formula 1-B-1.

A compound of Chemical Formula 1-1-6 was prepared in the same manner as the compound of Chemical Formula 1-1-1 in Preparation Example 1-1-1, except that the compound of Chemical Formula 1-C-6 was used instead of the compound of Chemical Formula 1-C-1.

The mass analysis result of this compound is as follows.
MS: m/z n=1; 978, 979

Preparation Example 7

Preparation of Chemical Formula 1-1-7

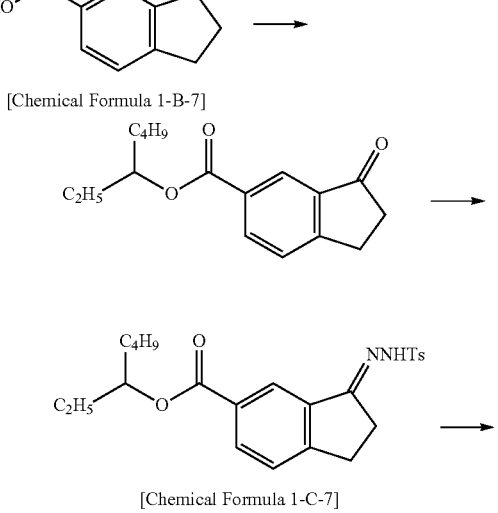

[Chemical Formula 1-B-7]

[Chemical Formula 1-C-7]

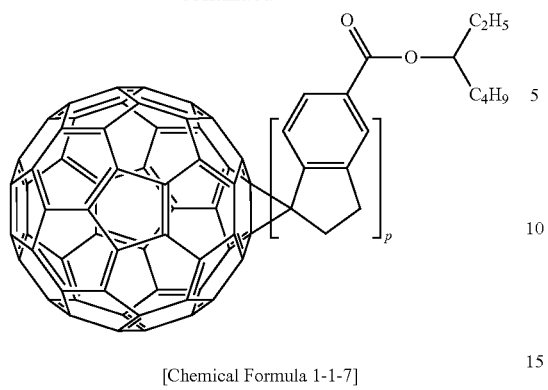

[Chemical Formula 1-1-7]

A compound of Chemical Formula 1-B-7 was prepared in the same manner as the compound of Chemical Formula 1-B-3 in Preparation Example 1-1-3, except that 3-heptanol instead of methanol was used with 3-oxo-2,3-dihydro-1H-indene-5-carboxylic acid.

A compound of Chemical Formula 1-C-7 was synthesized in the same manner as the compound of Chemical Formula 1-C-3 in Preparation Example 1-1-3, except that the compound of Chemical Formula 1-B-7 was used instead of the compound of Chemical Formula 1-B-3.

A compound of Chemical Formula 1-1-7 was prepared in the same manner as the compound of Chemical Formula 1-1-3 in Preparation Example 1-1-3, except that the compound of Chemical Formula 1-C-7 was used instead of the compound of Chemical Formula 1-C-3.

The mass analysis result of this compound is as follows.

MS: m/z n=1; 978, 979

Preparation Example 8

Preparation of Chemical Formula 1-1-8

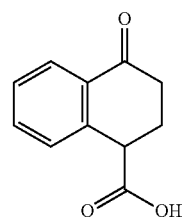

[Chemical Formula 1-B-8]

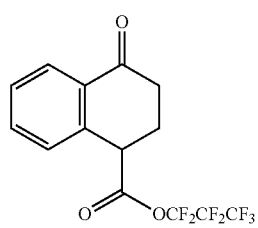

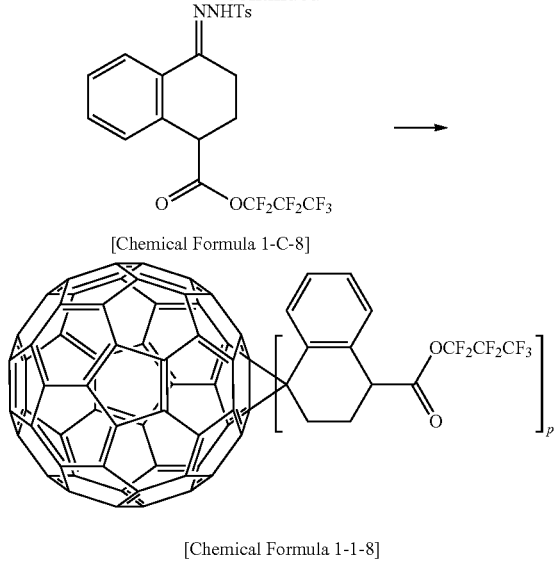

[Chemical Formula 1-C-8]

[Chemical Formula 1-1-8]

A compound of Chemical Formula 1-B-8 was prepared in the same manner as the compound of Chemical Formula 1-B-1 in Preparation Example 1-1-1, except that a 4-oxo-1,2,3,4,-tetrahydro-1-naphthalenecarboxylic acid compound and 2,2,3,3,4,4,4-heptafluoro-1-butanol were used instead of a 3-oxo-1-indancarboxylic acid compound and ethanol, respectively.

A compound of Chemical Formula 1-C-8 was synthesized in the same manner as the compound of Chemical Formula 1-C-1 in Preparation Example 1-1-1, except that the compound of Chemical Formula 1-B-8 was used instead of the compound of Chemical Formula 1-B-1.

A compound of Chemical Formula 1-1-8 was prepared in the same manner as the compound of Chemical Formula 1-1-1 in Preparation Example 1-1-1, except that the compound of Chemical Formula 1-C-8 was used instead of the compound of Chemical Formula 1-C-1.

The mass analysis result of this compound is as follows.

MS: m/z n=1; 1062, 1063

Preparation Example 9

Preparation of Chemical Formula 1-1-9

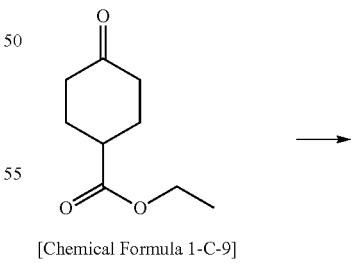

[Chemical Formula 1-C-9]

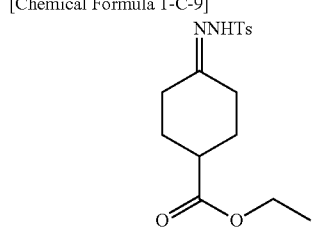

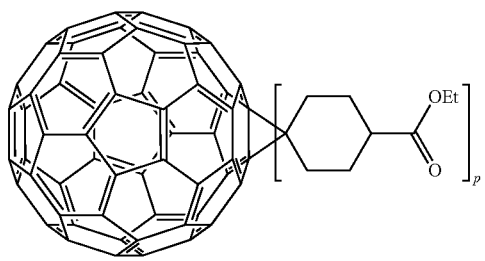

[Chemical Formula 1-1-9]

A compound of Chemical Formula 1-C-9 was prepared in the same manner as the compound of Chemical Formula 1-C-1 in Preparation Example 1-1-1, except that an ethyl-4-oxocyclohexanecarboxylate compound was used instead of the compound of Chemical Formula 1-B-1.

A compound of Chemical Formula 1-1-9 was prepared in the same manner as the compound of Chemical Formula 1-1-1 in Preparation Example 1-1-1, except that the compound of Chemical Formula 1-C-9 was used instead of the compound of Chemical Formula 1-C-1.

The mass analysis result of this compound is as follows.

MS: m/z n=1; 874

Preparation Example 10

Preparation of Chemical Formula 1-1-10

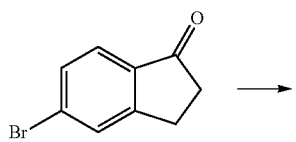

[Chemical Formula 1-B-10]

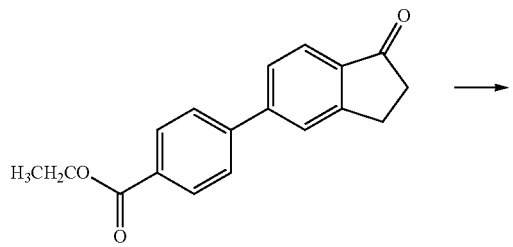

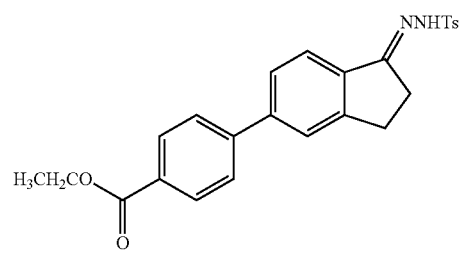

[Chemical Formula 1-C-10]

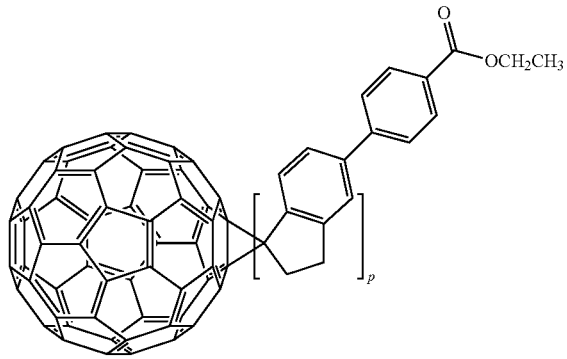

[Chemical Formula 1-1-10]

After a 5-bromoindanone compound (2.11 g, 10.0 mmol) and an 4-ethoxycarbonylphenylboronic acid pinacol ester compound (3.03 g, 11.0 mmol) were dissolved in tetrahydrofuran (60 mL), a 2M aqueous potassium carbonate solution (40 mL) and then tetrakistriphenylphosphino palladium (231 mg, 2 mol %) were added thereto, and the mixture was refluxed for 8 hours while stirring. The temperature was lowered to room temperature, and solids were formed by adding n-hexane to the reaction mixture, and the produced solids were dried after filtering. After the solids obtained as above were recrystallized with methylene chloride and ethanol, filtered and then dried, a compound of Chemical Formula 1-B-10 (1.84 g, 66%) was prepared.

MS: $[M+H]^+$=281

A compound of Chemical Formula 1-C-10 was prepared in the same manner as the compound of Chemical Formula 1-C-1 in Preparation Example 1-1-1, except that the compound of Chemical Formula 1-B-10 was used instead of the compound of Chemical Formula 1-B-1.

A compound of Chemical Formula 1-1-10 was synthesized in the same manner as the compound of Chemical Formula 1-1-1 in Preparation Example 1-1-1, except that the compound of Chemical Formula 1-C-10 was used instead of the compound of Chemical Formula 1-C-1

The mass analysis result of this compound is as follows.

MS: m/z n=1; 984

Preparation Example 11

Preparation of Chemical Formula 1-1-12

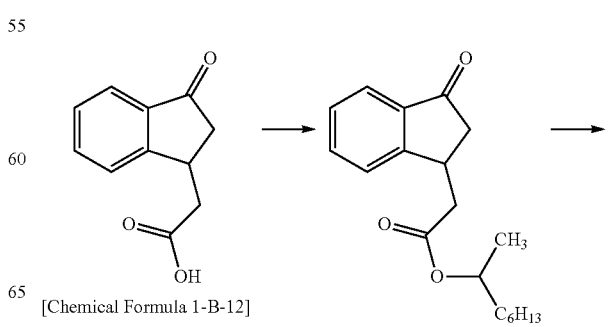

[Chemical Formula 1-B-12]

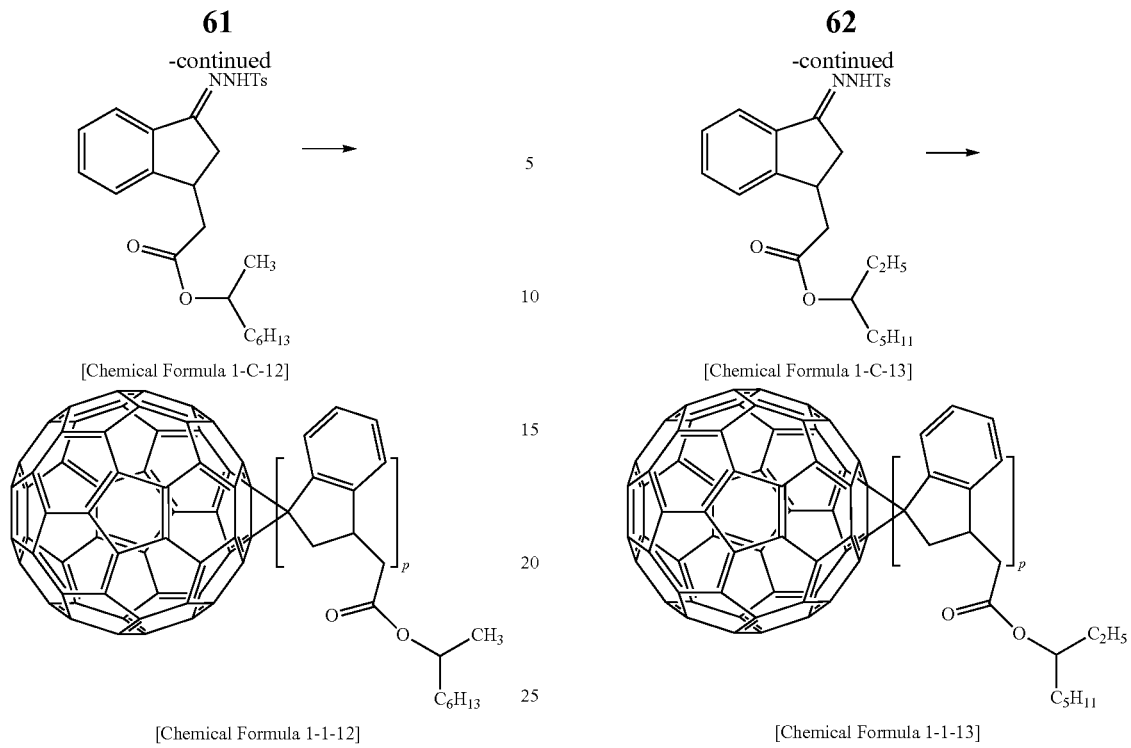

[Chemical Formula 1-C-12]

[Chemical Formula 1-1-12]

[Chemical Formula 1-C-13]

[Chemical Formula 1-1-13]

A compound of Chemical Formula 1-B-12 was prepared in the same manner as the compound of Chemical Formula 1-B-6 in Preparation Example 1-1-6, except that 2-octanol instead of methanol was used with a 2-(3-oxo-2,3-dihydro-1H-inden-1-yl)acetic acid compound.

A compound of Chemical Formula 1-C-12 was synthesized in the same manner as the compound of Chemical Formula 1-C-1 in Preparation Example 1-1-1, except that the compound of Chemical Formula 1-B-12 was used instead of the compound of Chemical Formula 1-B-1.

A compound of Chemical Formula 1-1-12 was prepared in the same manner as the compound of Chemical Formula 1-1-1 in Preparation Example 1-1-1, except that the compound of Chemical Formula 1-C-12 was used instead of the compound of Chemical Formula 1-C-1.

The mass analysis result of this compound is as follows.

MS: m/z n=1; 1006

A compound of Chemical Formula 1-B-13 was prepared in the same manner as the compound of Chemical Formula 1-B-6 in Preparation Example 1-1-6, except that 3-octanol instead of methanol was used with a 2-(3-oxo-2,3-dihydro-1H-inden-1-yl)acetic acid compound.

A compound of Chemical Formula 1-C-13 was synthesized in the same manner as the compound of Chemical Formula 1-C-1 in Preparation Example 1-1-1, except that the compound of Chemical Formula 1-B-13 was used instead of the compound of Chemical Formula 1-B-1.

A compound of Chemical Formula 1-1-13 was prepared in the same manner as the compound of Chemical Formula 1-1-1 in Preparation Example 1-1-1, except that the compound of Chemical Formula 1-C-13 was used instead of the compound of Chemical Formula 1-C-1.

The mass analysis result of this compound is as follows.

MS: m/z n=1; 1006

Preparation Example 12

Preparation of Chemical Formula 1-1-13

Preparation Example 13

Preparation of Chemical Formula 1-1-14

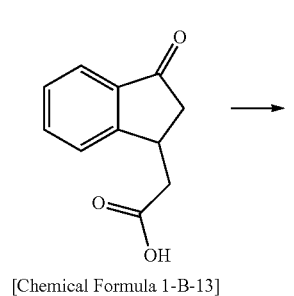

[Chemical Formula 1-B-13]

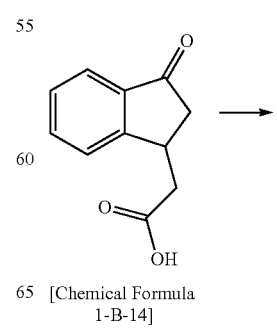

[Chemical Formula 1-B-14]

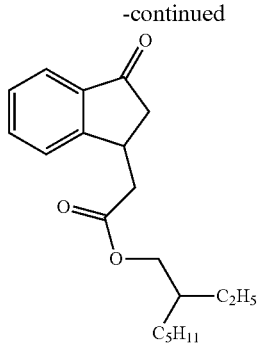

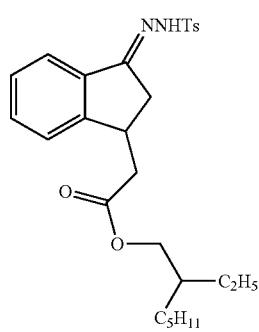

[Chemical Formula 1-C-14]

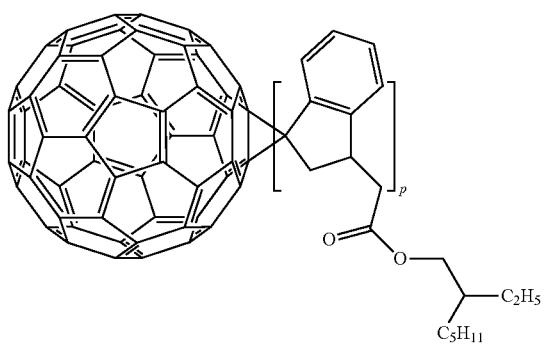

[Chemical Formula 1-1-14]

A compound of Chemical Formula 1-B-14 was prepared in the same manner as the compound of Chemical Formula 1-B-6 in Preparation Example 1-1-6, except that 2-ethyl-1-heptanol instead of methanol was used with a 2-(3-oxo-2,3-dihydro-1H-inden-1-yl)acetic acid compound.

A compound of Chemical Formula 1-C-14 was synthesized in the same manner as the compound of Chemical Formula 1-C-1 in Preparation Example 1-1-1, except that the compound of Chemical Formula 1-B-14 was used instead of the compound of Chemical Formula 1-B-1.

A compound of Chemical Formula 1-1-14 was prepared in the same manner as the compound of Chemical Formula 1-1-1 in Preparation Example 1-1-1, except that the compound of Chemical Formula 1-C-14 was used instead of the compound of Chemical Formula 1-C-1.

The mass analysis result of this compound is as follows.

MS: m/z n=1; 1020

Preparation Example 14

Preparation of Chemical Formula 1-1-15

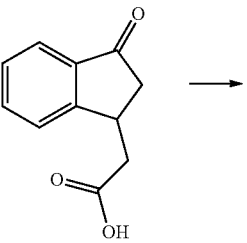

[Chemical Formula 1-B-15]

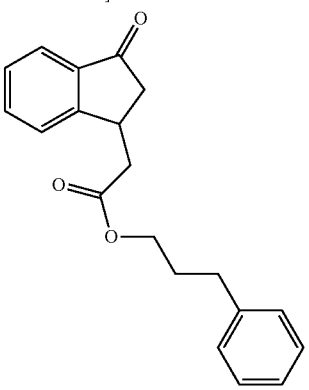

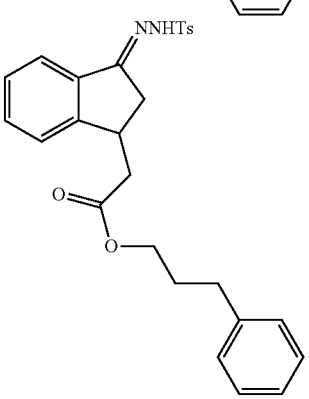

[Chemical Formula 1-C-15]

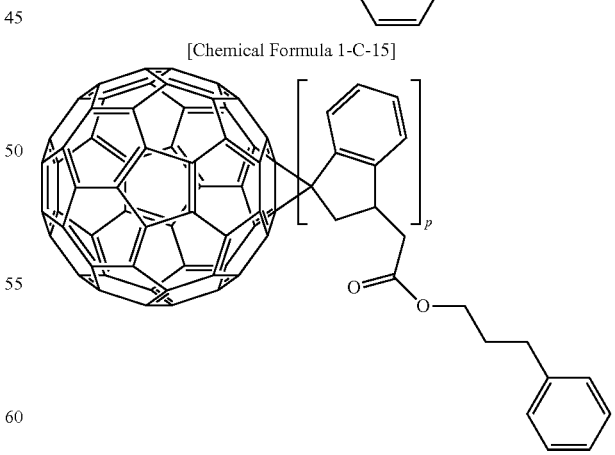

[Chemical Formula 1-1-15]

A compound of Chemical Formula 1-B-15 was prepared in the same manner as the compound of Chemical Formula 1-B-6 in Preparation Example 1-1-6, except that 3-phenyl- 1-propanol instead of methanol was used with a 2-(3-oxo-2,3-dihydro-1H-inden-1-yl)acetic acid compound.

A compound of Chemical Formula 1-C-15 was synthesized in the same manner as the compound of Chemical Formula 1-C-1 in Preparation Example 1-1-1, except that the compound of Chemical Formula 1-B-15 was used instead of the compound of Chemical Formula 1-B-1.

A compound of Chemical Formula 1-1-15 was prepared in the same manner as the compound of Chemical Formula 1-1-1 in Preparation Example 1-1-1, except that the compound of Chemical Formula 1-C-15 was used instead of the compound of Chemical Formula 1-C-1.

The mass analysis result of this compound is as follows.
MS: m/z n=1; 1012

Preparation Example 15

Preparation of Chemical Formula 1-1-16

A compound of Chemical Formula 1-B-16 was prepared in the same manner as the compound of Chemical Formula 1-B-6 in Preparation Example 1-1-6, except that 5'-hexyl-[2,2'-bithiophen]-5-yl)methanol instead of methanol was used with a 2-(3-oxo-2,3-dihydro-1H-inden-1-yl)acetic acid compound.

A compound of Chemical Formula 1-C-16 was synthesized in the same manner as the compound of Chemical Formula 1-C-1 in Preparation Example 1-1-1, except that the compound of Chemical Formula 1-B-16 was used instead of the compound of Chemical Formula 1-B-1.

A compound of Chemical Formula 1-1-16 was prepared in the same manner as the compound of Chemical Formula 1-1-1 in Preparation Example 1-1-1, except that the compound of Chemical Formula 1-C-16 was used instead of the compound of Chemical Formula 1-C-1.

The mass analysis result of this compound is as follows.
MS: m/z n=1; 1170

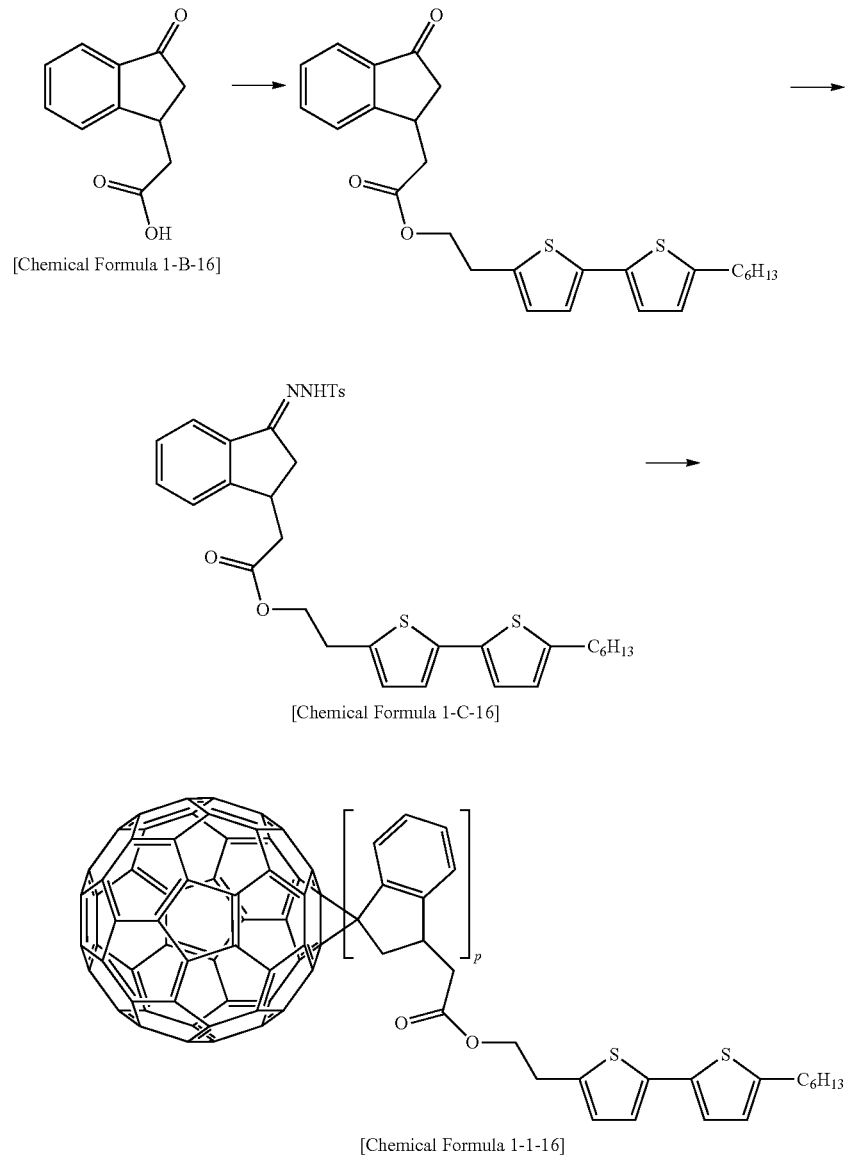

Preparation Example 16

Preparation of Chemical Formula 1-1-17

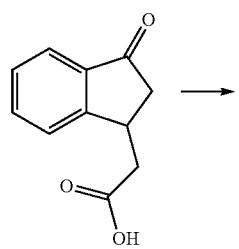

[Chemical Formula 1-B-17]

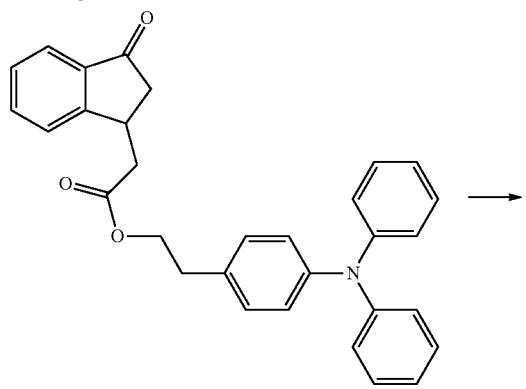

[Chemical Formula 1-C-17]

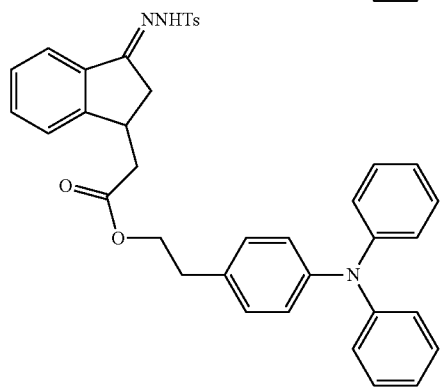

[Chemical Formula 1-1-17]

A compound of Chemical Formula 1-B-17 was prepared in the same manner as the compound of Chemical Formula 1-B-6 in Preparation Example 1-1-6, except that 2-(4-(diphenylamino)phenyl)ethan-1-ol instead of methanol was used with a 2-(3-oxo-2,3-dihydro-1H-inden-1-yl)acetic acid compound.

A compound of Chemical Formula 1-C-17 was synthesized in the same manner as the compound of Chemical Formula 1-C-1 in Preparation Example 1-1-1, except that the compound of Chemical Formula 1-B-17 was used instead of the compound of Chemical Formula 1-B-1.

A compound of Chemical Formula 1-1-17 was prepared in the same manner as the compound of Chemical Formula 1-1-1 in Preparation Example 1-1-1, except that the compound of Chemical Formula 1-C-17 was used instead of the compound of Chemical Formula 1-C-1.

The mass analysis result of this compound is as follows.

MS: m/z n=1; 1165

Preparation Example 17

Preparation of Chemical Formula 1-1-18

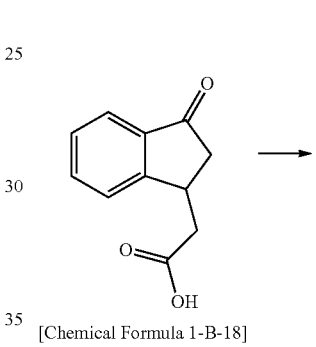

[Chemical Formula 1-B-18]

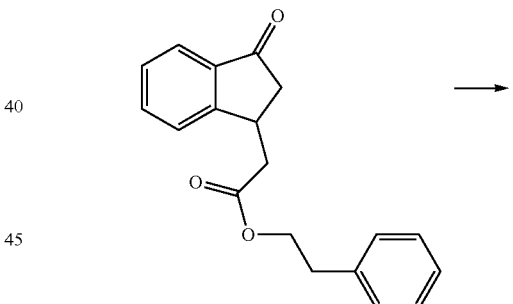

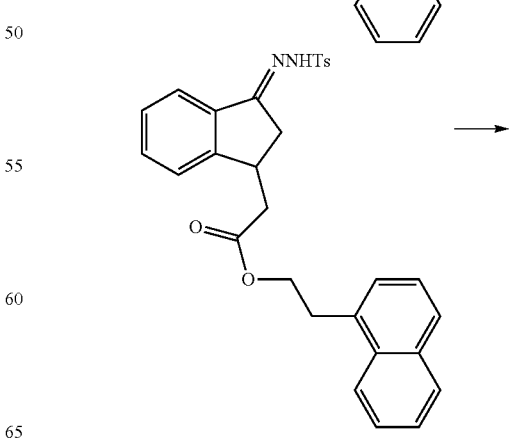

[Chemical Formula 1-C-18]

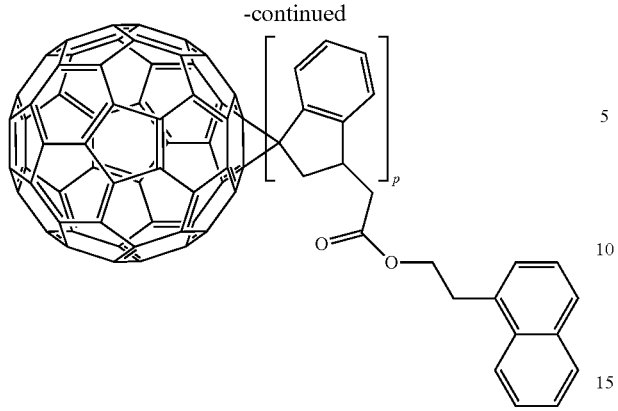

[Chemical Formula 1-1-18]

A compound of Chemical Formula 1-B-18 was prepared in the same manner as the compound of Chemical Formula 1-B-6 in Preparation Example 1-1-6, except that 2-(naphthalen-1-yl)ethan-1-ol instead of methanol was used with a 2-(3-oxo-2,3-dihydro-1H-inden-1-yl)acetic acid compound.

A compound of Chemical Formula 1-C-18 was synthesized in the same manner as the compound of Chemical Formula 1-C-1 in Preparation Example 1-1-1, except that the compound of Chemical Formula 1-B-18 was used instead of the compound of Chemical Formula 1-B-1.

A compound of Chemical Formula 1-1-18 was prepared in the same manner as the compound of Chemical Formula 1-1-1 in Preparation Example 1-1-1, except that the compound of Chemical Formula 1-C-18 was used instead of the compound of Chemical Formula 1-C-1.

MS: m/z n=1; 1048

Preparation Example 18

Preparation of Chemical Formula 1-1-19

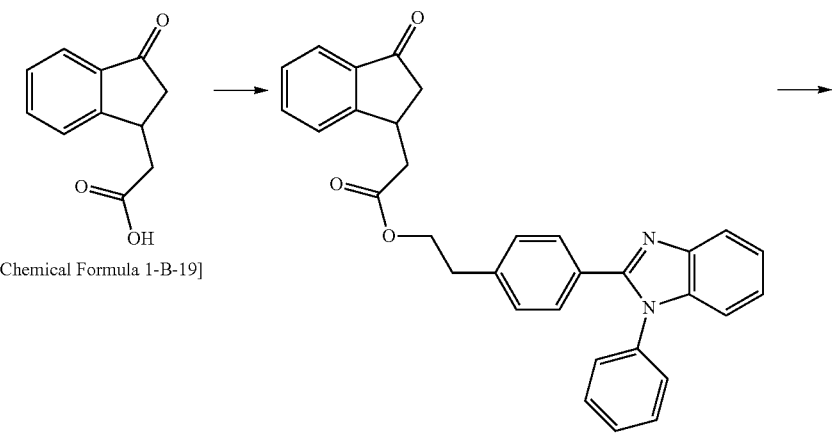

[Chemical Formula 1-B-19]

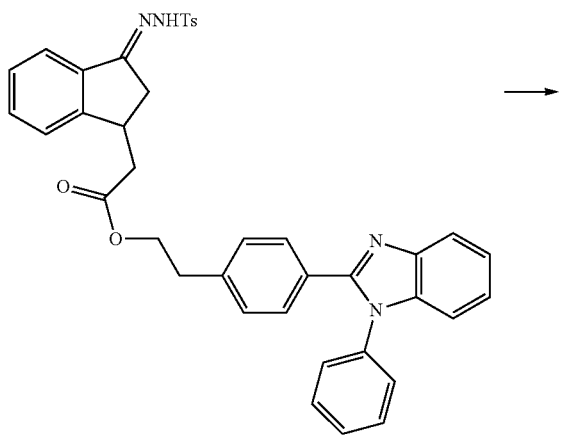

[Chemical Formula 1-C-19]

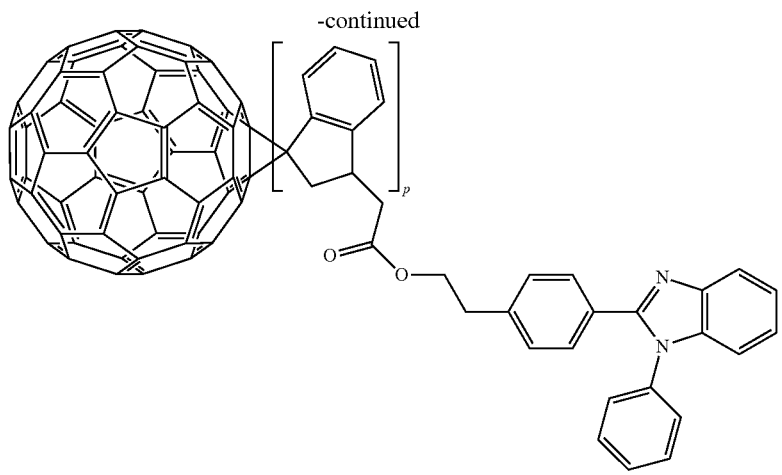

[Chemical Formula 1-1-19]

A compound of Chemical Formula 1-B-19 was prepared in the same manner as the compound of Chemical Formula 1-B-6 in Preparation Example 1-1-6, except that 2-(4-(1-phenyl-1H-benzo[d]imidazol-2-yl)phenyl)ethan-1-ol instead of methanol was used with a 2-(3-oxo-2,3-dihydro-1H-inden-1-yl)acetic acid compound.

A compound of Chemical Formula 1-C-19 was synthesized in the same manner as the compound of Chemical Formula 1-C-1 in Preparation Example 1-1-1, except that the compound of Chemical Formula 1-B-19 was used instead of the compound of Chemical Formula 1-B-1.

A compound of Chemical Formula 1-1-19 was prepared in the same manner as the compound of Chemical Formula 1-1-1 in Preparation Example 1-1-1, except that the compound of Chemical Formula 1-C-19 was used instead of the compound of Chemical Formula 1-C-1.

MS: m/z n=1; 1190

Preparation Example 19

Preparation of Chemical Formula 1-1-21

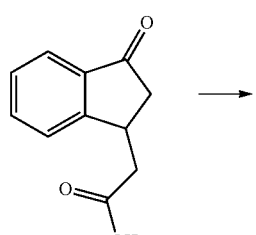

[Chemical Formula 1-B-21]

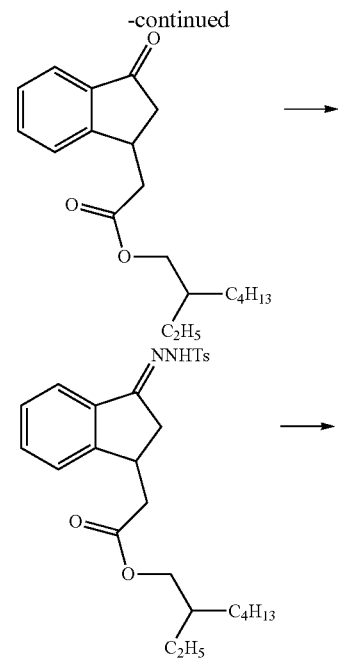

[Chemical Formula 1-C-21]

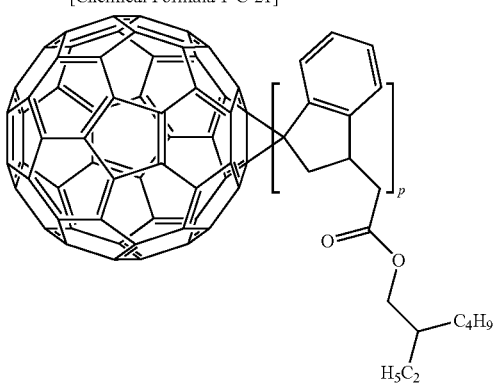

[Chemical Formula 1-1-21]

A compound of Chemical Formula 1-B-21 was prepared in the same manner as the compound of Chemical Formula 1-B-6 in Preparation Example 1-1-6, except that 2-ethyl-hexan-1-ol instead of methanol was used with a 2-(3-oxo-2,3-dihydro-1H-inden-1-yl)acetic acid compound.

A compound of Chemical Formula 1-C-21 was synthesized in the same manner as the compound of Chemical Formula 1-C-1 in Preparation Example 1-1-1, except that the compound of Chemical Formula 1-B-21 was used instead of the compound of Chemical Formula 1-B-1.

A compound of Chemical Formula 1-1-21 was prepared in the same manner as the compound of Chemical Formula 1-1-1 in Preparation Example 1-1-1, except that the compound of Chemical Formula 1-C-21 was used instead of the compound of Chemical Formula 1-C-1.

MS: m/z n=1; 1037

Preparation Example 20

Preparation of Chemical Formula 1-1-36

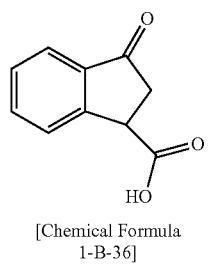

[Chemical Formula 1-B-36]

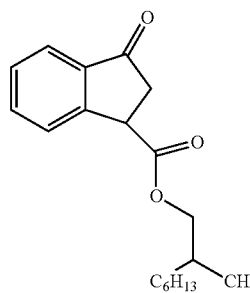

[Chemical Formula 1-C-36]

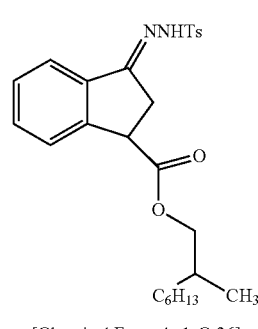

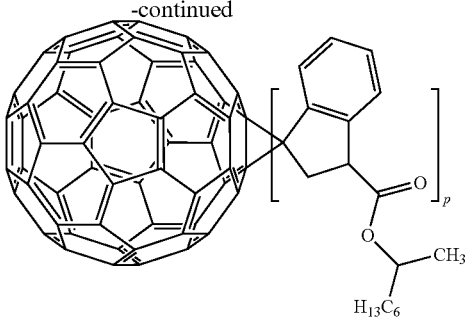

[Chemical Formula 1-1-36]

A compound of Chemical Formula 1-B-36 was prepared in the same manner as the compound of Chemical Formula 1-B-1 in Preparation Example 1-1-1, except that methyl-2-heptanol instead of ethanol was used with a 3-oxo-1-indan-carboxylic acid compound.

A compound of Chemical Formula 1-C-36 was synthesized in the same manner as the compound of Chemical Formula 1-C-1 in Preparation Example 1-1-1, except that the compound of Chemical Formula 1-B-36 was used instead of the compound of Chemical Formula 1-B-1.

A compound of Chemical Formula 1-1-36 was prepared in the same manner as the compound of Chemical Formula 1-1-1 in Preparation Example 1-1-1, except that the compound of Chemical Formula 1-C-36 was used instead of the compound of Chemical Formula 1-C-1.

The mass analysis result of this compound is as follows.

MS: m/z n=1; 1029

FIG. 6 is a diagram showing an MS spectrum of the fullerene derivative represented by Chemical Formula 1-1-36.

FIG. 7 is a diagram showing liquid chromatography (HPLC) of the fullerene derivative represented by Chemical Formula 1-1-36.

FIG. 8 is a diagram showing an NMR graph of the fullerene derivative represented by Chemical Formula 1-1-36.

Preparation Example 21

Preparation of Chemical Formula 1-1-44

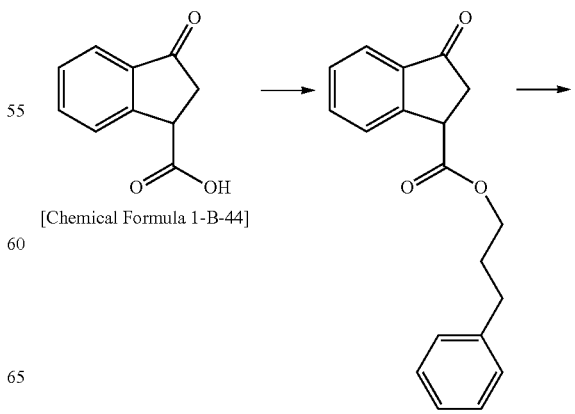

[Chemical Formula 1-B-44]

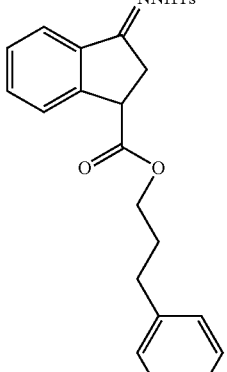

[Chemical Formula 1-C-44]

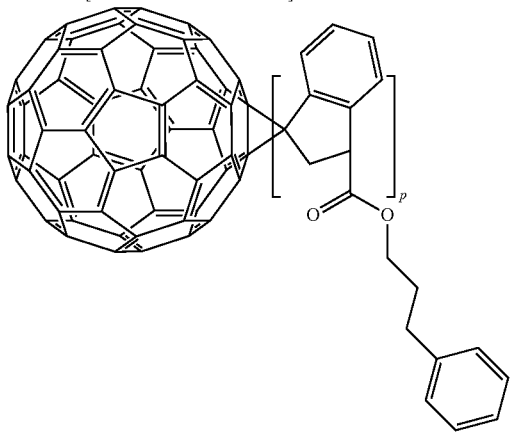

[Chemical Formula 1-1-44]

A compound of Chemical Formula 1-B-44 was prepared in the same manner as the compound of Chemical Formula 1-B-1 in Preparation Example 1-1-1, except that propanol instead of ethanol was used with a 3-oxo-1-indancarboxylic acid compound.

A compound of Chemical Formula 1-C-44 was synthesized in the same manner as the compound of Chemical Formula 1-C-1 in Preparation Example 1-1-1, except that the compound of Chemical Formula 1-B-44 was used instead of the compound of Chemical Formula 1-B-1.

A compound of Chemical Formula 1-1-44 was prepared in the same manner as the compound of Chemical Formula 1-1-1 in Preparation Example 1-1-1, except that the compound of Chemical Formula 1-C-44 was used instead of the compound of Chemical Formula 1-C-1.

The mass analysis result of this compound is as follows.
MS: m/z n=1; 1029

Preparation Example 2-1

Preparation of Chemical Formula 1-2-1

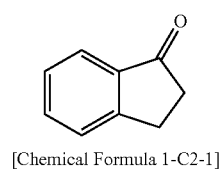

[Chemical Formula 1-C2-1]

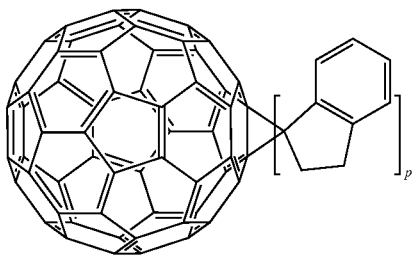

[Chemical Formula 1-2-1]

1-indanone (5.0 g, 37.83 mmol) was completely dissolved in 120 mL of methanol while heating. After p-toluenesulfonyl hydrazide (7.05 g, 37.83 mmol) was added to the mixed solution, the mixture was stirred for 4 hours while heating. After the reaction temperature was lowered to room temperature, the white solids formed were filtered and dried, and a compound of Chemical Formula 1-C2-1 (9.89 g, yield 87%) was prepared.

$C_{60}$ (5.0 g, 5 eq. 6.94 mmol), o-dichlorobenzene (ODCB, 100 mL), pyridine (20 mL) and sodium methoxide ($NaOCH_3$, 1.28 eq. 4.62 mmol, 0.24 g) were placed, and the mixture was stirred at 120° C. while heating. The compound of Chemical Formula 1-C2-1 (0.96 g, 3.85 mmol) was added to this mixture, and the result was stirred for 2 hours after the temperature was raised to 170° C. After the reaction solution was cooled to room temperature, the insoluble solids were filtered through a filter paper, and the organic solvent was removed by vacuum distillation. After the obtained mixture was diluted with a small amount of o-dichlorobenzene, the result was loaded to a silica gel column, and o-dichlorobenzene and partially dissolved $C_{60}$ were removed while being developed with n-hexane. Subsequently, the result was purified while being developed with toluene. After the solvent was removed by vacuum distillation, solids were obtained by forming precipitates using methanol, and the solids were dried to prepare a compound of Chemical Formula 1-2-1 (150 mg, yield 4.5%).

The mass analysis result of this compound is as follows.
MS: m/z n=1; 836, 837

Preparation Example 2-2

Preparation of Chemical Formula 1-2-2

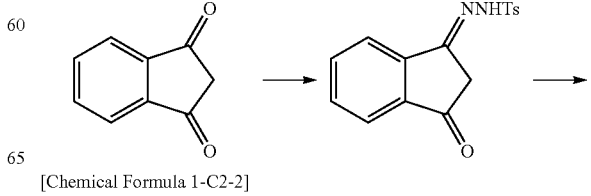

[Chemical Formula 1-C2-2]

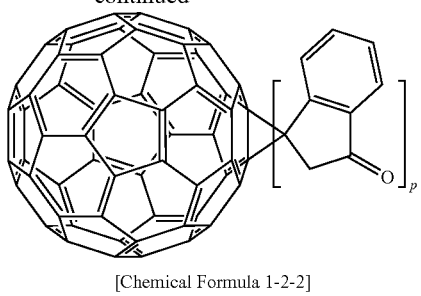

[Chemical Formula 1-2-2]

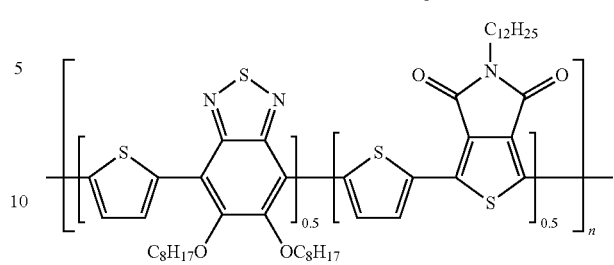

[Chemical Formula 2-1-1]

A compound of Chemical Formula 1-C2-2 was synthesized in the same manner as the compound of Chemical Formula 1-C2-1 in Preparation Example 1-2-1, except that 1,3-indandione was used instead of 1-indanone.

A compound of Chemical Formula 1-2-2 was prepared in the same manner as the compound of Chemical Formula 1-1-1 in Preparation Example 1-1-1, except that the compound of Chemical Formula 1-C2-2 was used instead of the compound of Chemical Formula 1-C2-1.

The mass analysis result of this compound is as follows.

MS: m/z n=1; 850, 851 n=2; 981, 981

In order to observe the electrochemical properties of the compounds prepared in the preparation examples, the oxidation/reduction properties of the compounds were observed using cyclic voltammetry (CV).

An AUTOLAB was used as a CV apparatus, and a 0.1 M solution made of tetrabutylammonium tetrafluoroborate ($Bu_4NBF_4$) in acetonitrile was used as an electrolyte, and the sample was dissolved selecting the solvent capable of dissolving the sample to a concentration of $10^{-3}$ M.

A glass carbon electrode was used as the working electrode, and a Pt and a Ag/AgCl electrode were used as a counter electrode and a reference electrode, and as a result, the LUMO energy levels of the compounds of Preparation Example 1 to Preparation Example 21 satisfying the structure of Chemical Formula 1 to Chemical Formula 5 were observed within the range of −3.6 eV to −4.0 eV. Therefore, the compounds have preferable LUMO energy levels, and have properties that can be used in an organic solar cell.

Meanwhile, when substituents that sufficiently pull the electrons are introduced, the LUMO energy level value may be lower than −4.0 eV. On the other hand, when substituents that sufficiently push the electrons are introduced, the LUMO energy level value may be made to be higher than −3.6 eV.

Fabrication of Organic Solar Cell and Measurement of its Characteristics

The photoelectric conversion properties of the organic solar cell includes fullerene derivative prepared in Preparation Example 1 to 21, Preparation Example 2-1 and 2-2 were measured under the condition of 100 mW/cm² (AM 1.5), and the results are shown in the following Table 1.

In addition, the organic solar cell was prepared using P3HT or a compound of the following Chemical Formula 2-1-1 as the electron donor material, and the results are shown in Table 1.

Example 1

Fabrication of Organic Solar Cell

A composite solution was prepared by dissolving the compound prepared in Preparation Example 1 and P3HT in the ratio of 4:1 in chlorobenzene (CB). Herein, the concentration was adjusted to 2.0 wt %, and the structure of the organic solar cell employed an ITO/PEDOT:PSS/photoactive layer/Al structure. The glass substrate coated with ITO was ultrasonic cleaned using distilled water, acetone and 2-propanol, and after the ITO surface was ozone treated for 10 minutes, the surface was spin-coated with PEDOT:PSS (baytrom P) to a thickness of 45 nm, and then heat treated for 10 minutes at 120° C. In order to coat the photoactive layer, the compound-PCBM composite solution was filtered using a PP syringe filter of 0.45 μm, then spin-coated, and deposited with Al to a thickness of 200 nm using a thermal evaporator under the vacuum of $3 \times 10^{-8}$ torr, and as a result, the organic solar cell was fabricated.

Example 2

Fabrication of Organic Solar Cell

The organic solar cell was fabricated in the same manner as in Example 1, except that the compound of Chemical Formula 1-1-2 prepared in Preparation Example 2 was used instead of the compound of Chemical Formula 1-1-1.

Example 3

Fabrication of Organic Solar Cell

The organic solar cell was fabricated in the same manner as in Example 1, except that the compound of Chemical Formula 1-1-3 prepared in Preparation Example 3 was used instead of the compound of Chemical Formula 1-1-1, and the ratio of P3HT and the fullerene derivative was 1:1.

Example 4

Fabrication of Organic Solar Cell

The organic solar cell was fabricated in the same manner as in Example 1, except that the compound of Chemical Formula 1-1-4 prepared in Preparation Example 4 was used instead of the compound of Chemical Formula 1-1-1, and the ratio of P3HT and the fullerene derivative was 1:3.

Example 5

Fabrication of Organic Solar Cell

The organic solar cell was fabricated in the same manner as in Example 1, except that the compound of Chemical Formula 1-1-5 prepared in Preparation Example 5 was used instead of the compound of Chemical Formula 1-1-1, and the ratio of P3HT and the fullerene derivative was 1:2.

Example 6

Fabrication of Organic Solar Cell

The organic solar cell was fabricated in the same manner as in Example 1, except that the compound of Chemical Formula 1-1-6 prepared in Preparation Example 6 was used instead of the compound of Chemical Formula 1-1-1, and the ratio of P3HT and the fullerene derivative was 1:1.

Example 7

Fabrication of Organic Solar Cell

The organic solar cell was fabricated in the same manner as in Example 1, except that the compound of Chemical Formula 1-1-7 prepared in Preparation Example 7 was used instead of the compound of Chemical Formula 1-1-1, and the ratio of P3HT and the fullerene derivative was 1:2.

Example 8

Fabrication of Organic Solar Cell

The organic solar cell was fabricated in the same manner as in Example 1, except that the compound of Chemical Formula 1-1-8 prepared in Preparation Example 8 was used instead of the compound of Chemical Formula 1-1-1, and the ratio of P3HT and the fullerene derivative was 1:2.

Example 9

Fabrication of Organic Solar Cell

The organic solar cell was fabricated in the same manner as in Example 1, except that the compound of Chemical Formula 1-1-9 prepared in Preparation Example 9 was used instead of the compound of Chemical Formula 1-1-1.

Example 10

Fabrication of Organic Solar Cell

The organic solar cell was fabricated in the same manner as in Example 1, except that the compound of Chemical Formula 1-1-10 prepared in Preparation Example 10 was used instead of the compound of Chemical Formula 1-1-1, and the ratio of P3HT and the fullerene derivative was 1:1.

Example 11

Fabrication of Organic Solar Cell

The organic solar cell was fabricated in the same manner as in Example 1, except that the compound of Chemical Formula 1-1-12 prepared in Preparation Example 11 was used instead of the compound of Chemical Formula 1-1-1, and the ratio of the compound of Chemical Formula 2-1-1 used instead of P3HT, and the fullerene derivative was 1:0.7.

Example 12

Fabrication of Organic Solar Cell

The organic solar cell was fabricated in the same manner as in Example 1, except that the compound of Chemical Formula 1-1-13 prepared in Preparation Example 12 was used instead of the compound of Chemical Formula 1-1-1, and the ratio of the compound of Chemical Formula 2-1-1 used instead of P3HT, and the fullerene derivative was 1:2.

Example 13

Fabrication of Organic Solar Cell

The organic solar cell was fabricated in the same manner as in Example 1, except that the compound of Chemical Formula 1-1-14 prepared in Preparation Example 13 was used instead of the compound of Chemical Formula 1-1-1, and the ratio of the compound of Chemical Formula 2-1-1 used instead of P3HT, and the fullerene derivative was 1:2.

Example 14

Fabrication of Organic Solar Cell

The organic solar cell was fabricated in the same manner as in Example 1, except that the compound of Chemical Formula 1-1-15 prepared in Preparation Example 14 was used instead of the compound of Chemical Formula 1-1-1, and the ratio of the compound of Chemical Formula 2-1-1 used instead of P3HT, and the fullerene derivative was 1:1.

Example 15

Fabrication of Organic Solar Cell

The organic solar cell was fabricated in the same manner as in Example 1, except that the compound of Chemical Formula 1-1-16 prepared in Preparation Example 15 was used instead of the compound of Chemical Formula 1-1-1, and the ratio of the compound of Chemical Formula 2-1-1 used instead of P3HT, and the fullerene derivative was 1:2.

Example 16

Fabrication of Organic Solar Cell

The organic solar cell was fabricated in the same manner as in Example 1, except that the compound of Chemical Formula 1-1-17 prepared in Preparation Example 16 was used instead of the compound of Chemical Formula 1-1-1, and the ratio of the compound of Chemical Formula 2-1-1 used instead of P3HT, and the fullerene derivative was 1:1.

Example 17

Fabrication of Organic Solar Cell

The organic solar cell was fabricated in the same manner as in Example 1, except that the compound of Chemical Formula 1-1-18 prepared in Preparation Example 17 was used instead of the compound of Chemical Formula 1-1-1, and the ratio of the compound of Chemical Formula 2-1-1 used instead of P3HT, and the fullerene derivative was 1:2.

Example 18

Fabrication of Organic Solar Cell

The organic solar cell was fabricated in the same manner as in Example 1, except that the compound of Chemical Formula 1-1-19 prepared in Preparation Example 18 was used instead of the compound of Chemical Formula 1-1-1, and the ratio of the compound of Chemical Formula 2-1-1 used instead of P3HT, and the fullerene derivative was 1:1.

Example 19

Fabrication of Organic Solar Cell

The organic solar cell was fabricated in the same manner as in Example 1, except that the compound of Chemical Formula 1-1-21 prepared in Preparation Example 19 was used instead of the compound of Chemical Formula 1-1-1, and the ratio of P3HT and the fullerene derivative was 1:2.

Example 20

Fabrication of Organic Solar Cell

The organic solar cell was fabricated in the same manner as in Example 1, except that the compound of Chemical Formula 1-1-21 prepared in Preparation Example 19 was used instead of the compound of Chemical Formula 1-1-1, and the ratio of the compound of Chemical Formula 2-1-1 used instead of P3HT, and the fullerene derivative was 1:1.

Example 21

Fabrication of Organic Solar Cell

The organic solar cell was fabricated in the same manner as in Example 1, except that the compound of Chemical Formula 1-1-36 prepared in Preparation Example 20 was used instead of the compound of Chemical Formula 1-1-1, and the ratio of the compound of Chemical Formula 2-1-1 used instead of P3HT, and the fullerene derivative was 1:2.

Example 22

Fabrication of Organic Solar Cell

The organic solar cell was fabricated in the same manner as in Example 1, except that the compound of Chemical Formula 1-1-44 prepared in Preparation Example 21 was used instead of the compound of Chemical Formula 1-1-1, and the ratio of P3HT and the fullerene derivative was 1:2.

Example 23

Fabrication of Organic Solar Cell

The organic solar cell was fabricated in the same manner as in Example 1, except that the compound of Chemical Formula 1-1-44 prepared in Preparation Example 21 was used instead of the compound of Chemical Formula 1-1-1, and the ratio of the compound of Chemical Formula 2-1-1 used instead of P3HT, and the fullerene derivative was 1:2.

Comparative Example 1

Fabrication of Organic Solar Cell

A composite solution was prepared by dissolving P3HT and PCBM in the ratio of 1:1 in 1,2-dichlorobenzene (DCB). Herein, the concentration was adjusted to 1.0 to 2.0 wt %, and the structure of the organic solar cell employed an ITO/PEDOT:PSS/photoactive layer/LiF/Al structure. The glass substrate coated with ITO was ultrasonic cleaned using distilled water, acetone and 2-propanol, and after the ITO surface was ozone treated for 10 minutes, the surface was spin-coated with PEDOT:PSS (baytrom P) to a thickness of 45 nm, and then heat treated for 10 minutes at 120° C. In order to coat the photoactive layer, the compound-PCBM composite solution was filtered using a PP syringe filter of 0.45 µm, then spin-coated and heat treated for 5 minutes at 120° C., and deposited with LiF to a thickness of 7 Å and then with Al to a thickness of 200 nm using a thermal evaporator under the vacuum of $3 \times 10^{-8}$ torr, and as a result, the organic solar cell was manufactured.

Comparative Example 2

Fabrication of Organic Solar Cell

A composite solution was prepared by dissolving P3HT and the compound of Chemical Formula 1-2-1 in the ratio of 1:1 in 1,2-dichlorobenzene (DCB). Herein, the concentration was adjusted to 1.0 to 2.0 wt %, and the structure of the organic solar cell employed an ITO/PEDOT:PSS/photoactive layer/LiF/Al structure. The glass substrate coated with ITO was ultrasonic cleaned using distilled water, acetone and 2-propanol, and after the ITO surface was ozone treated for 10 minutes, the surface was spin-coated with PEDOT:PSS (baytrom P) to a thickness of 45 nm, and then heat treated for 10 minutes at 120° C. In order to coat the photoactive layer, the P3HT-fullerene derivative composite solution was filtered using a PP syringe filter of 0.45 µm, then spin-coated and heat treated for 5 minutes at 120° C., and deposited with LiF to a thickness of 7 Å and then with Al to a thickness of 200 nm using a thermal evaporator under the vacuum of $3 \times 10^{-8}$ torr, and as a result, the organic solar cell was manufactured.

Comparative Example 3

Fabrication of Organic Solar Cell

A composite solution was prepared by dissolving P3HT and the compound of Chemical Formula 1-2-2 in the ratio of 1:2 in 1,2-dichlorobenzene (DCB). Herein, the concentration was adjusted to 1.0 to 2.0 wt %, and the structure of the organic solar cell employed an ITO/PEDOT:PSS/photoactive layer/LiF/Al structure. The glass substrate coated with ITO was ultrasonic cleaned using distilled water, acetone and 2-propanol, and after the ITO surface was ozone treated for 10 minutes, the surface was spin-coated with PEDOT:PSS (baytrom P) to a thickness of 45 nm, and then heat treated for 10 minutes at 120° C. In order to coat the photoactive layer, the P3HT-fullerene derivative composite solution was filtered using a PP syringe filter of 0.45 µm, then spin-coated and heat treated for 5 minutes at 120° C., and deposited with LiF to a thickness of 7 Å and then with Al to a thickness of 200 nm using a thermal evaporator under the vacuum of $3\times10^{-8}$ torr, and as a result, the organic solar cell was manufactured.

TABLE 1

| | Photoactive Layer (P3HT:Compound) | $V_{OC}$ (V) | $J_{SC}$ (mA/cm$^2$) | FF | PCE (%) |
|---|---|---|---|---|---|
| Example 1 | P3HT:Chemical Formula 1-1-1 = 1:4 | 0.63 | 8.90 | 0.54 | 3.03 |
| Example 2 | P3HT:Chemical Formula 1-1-2 = 1:4 | 0.50 | 10.51 | 0.62 | 3.26 |
| Example 3 | P3HT:Chemical Formula 1-1-3 = 1:1 | 0.43 | 4.46 | 0.37 | 0.71 |
| Example 4 | P3HT:Chemical Formula 1-1-4 = 1:3 | 0.69 | 11.67 | 0.30 | 2.42 |
| Example 5 | P3HT:Chemical Formula 1-1-5 = 1:2 | 0.64 | 6.37 | 0.52 | 2.12 |
| Example 6 | P3HT:Chemical Formula 1-1-6 = 1:1 | 0.62 | 6.26 | 0.54 | 2.10 |
| Example 7 | P3HT:Chemical Formula 1-1-7 = 1:2 | 0.53 | 10.78 | 0.50 | 2.86 |
| Example 8 | P3HT:Chemical Formula 1-1-8 = 1:2 | 0.63 | 4.10 | 0.66 | 1.70 |
| Example 9 | P3HT:Chemical Formula 1-1-9 = 1:4 | 0.42 | 8.30 | 0.81 | 2.81 |
| Example 10 | P3HT:Chemical Formula 1-1-10 = 1:1 | 0.61 | 3.97 | 0.601 | 1.46 |
| Example 11 | Chemical Formula 2-1-1:Chemical Formula 1-1-12 = 1:0.7 | 0.91 | 9.66 | 0.52 | 4.57 |
| Example 12 | Chemical Formula 2-1-1:Chemical Formula 1-1-13 = 1:2 | 0.99 | 9.01 | 0.49 | 4.37 |
| Example 13 | Chemical Formula 2-1-1:Chemical Formula 1-1-14 = 1:2 | 0.91 | 9.74 | 0.51 | 4.52 |
| Example 14 | Chemical Formula 2-1-1:Chemical Formula 1-1-15 = 1:1 | 1.03 | 9.67 | 0.42 | 4.18 |
| Example 15 | Chemical Formula 2-1-1:Chemical Formula 1-1-16 = 1:2 | 0.88 | 9.86 | 0.48 | 4.16 |
| Example 16 | Chemical Formula 2-1-1:Chemical Formula 1-1-17 = 1:1 | 0.93 | 8.30 | 0.43 | 3.32 |
| Example 17 | Chemical Formula 2-1-1:Chemical Formula 1-1-18 = 1:2 | 0.82 | 8.86 | 0.54 | 3.92 |
| Example 18 | Chemical Formula 2-1-1:Chemical Formula 1-1-19 = 1:1 | 0.99 | 9.30 | 0.47 | 4.33 |
| Example 19 | P3HT:Chemical Formula 1-1-21 = 1:2 | 0.63 | 8.56 | 0.56 | 3.02 |
| Example 20 | Chemical Formula 2-1-1:Chemical Formula 1-1-21 = 1:1 | 1.01 | 7.48 | 0.62 | 4.68 |
| Example 21 | Chemical Formula 2-1-1:Chemical Formula 1-1-36 = 1:1 | 1.09 | 6.98 | 0.65 | 4.94 |
| Example 22 | P3HT:Chemical Formula 1-1-44 = 1:2 | 0.53 | 7.91 | 0.59 | 2.47 |
| Example 23 | Chemical Formula 2-1-1:Chemical Formula 1-1-44 = 1:2 | 0.98 | 9.86 | 0.54 | 5.21 |
| Comparative Example 1 | P3HT:PC$_{61}$BM = 1:1 | 0.46 | 10.04 | 0.47 | 2.17 |
| Comparative Example 2 | P3HT:Chemical Formula 1-2-1 = 1:2 | 0.42 | 0.12 | 0.21 | 0.58 |
| Comparative Example 3 | P3HT:Chemical Formula 1-2-2 = 1:0.7 | 0.38 | 0.34 | 0.28 | 0.04 |

As seen in Table 1, the compound of Chemical Formula 1-2-1 used in Comparative Example 2 does not include substituents that increase the solubility or improve the morphology in the pentagonal or benzene ring, and the compound of Chemical Formula 1-2-2 used in Comparative Example 3 has decreased solubility due to the carbonyl group in the pentagonal structure and was not sufficiently mixed with P3HT. As a result, favorable morphology is not formed and this may result in the efficiency decrease.

The present specification used only P3HT or the compound of Chemical Formula 2-1-1 as the electron donor material, however, the electron donor material is not limited thereto, and as long as it is a compound capable of being used in a solution process, the electron donor material is not limited to polymer compounds and unimolecular compounds.

According to one embodiment of the present specification, the examples are provided for a device with a normal structure only, however, the examples may be provided for a device with an inverted structure as well.

While examples of the present invention have been described above, it will be apparent that the scope of the present invention is not limited thereto since these specific descriptions are provided to instruct the scope of the present invention for those skilled in the art. Therefore, the actual scope of the present invention is defined by the appended claims and their equivalents.

The invention claimed is:
1. A fullerene derivative of any one of the following Chemical Formulae 2 to 5:

[Chemical Formula 2]

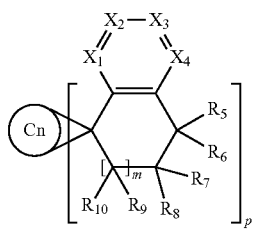

[Chemical Formula 3]

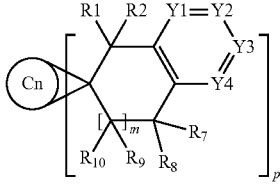

[Chemical Formula 4]

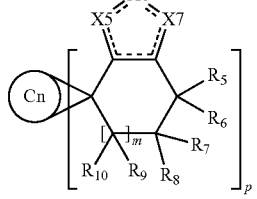

[Chemical Formula 5]

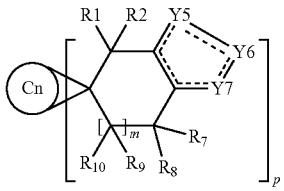

wherein:
m is an integer of 0 or 1;
p is an integer of 1 to 3;
when p is 2 or greater, the structures within the parenthesis are the same as or different from each other;
Cn is fullerene of C$_{60}$ to C$_{84}$;

R1, R2 and R5 to R10 are the same as or different from each other, and each independently hydrogen; deuterium a halogen group; a nitrile group; a nitro group; an imide group; an amide group; a hydroxyl group; an ester group; a carbonyl group; a substituted or unsubstituted alkyl group; a substituted or unsubstituted cycloalkyl group; a substituted or unsubstituted alkoxy group; a substituted or unsubstituted arylalkyl group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted aryl group; a substituted or unsubstituted fluorenyl group; a substituted or unsubstituted carbazole group; or a substituted or unsubstituted heteroring group that includes one or more of N, O and S atoms; or adjacent substituents are bonded to each other to form a substituted or unsubstituted hydrocarbon ring; a substituted or unsubstituted heteroring that includes one or more of N, O and S atoms, or substituents within the same carbon form a spiro bond; a carbonyl group; a substituted or unsubstituted imine group; or a substituted or unsubstituted alkenyl group;

X1 to X4 are the same as or different from each other, and each independently CRx; or N;

Y1 to Y4 are the same as or different from each other, and each independently CRy; or N;

X5 to X7 are the same as or different from each other, and each independently CRx'; S; or NRx';

Y5 to Y7 are the same as or different from each other, and each independently Cry', S; or NRy'; and Rx, Ry, Rx' and Ry' are the same as or different from each other, and each independently hydrogen, deuterium, a halogen group, a nitrile group, a nitro group, an imide group, an amide group, a hydroxyl group, an ester group, a carbonyl group, a substituted or unsubstituted alkyl group, a substituted or unsubstituted cycloalkyl group, a substituted or unsubstituted alkoxy group, a substituted or unsubstituted arylalkyl group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted boron group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorenyl group, a substituted or unsubstituted carbazole group, or a substituted or unsubstituted heteroring group that includes one or more of N, O and S atoms, or adjacent substituents are bonded to each other to form a substituted or unsubstituted hydrocarbon ring, or a heteroring that includes one or more of N, O and S atoms, or a spiro bond;

when m is 0, at least one of the substituents of the ring formed by the adjacent substituents of R1, R2, R5 to R8 and R1, R2, R5 to R8, Rx, Ry, Rx' and Ry' is -(L)a-(M)b;

when m is 1, at least one of the substituents of the ring formed by the adjacent substituents of R1, R2, R5 to R10 and R1, R2, R5 to R10, Rx, Ry, Rx' and Ry' is -(L)a-(M)b;

a is an integer of 0 or 1;

bis an integer of 1 or 2;

L is a substituted or unsubstituted alkylene group having 1 to 20 carbon atoms; a substituted or unsubstituted divalent ether group having 1 to 20 carbon atoms; a substituted or unsubstituted divalent aromatic hydrocarbon ring having 5 to 30 carbon atoms; or a divalent aromatic heteroring that includes one or more of N, O and S atoms;

M is

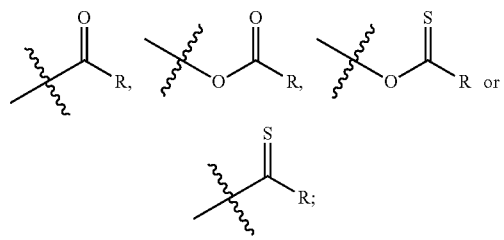

and

R is hydrogen, deuterium, a halogen group, a nitrile group, a nitro group, an imide group, an amide group, a hydroxyl group, an ester group, a carbonyl group, a substituted or unsubstituted alkyl group, a substituted or unsubstituted cycloalkyl group, a substituted or unsubstituted alkoxy group, a substituted or unsubstituted cycloalkoxy group, a substituted or unsubstituted arylalkyl group, a substituted or unsubstituted arylalkyloxy group, a substituted or unsubstituted aryloxy group, a substituted or unsubstituted alkylthioxy group, a substituted or unsubstituted arylthioxy group, a substituted or unsubstituted alkylsulfoxy group, a substituted or unsubstituted arylsulfoxy group, a substituted or unsubstituted alkenyl group, a substituted or unsubstituted silyl group, a substituted or unsubstituted silyloxy group, a substituted or unsubstituted alkylamine group, a substituted or unsubstituted aralkylamine group, a substituted or unsubstituted arylamine group, a substituted or unsubstituted heteroarylamine group, a substituted or unsubstituted aryl group, a substituted or unsubstituted fluorenyl group, a substituted or unsubstituted carbazole group, a substituted or unsubstituted heteroaryl group that includes one or more of N, O and S atoms, or a substituted or unsubstituted heteroaryloxy group that includes one or more of N, O and S atoms.

2. The fullerene derivative of claim 1, wherein m is 0.

3. The fullerene derivative of claim 1, wherein m is 1.

4. The fullerene derivative of claim 1, wherein at least one of the substituents of the hydrocarbon ring formed by the adjacent substituents of R1, R2, R5 to R10, and R1, R2, R5 to R8, Rx, Ry, Rx' and Ry' is -(L)a-(M)b.

5. The fullerene derivative of claim 1, wherein a is an integer of 0 or 1; and

L is a substituted or unsubstituted alkylene group having 1 to 4 carbon atoms; or a substituted or unsubstituted phenylene group.

6. The fullerene derivative of claim 1, wherein R is a substituted or unsubstituted alkyl group having 1 to 20 carbon atoms, a substituted or unsubstituted alkoxy group having 1 to 20 carbon atoms, a substituted or unsubstituted cycloalkyl group having 3 to 60 carbon atoms, a substituted or unsubstituted cycloalkoxy group having 3 to 60 carbon atoms, a substituted or unsubstituted arylalkoxy group having 7 to 50 carbon atoms, a substituted or unsubstituted aryl group having 6 to 60 carbon atoms, a substituted or unsubstituted aryloxy group having 6 to 60 carbon atoms, a substituted or unsubstituted heteroaryl group having 2 to 60 carbon atoms, which includes one or more of N, O and S atoms, or a substituted or unsubstituted heteroaryloxy group having 2 to 60 carbon atoms, which includes one or more of N, O and S atoms.

7. The fullerene derivative of claim 1, wherein R is a substituted or unsubstituted alkyl group having 1 to 20 carbon atoms, a substituted or unsubstituted alkoxy group having 1 to 20 carbon atoms, a substituted or unsubstituted arylalkoxy group having 7 to 50 carbon atoms, a substituted or unsubstituted aryl group having 6 to 60 carbon atoms, or a substituted or unsubstituted heteroaryloxy group having 2 to 60 carbon atoms, which includes one or more of N, O and S atoms.

8. The fullerene derivative of claim 7, wherein the alkyl group, the alkoxy group, the arylalkoxy group, the aryl group and the heteroaryloxy group are unsubstituted or substituted with a halogen group, a cyano group, a substituted or unsubstituted aryl group having 6 to 30 carbon atoms, a substituted or unsubstituted arylamine group, or a substituted or unsubstituted heteroring group having 2 to 30 carbon atoms, which includes one or more of N, O and S atoms.

9. The fullerene derivative of claim 1, wherein:
m is an integer of 0 or 1;
at least one of the substituents of the hydrocarbon ring formed by the adjacent substituents of R1, R2, R5 to R10; and R1, R2, R5 to R8, Rx, Ry, Rx' and Ry' is -(L)a-(M)b;
a is 0 or 1;
L is a substituted or unsubstituted alkylene group having 1 to 20 carbon atoms; or a substituted or unsubstituted divalent aromatic hydrocarbon ring having 5 to 30 carbon atoms;
b is an integer of 1 or 2;
M is

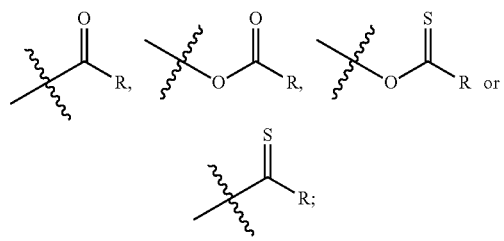

and

R is a substituted or unsubstituted alkyl group having 1 to 20 carbon atoms; a substituted or unsubstituted alkoxy group having 1 to 20 carbon atoms; a substituted or unsubstituted cycloalkyl group having 3 to 60 carbon atoms; a substituted or unsubstituted cycloalkoxy group having 3 to 60 carbon atoms; a substituted or unsubstituted arylalkoxy group having 7 to 50 carbon atoms; a substituted or unsubstituted aryl group having 6 to 60 carbon atoms; a substituted or unsubstituted aryloxy group having 6 to 60 carbon atoms; a substituted or unsubstituted heteroaryl group having 2 to 60 carbon atoms, which includes one or more of N, O and S atoms; or a substituted or unsubstituted heteroaryloxy group having 2 to 60 carbon atoms, which includes one or more of N, O and S atoms.

10. A fullerene derivative of any one of the following Formulae 1-1-1 to 1-1-54:

[Formula 1-1-1]

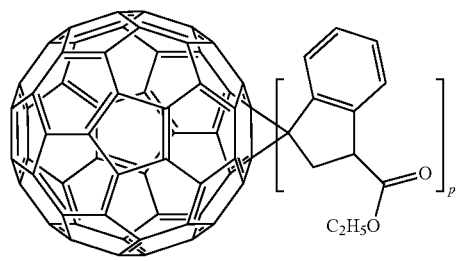

[Formula 1-1-2]

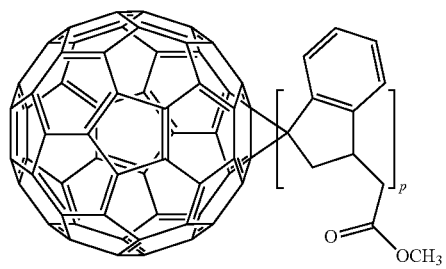

[Formula 1-1-3]

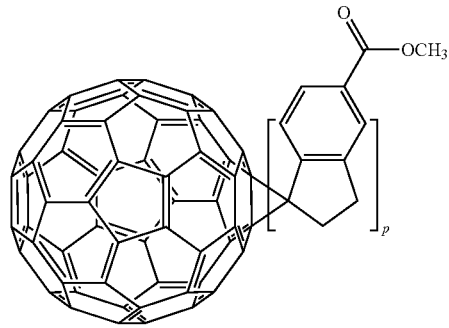

[Formula 1-1-4]

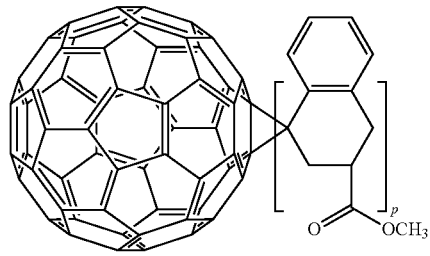

[Formula 1-1-5] 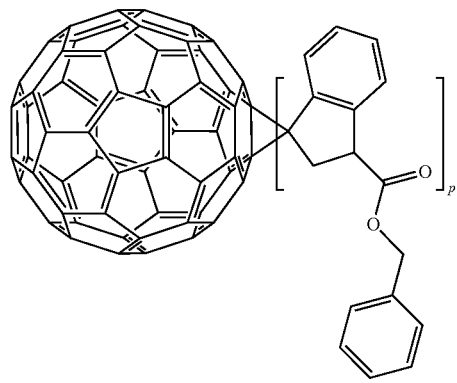
[Formula 1-1-6] 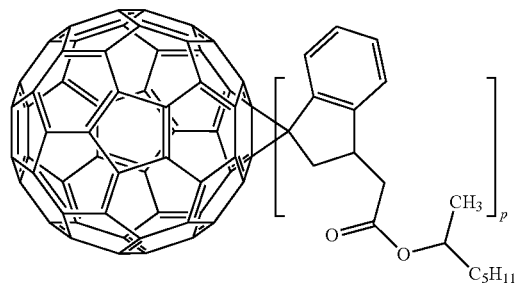
[Formula 1-1-7] 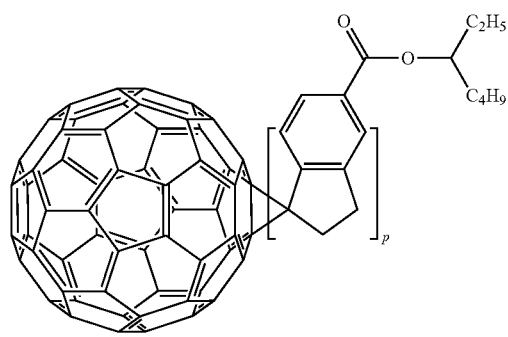
[Formula 1-1-8] 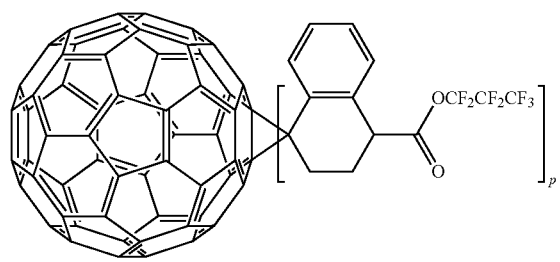
[Formula 1-1-9] 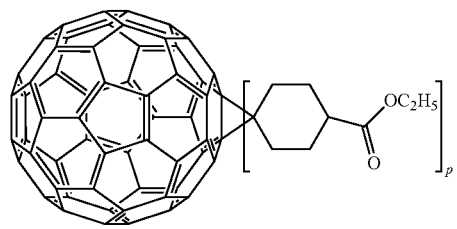
[Formula 1-1-10] 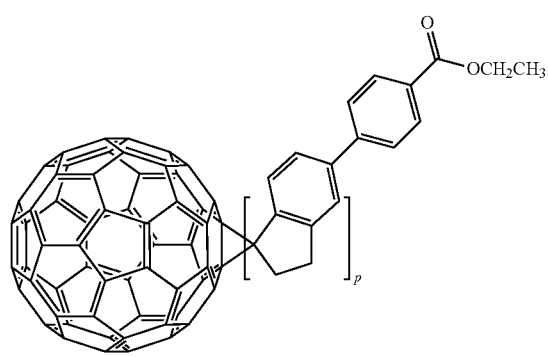
[Formula 1-1-11] 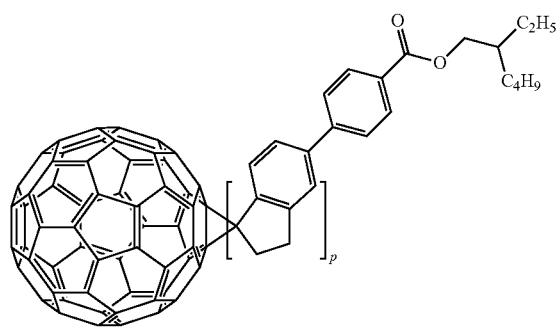
[Formula 1-1-12] 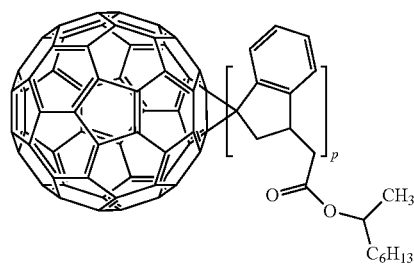

-continued
[Formula 1-1-13]
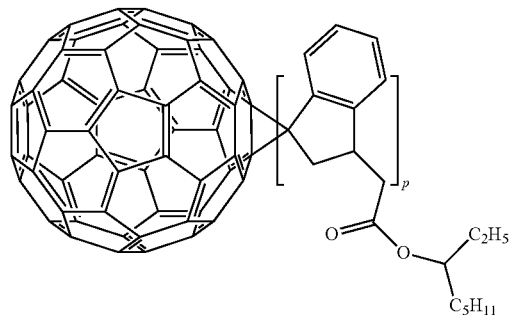
[Formula 1-1-14]
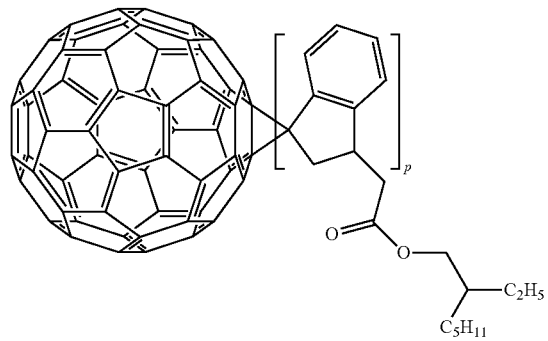
[Formula 1-1-15]
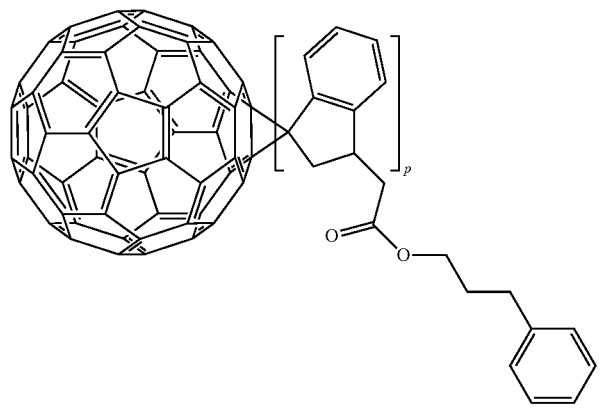
[Formula 1-1-16]
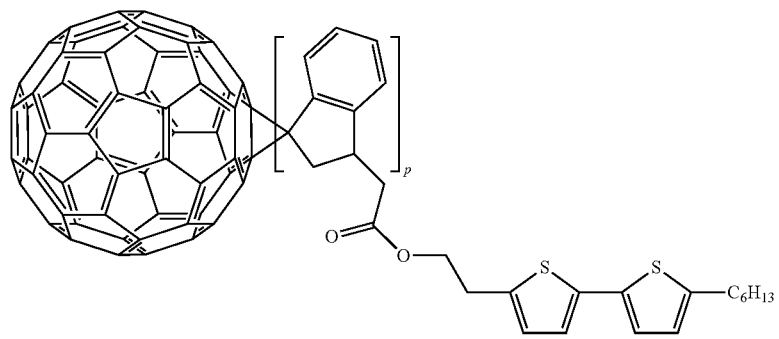
[Formula 1-1-17]
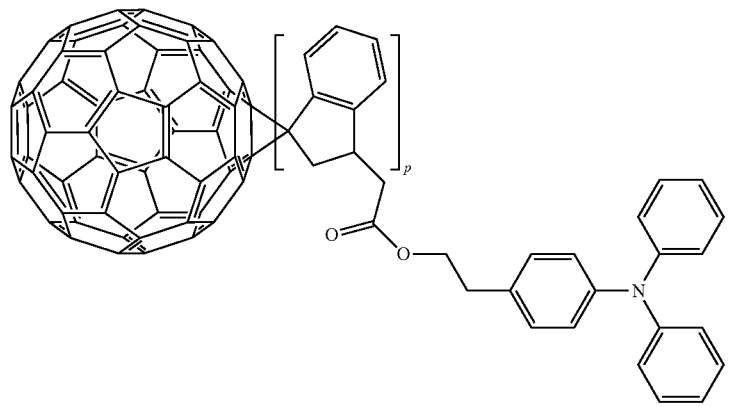

[Formula 1-1-18]
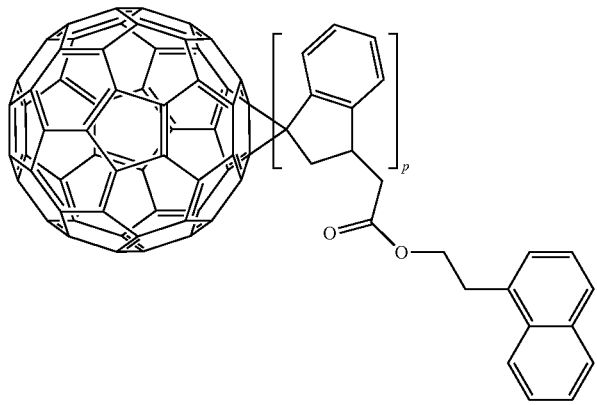
[Formula 1-1-19]
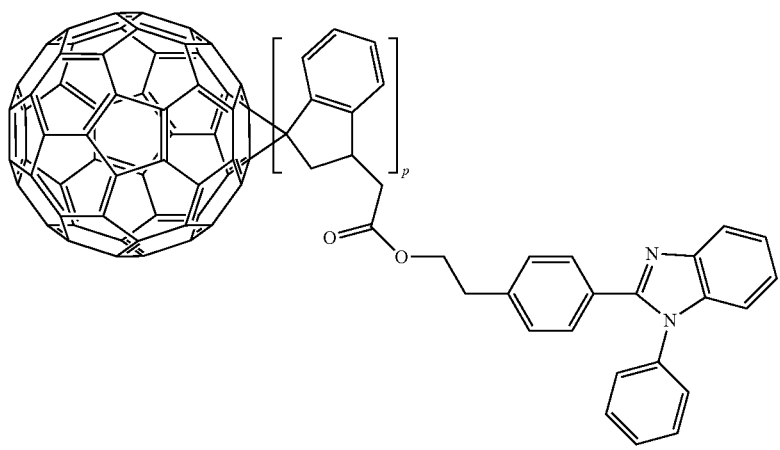
[Formula 1-1-20]
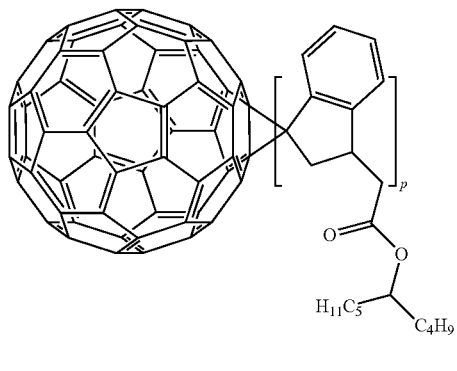
[Formula 1-1-21]
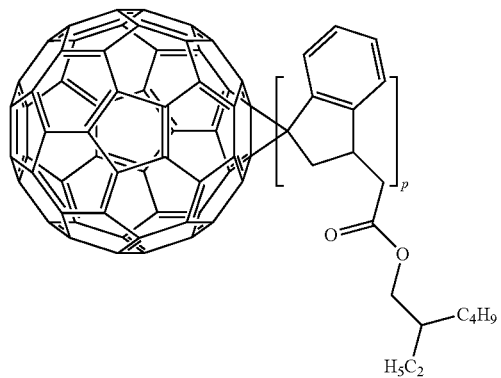

[Formula 1-1-22]
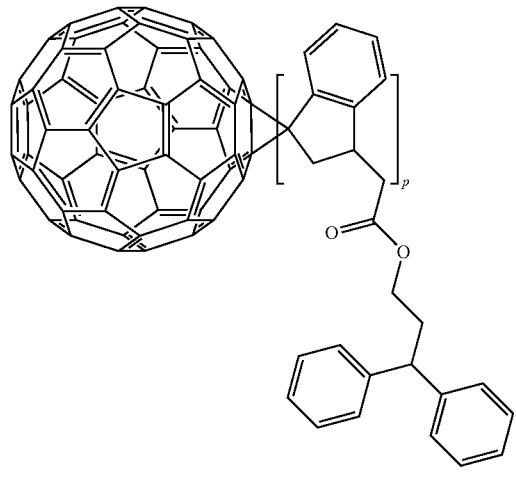
[Formula 1-1-23]
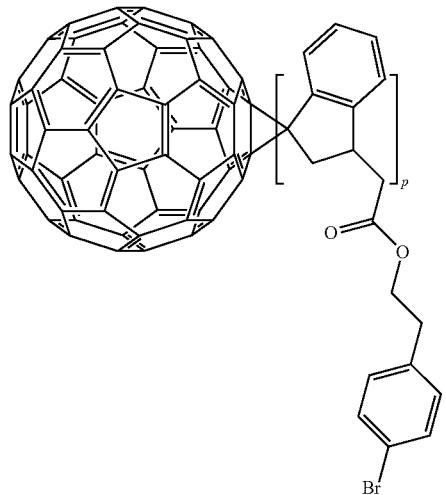
[Formula 1-1-24]
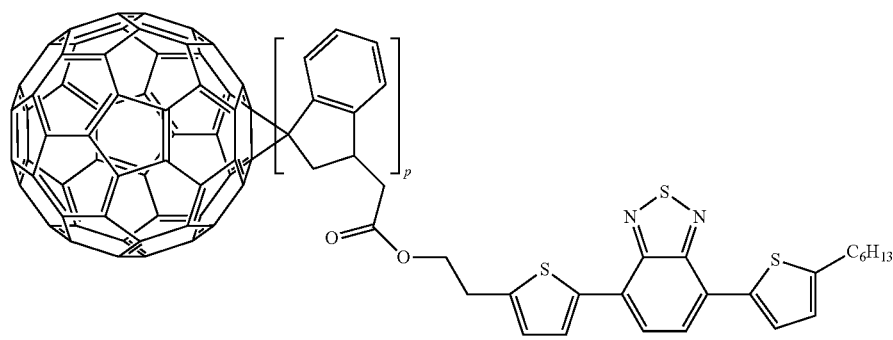
[Formula 1-1-25]
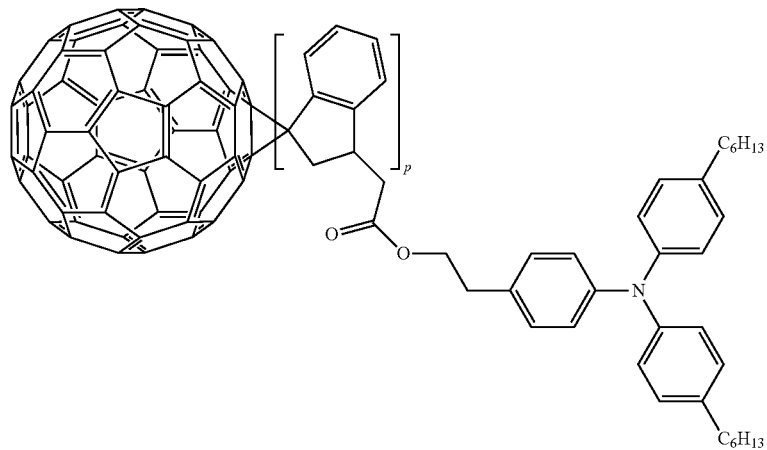

[Formula 1-1-26]
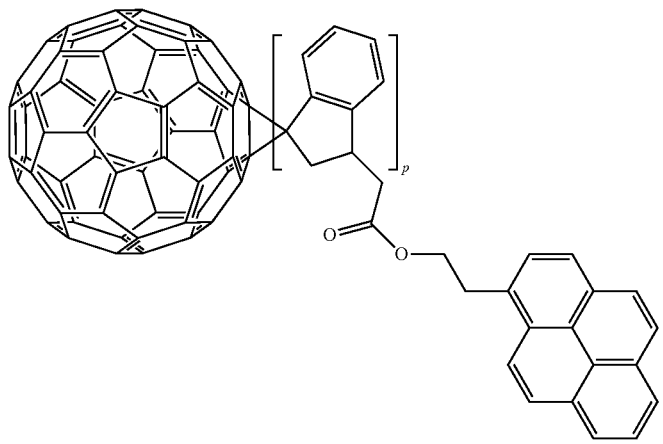
[Formula 1-1-27]
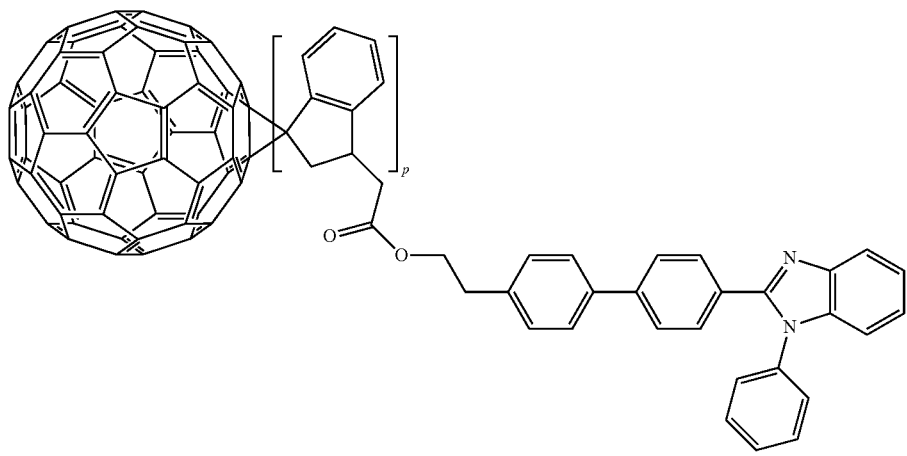
[Formula 1-1-28]
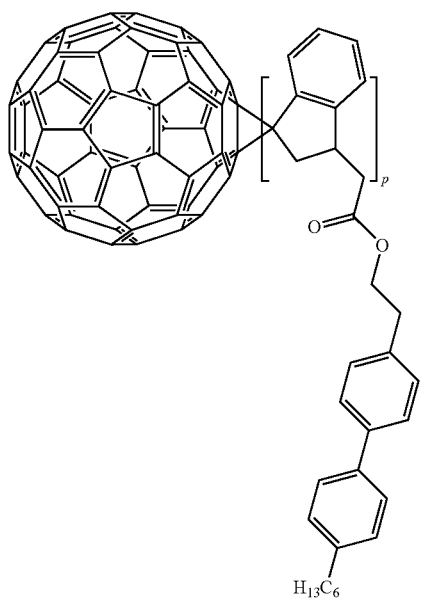
[Formula 1-1-29]
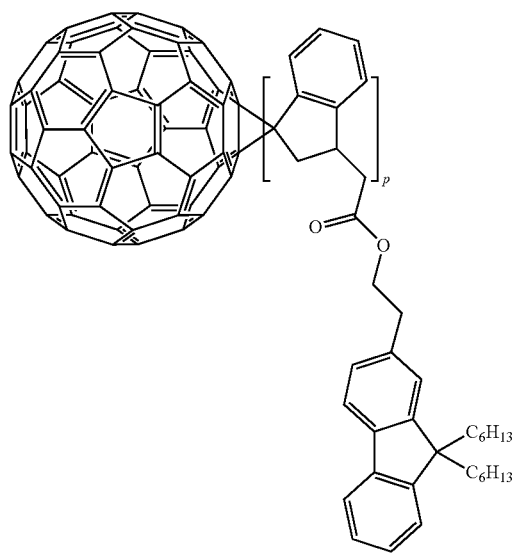

-continued
[Formula 1-1-30]
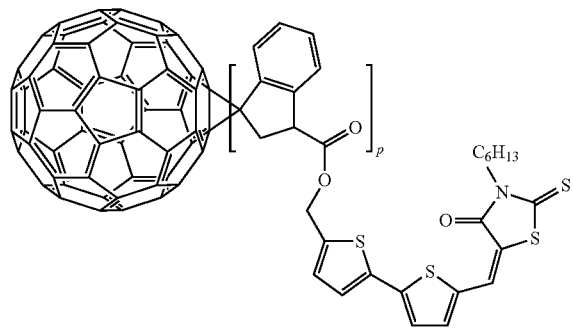
[Formula 1-1-31]
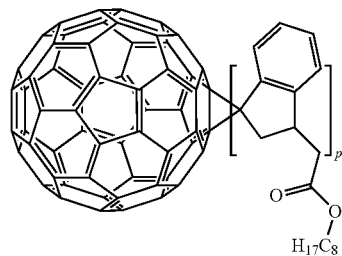
[Formula 1-1-32]
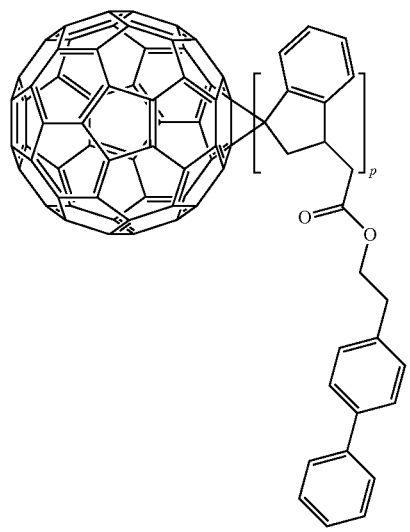
[Formula 1-1-33]
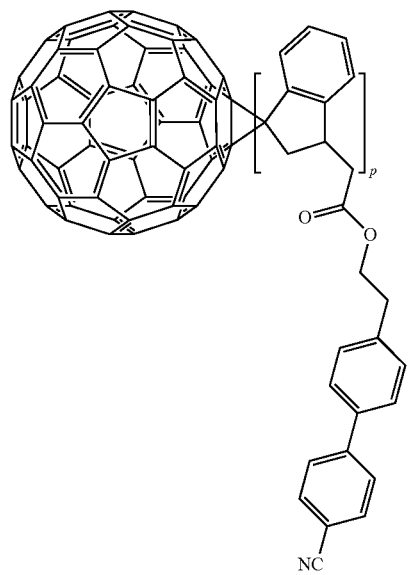
[Formula 1-1-34]
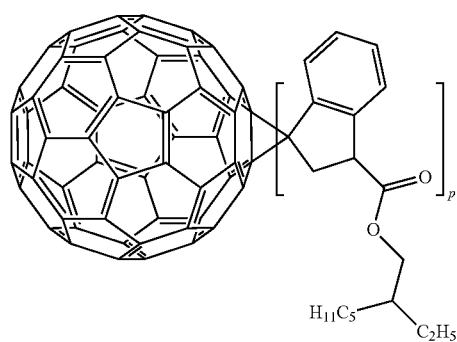
[Formula 1-1-35]
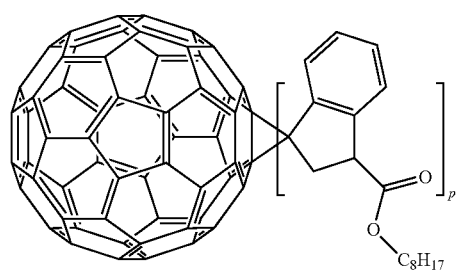
[Formula 1-1-36]
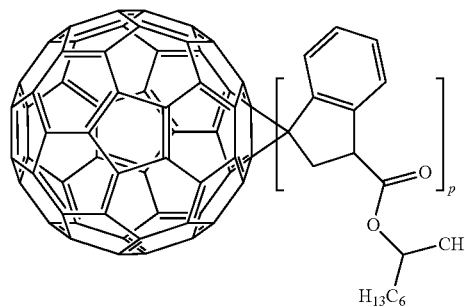
[Formula 1-1-37]
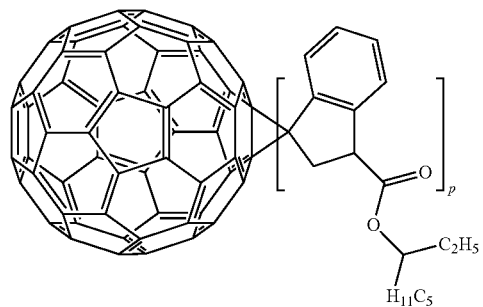

[Formula 1-1-38]
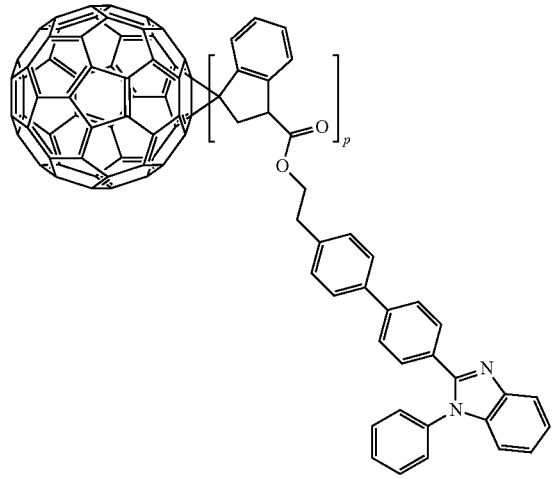
[Formula 1-1-39]
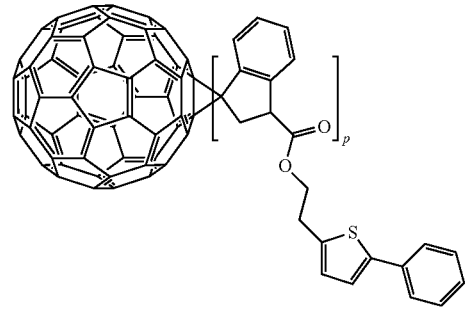
[Formula 1-1-40]
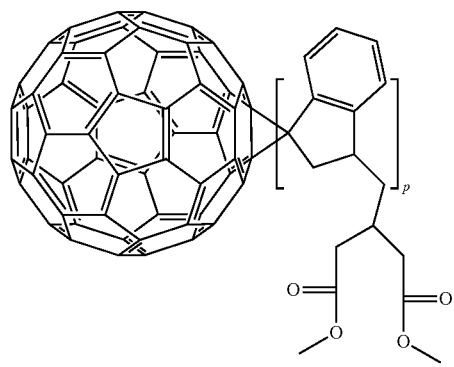
[Formula 1-1-41]
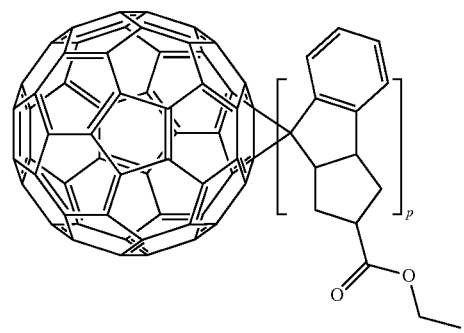
[Formula 1-1-42]
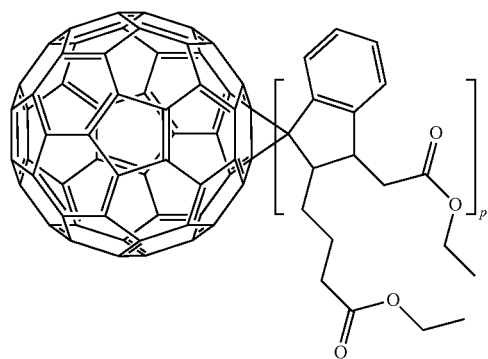
[Formula 1-1-43]
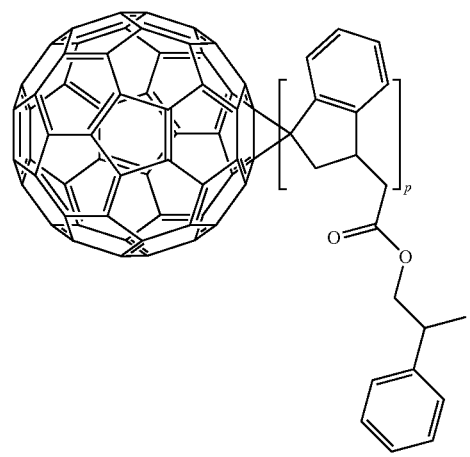

-continued
[Formula 1-1-44]
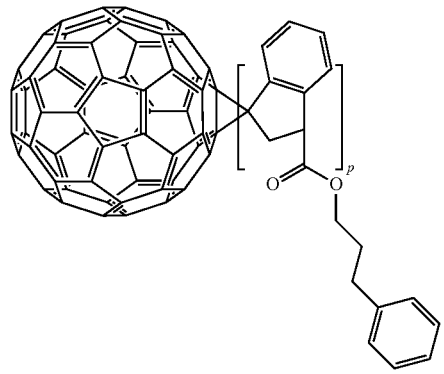
[Formula 1-1-45]
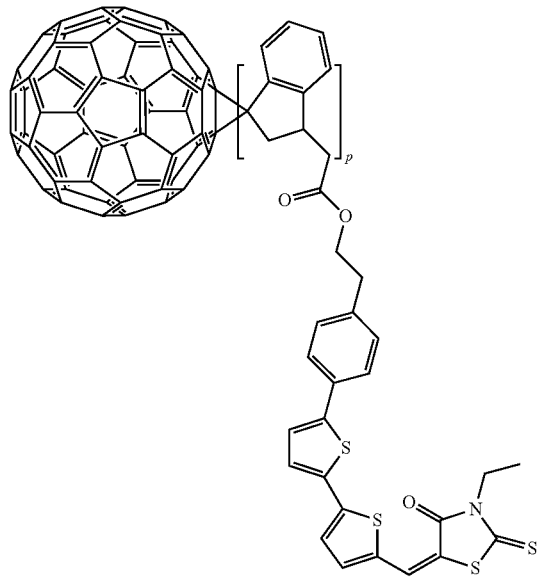
[Formula 1-1-46]
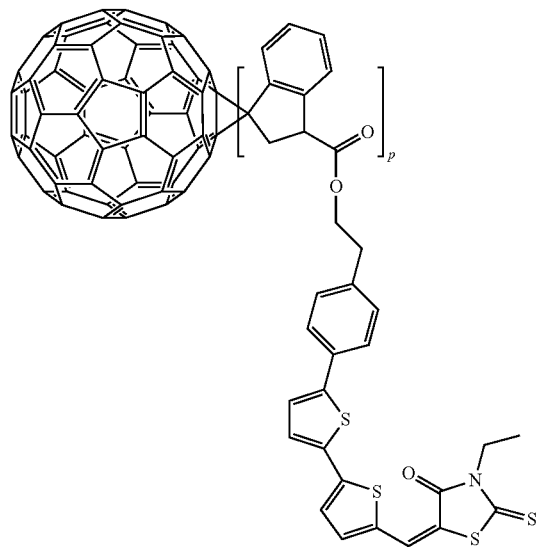
[Formula 1-1-47]
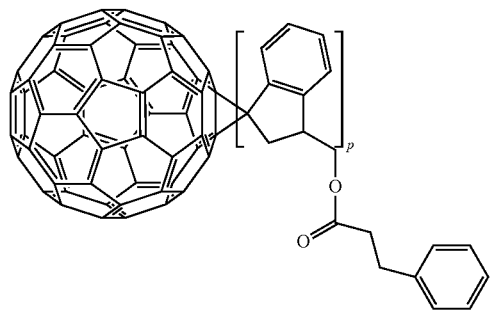
[Formula 1-1-48]
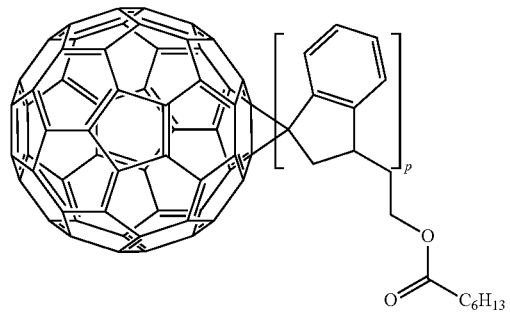
[Formula 1-1-49]
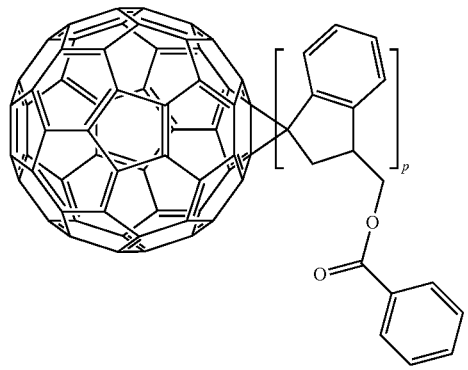

[Formula 1-1-50]

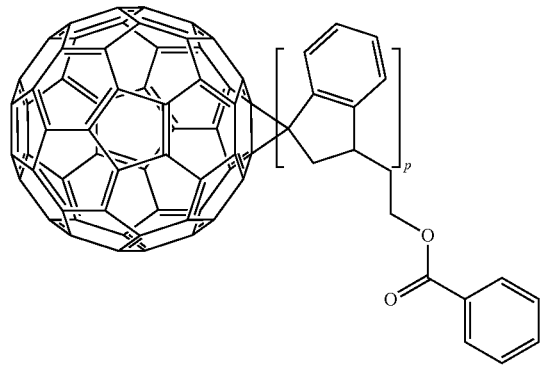

[Formula 1-1-51]

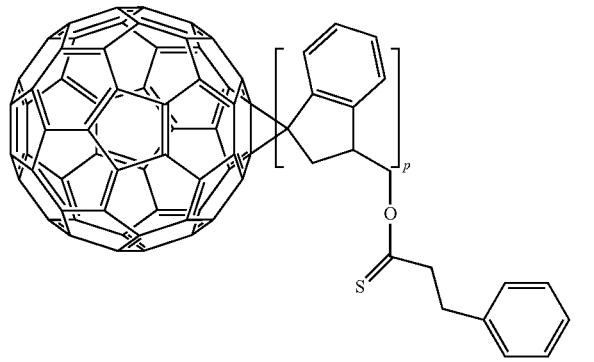

[Formula 1-1-52]

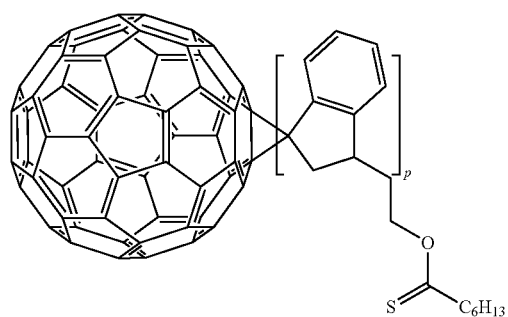

[Formula 1-1-53]

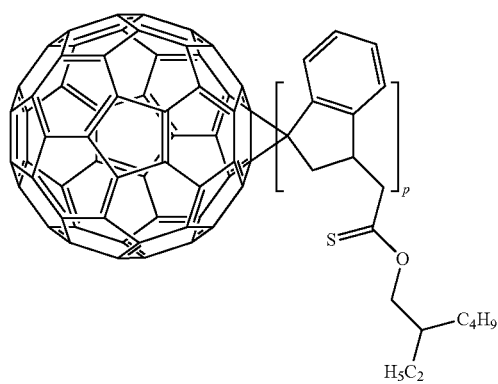

[Formula 1-1-54]

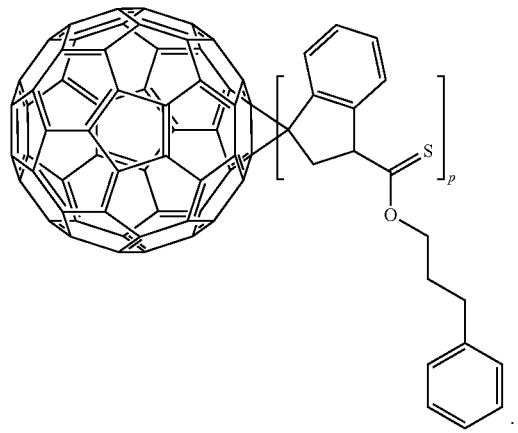

11. The fullerene derivative of claim 1, which has an LUMO energy level ranging from −3.4 eV to −5 eV.

12. An organic solar cell comprising:
a first electrode;
a second electrode provided opposite to the first electrode; and
one or more organic material layers provided between the first electrode and the second electrode,
wherein one or more layers of the organic material layers include the fullerene derivative of claim 1.

13. The organic solar cell of claim 12, wherein the organic material layer includes a photoactive layer; and
an organic material layer provided between the photoactive layer and the first electrode or the second electrode,
wherein, the organic material layer provided between the photoactive layer and the first electrode or the second electrode includes the fullerene derivative.

14. The organic solar cell of claim 12, wherein the organic material layer includes a photoactive layer;
the photoactive layer has a bilayer structure including an n-type organic material layer and a p-type organic material layer; and
the n-type organic material layer includes the fullerene derivative.

15. The organic solar cell of claim 12, wherein the organic material layer includes a photoactive layer;
the photoactive layer includes an electron donor material and an electron acceptor material; and
the electron acceptor material includes the fullerene derivative.

16. The organic solar cell of claim 15, wherein the electron donor material and the electron acceptor material form a bulk heterojunction (BHJ).

17. The organic solar cell of claim 15, wherein the electron donor material is P3HT or represented by the following Chemical Formula 2-1:

[Chemical Formula 2-1]

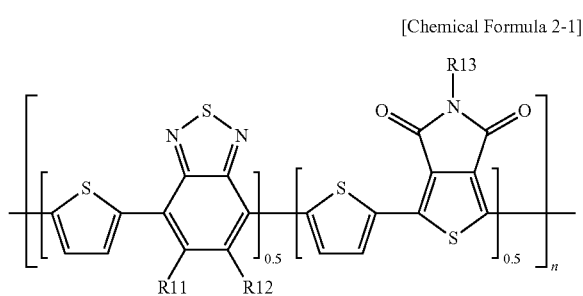

wherein, in Chemical Formula 2-1,
R11 to R13 are the same as or different from each other, and each independently is a substituted or unsubstituted alkyl group, or a substituted or unsubstituted alkoxy group.

18. A method for fabricating an organic solar cell comprising the steps of:
preparing a substrate;
forming a first electrode on top of the substrate;
forming one or more organic material layers including a photoactive layer on top of the first electrode; and
forming a second electrode on top of the organic material layers,
wherein one or more layers of the organic material layers include the fullerene derivative of claim 1.

19. An organic solar cell comprising:
a first electrode;
a second electrode provided opposite to the first electrode; and
one or more organic material layers provided between the first electrode and the second electrode,
wherein one or more layers of the organic material layers include the fullerene derivative of claim 10.

* * * * *